(12) United States Patent
Betancourt et al.

(10) Patent No.: US 10,512,619 B2
(45) Date of Patent: Dec. 24, 2019

(54) SOLID ORAL FORMULATION OF FENRETINIDE

(71) Applicant: LAURENT PHARMACEUTICALS, Montreal, Quebec (CA)

(72) Inventors: Aimesther Betancourt, Montreal (CA); Marc Lemieux, Montreal (CA); Roch Thibert, Mont-Royal (CA)

(73) Assignee: LAURENT PHARMACEUTICALS, Montreal (CA)

( * ) Notice: Subject to any disclaimer, the term of this patent is extended or adjusted under 35 U.S.C. 154(b) by 0 days.

(21) Appl. No.: 16/172,208

(22) Filed: Oct. 26, 2018

(65) Prior Publication Data

US 2019/0117599 A1 Apr. 25, 2019

Related U.S. Application Data

(62) Division of application No. 15/328,381, filed as application No. PCT/CA2015/000445 on Jul. 24, 2015.

(60) Provisional application No. 62/029,119, filed on Jul. 25, 2014.

(51) Int. Cl.
| | |
|---|---|
| *A61K 31/167* | (2006.01) |
| *A61K 9/20* | (2006.01) |
| *A61K 9/48* | (2006.01) |
| *A61K 9/14* | (2006.01) |
| *A61K 9/16* | (2006.01) |
| *A61K 9/50* | (2006.01) |

(52) U.S. Cl.
CPC ............ *A61K 31/167* (2013.01); *A61K 9/146* (2013.01); *A61K 9/1623* (2013.01); *A61K 9/1635* (2013.01); *A61K 9/1652* (2013.01); *A61K 9/2013* (2013.01); *A61K 9/2027* (2013.01); *A61K 9/2095* (2013.01); *A61K 9/4808* (2013.01); *A61K 9/4833* (2013.01); *A61K 9/4858* (2013.01); *A61K 9/4866* (2013.01); *A61K 9/5084* (2013.01)

(58) Field of Classification Search
CPC .. A61K 31/167; A61K 9/4866; A61K 9/4858; A61K 9/4833; A61K 9/4808; A61K 9/2027; A61K 9/2013; A61K 9/2095
See application file for complete search history.

(56) References Cited

U.S. PATENT DOCUMENTS

| | | | |
|---|---|---|---|
| 4,190,594 A | 2/1980 | Gander et al. | |
| 4,665,098 A | 5/1987 | Gibbs et al. | |
| 4,874,795 A | 10/1989 | Yesair | |
| 5,516,792 A | 5/1996 | Curley, Jr. et al. | |
| 5,574,177 A | 11/1996 | Curley, Jr. et al. | |
| 5,599,953 A | 2/1997 | Curley, Jr. et al. | |
| 5,663,377 A | 9/1997 | Curley, Jr. et al. | |
| 5,972,911 A | 10/1999 | Yesair | |
| 7,169,819 B2 | 1/2007 | Gupta et al. | |
| 7,780,988 B2 | 8/2010 | Beyerinck et al. | |
| 7,887,840 B2 | 2/2011 | Curatolo et al. | |
| 2006/0078615 A1 | 4/2006 | Kohlrausch | |
| 2006/0264514 A1 | 11/2006 | Formelli | |
| 2010/0008896 A1 | 1/2010 | Zhang et al. | |
| 2010/0021519 A1 | 1/2010 | Shenoy | |
| 2010/0297194 A1 | 11/2010 | Catron et al. | |
| 2011/0091383 A1 | 4/2011 | Kalpana et al. | |
| 2012/0093718 A1 | 4/2012 | Parchment et al. | |
| 2014/0056949 A1 | 2/2014 | Mallery et al. | |

FOREIGN PATENT DOCUMENTS

| | | |
|---|---|---|
| JP | 2000026270 | 1/2000 |
| JP | 2008007472 | 1/2008 |
| WO | 2002/058689 | 8/2002 |
| WO | 2005/084657 | 9/2005 |
| WO | 2007/068116 | 6/2007 |
| WO | 2007/136636 | 11/2007 |
| WO | 2008/006007 | 1/2008 |
| WO | 2009/016663 | 2/2009 |
| WO | 2009/103166 | 8/2009 |
| WO | 2009/114136 | 9/2009 |
| WO | 2012/078525 | 6/2012 |
| WO | 2014/169355 | 10/2014 |
| WO | 2016/011535 | 1/2016 |

OTHER PUBLICATIONS

JP2017-524071 Examination Report dated May 13, 2019.
Anding et al. (2007) Cancer Res. 67: 6270-6277.
Bhatnagar et al. (1991) Biochem. Pharmacol. 41: 1471-7.
Bostanian et al., Preparation and In Vitro Evaluation of Hydrophilic Fenretinide Nanoparticles, Int J Pharm, 2015, 479(2):329-337.

(Continued)

*Primary Examiner* — Zohreh A Fay

(74) *Attorney, Agent, or Firm* — Baker Donelson

(57) ABSTRACT

Amorphous solid dispersions suitable for oral delivery comprising fenretinide or an analog thereof and at least one matrix polymer, and processes for making the dispersions, are disclosed. Also disclosed are solid oral formulations comprising the amorphous solid dispersions, as well as uses thereof for the prevention and/or treatment of diseases or conditions treatable by fenretinide, including but not limited to cancers, conditions associated with a lipid imbalance, cystic fibrosis, osteoporosis, conditions associated with inflammation or opportunistic infections, and other diseases such as diabetes, obesity, dry-form age-related macular degeneration.

25 Claims, 22 Drawing Sheets

(56) References Cited

OTHER PUBLICATIONS

Charles, Anthony G., et al. "Taxol-induced ceramide generation and apoptosis in human breast cancer cells." Cancer chemotherapy and pharmacology 47.5 (2001): 444-450.
Desai et al., Development and In Vitro-In Vivo Evaluation of Fenretinide-Loaded Oral Mucoadhesive Patches for Site-Specific Chemoprevention of Oral Cancer, Pharm Res, 2011, 28(10)2599-2609.
European Search Report dated Jul. 6, 2017.
Falconi, Mirella, et al. "Novel PLA microspheres with hydrophilic and bioadhesive surfaces for the controlled delivery of fenretinide." Journal of microencapsulation 31.1 (2014): 41-48.
Garaventa, Alberto, et al. "Phase I trial and pharmacokinetics of fenretinide in children with neuroblastoma." Clinical Cancer Research 9.6 (2003): 2032-2039.
Graves et al., "Formulation of Biodegradable Fenretinide Nanoparticles", Poster #W4084 presented at the American Association of Pharmaceutical Scientists (AAPS) Annual Meeting in Nov. 2013.
Kummar, Shivaani, et al. "Phase I trial of fenretinide lym-x-sorb oral powder in adults with solid tumors and lymphomas." Anticancer research 31.3 (2011): 961-966.
Ledet et al., "Novel Method for the Preparation of Hydrophilic Fenretinide Nanoparticles", Poster #W4094 presented at the American Association of Pharmaceutical Scientists (AAPS) Annual Meeting in Nov. 2013.
Lippman, Scott M., et al. "Randomized phase III intergroup trial of isotretinoin to prevent second primary tumors in stage I non-small-cell lung cancer." Journal of the National Cancer Institute 93.8 (2001): 605-618.
Maurer, Barry J., et al. "Improved oral delivery of N-(4-hydroxyphenyl) retinamide with a novel LYM-X-SORB organized lipid complex." Clinical Cancer Research 13.10 (2007): 3079-3086.
Perry's Chemical Engineers' Handbook (eight edition).
Ponthan, Frida, et al. "Evaluation of anti-tumour effects of oral fenretinide (4-HPR) in rats with human neuroblastoma xenografts." Oncology reports 10.5 (2003): 1587-1592.
Puduvalli, Vinaykumar K., et al. "Fenretinide activates caspases and induces apoptosis in gliomas." Clinical cancer research 5.8 (1999): 2230-2235.
Rao, Ghanta N., Elizabeth Ney, and Ronald A. Herbert. "Effect of retinoid analogues on mammary cancer in transgenic mice with c-neu breast cancer oncogene." Breast cancer research and treatment 48.3 (1998): 265-271.
Sabnis et al., Pre-clinical evaluation of rHDL encapsulated retinoids for the treatment of neuroblastoma, Frontiers in Pediatrics, 2013, 1(6):1-10.
Wischke et al., Development of PLGA-Based Injectable Delivery Systems for Hydrophobic Fenretinide, Pharmaceutical Research, 2010, 27(10):2063-2074.

Table 36: Antioxidants/PVP based Fenretinide SDI Formulations (20 g of solids/lot)

| Ingredients | Lot No. | | | | |
| --- | --- | --- | --- | --- | --- |
| | L215-01023 | L215-01024 | L215-01025 | L215-01026 | L215-01027 |
| Fenretinide | 40.0% | 40.0% | 30.0% | 50.0% | 40.0% |
| Povidone, type K-29/32 | 59.6% | - | 69.6% | 49.6% | 30.0% |
| Povidone, type K-12 | - | 59.6% | - | - | 29.6% |
| BHA | 0.2% | 0.2% | 0.2% | 0.2% | 0.2% |
| BHT | 0.2% | 0.2% | 0.2% | 0.2% | 0.2% |
| DCM | 400 ml | 400 ml | 400 ml | 400 ml | 400 ml |
| Total solid phase: | 100% | 100% | 100% | 100% | 100% |

FIG. 17

Table 37: 100 mg Fenretinide Capsule (L215-01028) and Tablets (L215-01029 and 030)

| Ingredient name | Final blend % w/w | mg / unit | | |
|---|---|---|---|---|
| | | 028 Capsule | 029 Core Tablet | 030 Coated Tablet |
| Fenretinide 40% SDI lot # L215-01023 | 52.63 | 250.0 | 250.0 | 250.0 |
| *Fenretinide* | *Included in SDI* | *100.0* | *100.0* | *100.0* |
| *BHA* | | *0.5* | *0.5* | *0.5* |
| *BHT* | | *0.5* | *0.5* | *0.5* |
| *Povidone, type K-29/32* | | *149.0* | *149.0* | *149.0* |
| Microcrystalline cellulose | 16.84 | 80.0 | 80.0 | 80.0 |
| Dibasic calcium phosphate | 18.95 | 90.0 | 90.0 | 90.0 |
| Croscarmellose sodium | 5.37 | 25.5 | 25.5 | 25.5 |
| Ascorbic acid | 5.26 | 25.0 | 25.0 | 25.0 |
| Magnesium stearate | 0.95 | 4.5 | 4.5 | 4.5 |
| Total core: | 100.0 | 475.0 | 475.0 | 475.0 |
| Gelatin Capsules, Size 00 | N/A | 118.0 | N/A | N/A |
| Total uncoated: | N/A | 593.0 | 475.0 | 475.0 |
| Opadry™ AMB II 88A180040 white | N/A | N/A | N/A | 47.5 |
| Total coated: | N/A | N/A | N/A | 522.5 |

FIG. 18

Table 38: 100 mg Fenretinide Capsule (L215-01031) and Tablets (L215-01032 and 033)

| Ingredient name | Final blend % w/w | mg / unit | | |
|---|---|---|---|---|
| | | 031 Capsule | 032 Tablet | 033 Coated Tablet |
| Fenretinide 40% SDI lot # L215-01027 | 52.63 | 250.0 | 250.0 | 250.0 |
| *Fenretinide* | *Included in SDI* | *100.0* | *100.0* | *100.0* |
| *BHA* | | *0.5* | *0.5* | *0.5* |
| *BHT* | | *0.5* | *0.5* | *0.5* |
| *Povidone, type K-29/32* | | *75.0* | *75.0* | *75.0* |
| *Povidone, type K-12* | | *74.0* | *74.0* | *74.0* |
| Microcrystalline cellulose | 16.84 | 80.0 | 80.0 | 80.0 |
| Dibasic calcium phosphate | 18.95 | 90.0 | 90.0 | 90.0 |
| Croscarmellose sodium | 5.37 | 25.5 | 25.5 | 25.5 |
| Ascorbic acid | 5.26 | 25.0 | 25.0 | 25.0 |
| Magnesium stearate | 0.95 | 4.5 | 4.5 | 4.5 |
| Total core: | 100.0 | 475.0 | 475.0 | 475.0 |
| Gelatin Capsules, Size 00 | N/A | 118.0 | N/A | N/A |
| Total uncoated: | N/A | 593.0 | 475.0 | 475.0 |
| Opadry™ AMB II 88A180040 white | N/A | N/A | N/A | 47.5 |
| Total coated: | N/A | N/A | N/A | 522.5 |

FIG. 19

Table 39: Summary Results for Assay and Related Substances for SDI lots L215-01016 to 20, T=0, 1 and 3 months

| Lot # | C00324 | L215-01016 | L215-01017 | L215-01018 | L215-01019 | L215-01020 | L215-01015 |
|---|---|---|---|---|---|---|---|
| Sample ID | Crystalline API Cedarburg | Amorphous API 100% DL | SDI 40% DL PVPK30 (60%) | SDI 40% DL PVPK30 (59.6%) BHA (0.2%) BHT (0.2%) | SDI 40% DL HPMCAS (60%) | SDI 40% DL HPMCAS (59.6%) BHA (0.2%) BHT (0.2%) | GMP Clinical batch |
| %LC | | | | | | | |
| T=0 | | | | | | | |
| Total deg (%) | 0.25 | 0.61 | 0.39 | 0.25 | 0.54 | 0.31 | 0.50 |
| Assay (%LC) | 99.2 | 93.5 | 97.1 | 96.6 | 94.6 | 96.3 | 99.0 |
| T= 1 month 5°C closed cap | | | | | | | |
| Total deg (%) | 0.25 | 3.36 | 0.78 | 0.53 | 1.29 | 0.64 | 0.62 |
| Assay (%LC) | 99.2 | 82.6 | 95.8 | 96.6 | 92.3 | 95.3 | 95.5 |
| T= 3 months 5°C closed cap | | | | | | | |
| Total deg (%) | 0.24 | 21.5 | 3.89 | 3.37 | 5.43 | 4.23 | N/A |
| Assay (%LC) | 98.7 | 38.0 | 86.4 | 87.7 | 79.4 | 84.6 | |
| T= 1 month 25°C/60%RH closed cap | | | | | | | |
| Total deg (%) | 0.24 | 11.8 | 7.71 | 6.94 | 10.31 | 8.73 | 2.12 |
| Assay (%LC) | 98.4 | 44.4 | 70.5 | 71.4 | 57.3 | 68.9 | 89.8 |
| T= 3 month 25°C/60%RH closed cap | | | | | | | |
| Total deg (%) | 0.25 | 15.0 | 12.7 | 12.8 | 9.60 | 11.3 | N/A |
| Assay (%LC) | 99.2 | 51.8 | 40.1 | 44.7 | 61.7 | 57.7 | |
| T= 1 month 40°C/75%RH closed cap | | | | | | | 0.5 months |
| Total deg (%) | 0.25 | 8.26 | 7.95 | 7.07 | 13.3 | 15.0 | 2.76 |
| Assay (%LC) | 98.7 | 64.9 | 67.0 | 63.6 | 41.2 | 29.1 | 88.6 |
| T= 1 month 40°C/75%RH open cap | | | | | | | |
| Total deg (%) | 0.25 | 8.03 | 4.35 | 2.83 | 10.6 | 3.78 | N/A |
| Assay (%LC) | 96.7 | 5.2 | 66.1 | 74.6 | 35.3 | 78.6 | N/A |

FIG. 20

Table 40: Description, KF, Assay and Related Substances and Yield for SDI lots L215-01023 to 27 at T=0

| Lot # | C00324 | L215-01023 | L215-01024 | L215-01025 | L215-01026 | L215-01027 |
|---|---|---|---|---|---|---|
| Sample ID | CrystallineAPI Cedarburg | SDI 40% DL 59.6% PVPK30 + BHA + BHT | SDI 40% DL 59.6% PVPK12 + BHA + BHT | SDI 30% DL 69.6% PVPK30 + BHA + BHT | SDI 50% DL 49.6% PVPK30 + BHA + BHT | SDI 40% DL 30.0% PVPK30 29.6% PVPK12 + BHA + BHT |
| Description | | | | | | |
| Appearance | Yellow powder | Yellow powder | Yellow powder | Yellow powder | Yellow powder | Yellow powder |
| Water content | | | | | | |
| KF (%) | N/A | 1.8 | 2.4 | 2.9 | 1.9 | 2.5 |
| Assay and RS | | | | | | |
| Total RS (%) | 0.30 | 0.25 | 0.38 | 0.31 | 0.28 | 0.35 |
| Assay (%LC) | 99.9 | 98.1 | 93.3 | 95.8 | 99.1 | 95.8 |
| SDI collected in the receiving flask | | | | | | |
| Amount (g) | NA | 16.6 | 15.1 | 16.0 | 16.3 | 15.8 |
| Yield (%) | NA | 83 | 76 | 80 | 82 | 79 |

FIG. 21

Table 41: Summary Results for Assay and Related Substances for Drug Products lots L215-01023 to 27 at T=0, after 1 month, 3 months and 6 months

|  | L215-01023 | L215-01024 | L215-01025 | L215-01026 | L215-01027 |
|---|---|---|---|---|---|
|  | SDI 40% DL 59.6% PVPK30 + BHA + BHT | SDI 40% DL 59.6% PVPK12 + BHA + BHT | SDI 30% DL 69.6% PVPK30 + BHA + BHT | SDI 50% DL 49.6% PVPK30 + BHA + BHT | SDI 40% DL 30.0% PVPK30 29.6% PVPK12 + BHA + BHT |
| Description[a] | Yellow powder | Yellow powder | Yellow powder | Yellow powder | Yellow powder |
| Storage | T=0 | | | | |
| Total deg (% area) | 0.33 | 0.39 | 0.46 | 0.39 | 0.43 |
| Assay (%LC) | 99.2 | 95.6 | 96.5 | 100.3 | 97.3 |
| Storage | T=1 month 5°C | | | | |
| Total deg (% area) | 0.48 | 0.49 | 0.50 | 0.56 | 0.50 |
| Assay (%LC) | 98.4 | 95.1 | 96.9 | 99.0 | 97.6 |
| Storage | T=1 month 25°C 60% RH | | | | |
| Total deg (% area) | 0.88 | 2.13 | 0.86 | 5.96 | 0.81 |
| Assay (%LC) | 97.9 | 89.0 | 95.4 | 79.6 | 97.1 |
| Storage | T=3 months 5°C | | | | |
| Total deg (% area) | 1.06 | 1.08 | 0.67 | 1.72 | 0.74 |
| Assay (%LC) | 96.7 | 92.3 | 89.9 | 94.8 | 95.2 |
| Storage | T=3 months 25°C 60% RH | | | | |
| Total deg (% area) | 5.68 | 10.13 | 2.93 | 16.87 | 6.34 |
| Assay (%LC) | 80.8 | 67.6 | 88.7 | 38.8 | 73.8 |
| Storage | T=6 months 5°C | | | | |
| Total deg (% area) | 2.17 | Not analysed | | | 1.65 |
| Assay (%LC) | 87.9 | | | | 89.4 |

[a] No change in description was observed throughout the stability study.

FIG. 22

SOLID ORAL FORMULATION OF FENRETINIDE

CROSS REFERENCE TO RELATED APPLICATIONS

This application is a Divisional Application of U.S. patent application Ser. No. 15/328,381, filed on Jan. 23, 2017, which is a National Entry Application of PCT application no. PCT/CA2015/000445 filed on Jul. 24, 2015 and published in English under PCT Article 21(2), which itself claims the benefit of U.S. provisional application Ser. No. 62/029,119, filed on Jul. 25, 2014, each of which are incorporated by reference in their entireties.

TECHNICAL FIELD

The present invention generally relates to pharmaceutical formulations, and more specifically to oral pharmaceutical compositions comprising the active ingredient fenretinide or analogs thereof.

BACKGROUND ART

Fenretinide (all-trans-N-(4-hydroxyphenyl) retinamide; also referred to as 4-HPR), which has CAS registry number 65646-68-6, is a synthetic retinoid. Fenretinide was initially developed as a less toxic and better tolerated derivative of retinoic acid and has been extensively studied because of its chemo-protective and anti-tumor activities described when used on a variety of malignant cells, including non-small cell lung cancer, neuroblastoma, Kaposi's sarcoma, breast cancer and glioma (Charles, et al. (2001) *Cancer Chemother. Pharmacol.* 47:444-450; Garaventa, et al. (2003) *Clin. Cancer Res.* 9:2032-2039; Lippman, et al. (2001) *J. Natl. Cancer Inst.* 93:605-618; Ponthan, et al. (2003) *Oncol. Rep.* 10:1587-1592; Puduvalli, et al. (1999) *Clin. Cancer Res.* 5:2230-2235; Rao, et al. (1998) *Breast Cancer Res. Treat.* 48:265-271), and has been approved for clinical trials of cancer patients. However, despite its promising anticancer activity in preclinical studies, its limited oral bioavailability, notably due to its poor water solubility, represents a significant challenge for its clinical assessment.

Fenretinide has been formulated in corn oil-containing soft-gelatin capsules, but such formulations have been shown to result in variable and low systemic exposures (i.e. poor bioavailability). Also, because of their size, patient compliance has been shown to be a concern with these corn oil-containing capsules, especially in pediatric subjects. Fenretinide has also been formulated in a lipid matrix, Lym-X-Sorb (LXS), (Maurer B J, *Clin Cancer Res* 13: 3079-3086, 2007), administered as an oral powder delivered in non-milk fat-containing foods, and especially as a slurry in non-milk fat-containing, or soy-based nutritional supplements. However, this formulation has been shown to be associated with significant gastrointestinal (GI) side-effects, especially at higher doses (Kummar et al. (2011) *Anticancer Research* 31(3):961-966), as well as to significant patient withdrawal due to the taste and texture of the medication.

There is thus a need for new pharmaceutical compositions of fenretinide, especially for oral administration, capable to overcome the poor oral bioavailability of corn-oil based formulation, while allowing for more compliant pharmaceutical dosage forms such as hard gelatine capsules, tablets, strips, caplets, suspensions, or powders for suspensions.

The present description refers to a number of documents, the content of which is herein incorporated by reference in their entirety.

SUMMARY OF THE INVENTION

In a first aspect, the present invention relates to the preparation of oral formulations which comprises the amorphous state of the active ingredient fenretinide or analogs thereof. Such chemically and/or physically stable formulations are composed of solid dispersions (e.g., spray-dried), such as microparticles which contain fenretinide or one of its analogs, where its amorphous state is maintained over time. Its amorphous state is associated with improved oral bioavailability following oral administration, when compared to crystalline fenretinide. The amorphous solid dispersion of fenretinide can be orally-administered in an acceptable pharmaceutical form such as hard gelatine capsule, tablets, strips, caplets, cachets, lozenges, suspensions, or powders for suspensions.

In other aspects, the present invention relates to the following items 1 to 116:

1. An amorphous solid dispersion for oral delivery comprising fenretinide or an analog thereof and at least one matrix polymer.
2. The amorphous solid dispersion of item 1, wherein the at least one matrix polymer is a polyvinylpyrrolidone, a hydroxypropyl cellulose, a hydroxypropyl methylcellulose hypromellose phthalate, a polyvinylpyrrolidone-vinyl acetate, a hypromellose-acetate-succinate, or any mixture thereof.
3. The amorphous solid dispersion of item 2, wherein the polyvinylpyrrolidone polymer is polyvinylpyrrolidone K12, polyvinylpyrrolidone K17, polyvinylpyrrolidone K25, polyvinylpyrrolidone K30, polyvinylpyrrolidone K90, or any mixture thereof.
4. The amorphous solid dispersion of any one of items 1 to 3, wherein the fenretinide or analog thereof is present in an amount in the range of about 20% to about 60% by weight.
5. The amorphous solid dispersion of item 4, wherein the fenretinide or analog thereof is present in an amount in the range of about 30% to about 50% by weight.
6. The amorphous solid dispersion of item 5, wherein the fenretinide or analog thereof is present in an amount of about 40% by weight.
7. The amorphous solid dispersion of any one of items 1 to 6, where the amorphous state is obtained by fast evaporation, spray-drying, precipitation or melt extrusion.
8. The amorphous solid dispersion of item 7, where the amorphous state is obtained by spray-drying
9. The amorphous solid dispersion of any one of items 1 to 8, comprising fenretinide.
10. The amorphous solid dispersion of any one of items 1 to 9, further comprising an antioxidant.
11. The amorphous solid dispersion of item 10, wherein the antioxidant is butylated hydroxyanisole (BHA), butylated hydroxytoluene (BHT), citric acid, sodium metabisulfite, alpha-tocopherol and/or L-ascorbic acid.
12. The amorphous solid dispersion of item 11, wherein the antioxidant is L-ascorbic acid.
13. A process for making the amorphous solid dispersion according to any one of items 1 to 12, the process comprising:
   (a) forming a solution comprising the fenretinide or analog thereof, the at least one matrix polymer, and a solvent or solvent mixture in which both the fenretinide or analog thereof and the at least one matrix polymer are soluble; and (b) spray-drying the solution of step (a), thereby obtaining the amorphous solid dispersion.

14. The process of item 13, where the solvent or solvent mixture comprises dichloromethane, methanol and/or ethanol.

15. The process of item 14, where the solvent is dichloromethane, methanol or ethanol.

16. The process of any one of items 13 to 15, where the solution further comprises an antioxidant.

17. The process of item 16, wherein the antioxidant is butylated hydroxyanisole (BHA), butylated hydroxytoluene (BHT), citric acid, sodium metabisulfite, and/or L-ascorbic acid.

18. The process of item 17, wherein the antioxidant is L-ascorbic acid.

19. A spray-dried amorphous solid dispersion obtained by the process of any one of items 13 to 18.

20. An oral dosage formulation comprising the amorphous solid dispersion of any one of items 1-12 and 19.

21. The oral dosage formulation of item 20, wherein the amorphous solid dispersion is present in an amount from about 20 to about 80% by weight.

22. The oral dosage formulation of item 21, wherein the amorphous solid dispersion is present in an amount from 30 to 60% by weight.

23. The oral dosage formulation of item 22, wherein the amorphous solid dispersion is present in an amount from about 45 to about 55% by weight.

24. The oral dosage formulation of item 23, wherein the amorphous solid dispersion is present in an amount from about 50% by weight.

25. The oral dosage formulation of any one of items 20-24, wherein the fenretinide or analog thereof is present in an amount from about 10 to about 250 mg per dose unit.

26. The oral dosage formulation of item 25, wherein the fenretinide or analog thereof is present in an amount from about 25 mg to about 200 mg per dose unit.

27. The oral dosage formulation of item 26, wherein the fenretinide or analog thereof is present in an amount from about 50 mg to about 150 mg per dose unit.

28. The oral dosage formulation of item 27, wherein the fenretinide or analog thereof is present in an amount of about 100 mg per dose unit.

29. The oral dosage formulation of any one of items 20-28, further comprising at least one additional pharmaceutical excipient.

30. The oral dosage formulation of item 29, wherein said at least one additional pharmaceutical excipient comprises a disintegrant.

31. The oral dosage formulation of item 30, wherein said disintegrant is a cross-linked sodium carboxymethylcellulose.

32. The oral dosage formulation of item 30 or 31, wherein said disintegrant is present in an amount from about 2 to about 10% by weight.

33. The oral dosage formulation of item 32, wherein said disintegrant is present in an amount from about 4 to about 6% by weight.

34. The oral dosage formulation of any one of items 29-32, wherein said at least one additional pharmaceutical excipient comprises a lubricant.

35. The oral dosage formulation of item 34, wherein said lubricant comprises magnesium stearate.

36. The oral dosage formulation of item 34 or 35, wherein said lubricant is present in an amount from about 0.5 to about 2% by weight.

37. The oral dosage formulation of item 36, wherein said lubricant is present in an amount of about 1% by weight.

38. The oral dosage formulation of any one of items 29-37, wherein said at least one additional pharmaceutical excipient comprises a filler or binder.

39. The oral dosage formulation of item 38, wherein said filler or binder comprises microcrystalline cellulose.

40. The oral dosage formulation of item 38 or 39, wherein said filler or binder comprises calcium hydrogen phosphate dihydrate.

41. The oral dosage formulation of any one of items 38 to 40, wherein said filler or binder is present in an amount from about 20% to about 45% by weight.

42. The oral dosage formulation of item 41, wherein said filler or binder is present in an amount from about 30% to about 40% by weight.

43. The oral dosage formulation of any one of items 29-42, wherein said at least one additional pharmaceutical excipient comprises an antioxidant.

44. The amorphous solid dispersion of item 43, wherein the antioxidant is butylated hydroxyanisole (BHA), butylated hydroxytoluene (BHT), citric acid, sodium metabisulfite, alpha-tocopherol and/or L-ascorbic acid.

45. The amorphous solid dispersion of item 44, wherein the antioxidant is L-ascorbic acid.

46. The oral dosage formulation of any one of items 20 to 45, which is in an acceptable pharmaceutical form for oral administration.

47. The oral dosage formulation of item 46, wherein said acceptable pharmaceutical form is a hard gelatine capsule, a tablet, a strip, a caplet, a sachet, a lozenge, a suspension, or a powder for suspension.

48. A method for preventing, treating, and/or lessening the severity of cancer in a subject, said method comprising administering to a subject in need thereof an effective amount of the amorphous solid dispersion according to any one of items 1-12 and 19, or the oral dosage formulation according to any one of items 20-47.

49. The method of item 48, wherein said cancer is breast cancer, ovarian cancer, prostate cancer, cervical cancer, lung cancer, renal cancer, bladder cancer, glioma, skin cancer, head and neck carcinoma, non-Hodgkin's lymphoma, neuroblastoma, Ewing's sarcoma or Kaposi's sarcoma.

50. A method for preventing, treating, and/or lessening the severity of, a disease or condition associated with a lipid imbalance, said method comprising administering to a subject in need thereof an effective amount of the amorphous solid dispersion according to any one of items 1-12 and 19, or the oral dosage formulation according to any one of items 20-47.

51. The method of item 50, wherein said disease or condition associated with lipid imbalance is Cystic Fibrosis.

52. The method of item 50, wherein said disease or condition associated with lipid imbalance is a respiratory disease, a neural injury, or a neurodegenerative disease.

53. A method for preventing, treating, and/or lessening the severity of Cystic Fibrosis or a condition associated with Cystic Fibrosis, said method comprising administering to a subject in need thereof an effective amount of the amorphous solid dispersion according to any one of items 1-12 and 19, or the oral dosage formulation according to any one of items 20-47.

54. A method for preventing, treating, and/or lessening the severity of a bone disease, or a condition associated with a bone disease, said method comprising administering to a subject in need thereof an effective amount of the amorphous solid dispersion according to any one of items 1-12 and 19, or the oral dosage formulation according to any one of items 20-47.

55. The method of item 54, wherein said subject suffers from Cystic Fibrosis.

56. A method for preventing, treating, and/or lessening the severity of a disease or condition associated with inflammation, said method comprising administering to a subject in need thereof an effective amount of the amorphous solid dispersion according to any one of items 1-12 and 19, or the oral dosage formulation according to any one of items 20-47.

57. The method of item 56, wherein said disease or condition associated with inflammation is a respiratory disease, a neural injury, or a neurodegenerative disease.

58. The method of item 56, wherein said inflammation is lung inflammation, and the disease or condition associated with lung inflammation is Cystic Fibrosis.

59. The method of item 57, wherein said neural injury is Spinal Cord Injury (SCI)

60. The method of item 57, wherein said neurodegenerative disease is Amyotrophic Lateral Sclerosis (ALS).

61. A method for preventing, treating, and/or lessening the severity of an opportunistic infection or a condition associated with an opportunistic infection, said method comprising administering to a subject in need thereof an effective amount of the amorphous solid dispersion according to any one of items 1-12 and 19, or the oral dosage formulation according to any one of items 20-47.

62. The method of item 61, wherein said condition associated with an opportunistic infection is a respiratory disease.

63. The method of items 62, wherein said respiratory disease is Cystic Fibrosis.

64. A method for preventing, treating, and/or lessening the severity of a disease in a subject, wherein the disease is allergic asthma, Spinal Cord Injury, Amyotrophic Lateral Sclerosis, diabetes, obesity, macular degeneration, AIDS, allergic encephalomyelitis, ichthyosis or a viral infection caused by a flavivirus, said method comprising administering to a subject in need thereof an effective amount of the amorphous solid dispersion according to any one of items 1-12 and 19, or the oral dosage formulation according to any one of items 20-47.

65. Use of the amorphous solid dispersion according to any one of items 1-12 and 19, or the oral dosage formulation according to any one of items 20-47, for preventing, treating, and/or lessening the severity of cancer in a subject.

66. Use of the amorphous solid dispersion according to any one of items 1-12 and 19, or the oral dosage formulation according to any one of items 20-47, for the manufacture of a medicament for preventing, treating, and/or lessening the severity of cancer in a subject.

67. The use of item 65 or 66, wherein said cancer is breast cancer, ovarian cancer, prostate cancer, cervical cancer, lung cancer, renal cancer, bladder cancer, glioma, skin cancer, head and neck carcinoma, non-Hodgkin's lymphoma, neuroblastoma, Ewing's sarcoma or Kaposi's sarcoma.

68. Use of amorphous solid dispersion according to any one of items 1-12 and 19, or the oral dosage formulation according to any one of items 20-47, for preventing, treating, and/or lessening the severity of a disease or condition associated with a lipid imbalance in a subject.

69. Use of amorphous solid dispersion according to any one of items 1-12 and 19, or the oral dosage formulation according to any one of items 20-47, for the manufacture of a medicament for preventing, treating, and/or lessening the severity of a disease or condition associated with a lipid imbalance in a subject.

70. The use of item 68 or 69, wherein said disease or condition associated with lipid imbalance is Cystic Fibrosis.

71. The use of item 68 or 69, wherein said disease or condition associated with lipid imbalance is a respiratory disease, a neural injury, or a neurodegenerative disease.

72. The use of item 71, wherein said neural injury is Spinal Cord Injury (SCI)

73. The use of item 71, wherein said neurodegenerative disease is Amyotrophic Lateral Sclerosis (ALS).

74. Use of the amorphous solid dispersion according to any one of items 1-12 and 19, or the oral dosage formulation according to any one of items 20-47, for preventing and/or treating Cystic Fibrosis or a condition associated with Cystic Fibrosis in a subject.

75. Use of the amorphous solid dispersion according to any one of items 1-12 and 19, or the oral dosage formulation according to any one of items 20-47, for the manufacture of a medicament for preventing, treating, and/or lessening the severity of Cystic Fibrosis or a condition associated with Cystic Fibrosis in a subject.

76. Use of the amorphous solid dispersion according to any one of items 1-12 and 19, or the oral dosage formulation according to any one of items 20-47, for preventing, treating, and/or lessening the severity of a bone disease or condition associated with a bone disease in a subject.

77. Use of the amorphous solid dispersion according to any one of items 1-12 and 19, or the oral dosage formulation according to any one of items 20-47, for the manufacture of a medicament for preventing, treating, and/or lessening the severity of a bone disease or condition associated with a bone disease in a subject.

78. The use of item 76 or 77, wherein said subject suffers from Cystic Fibrosis.

79. Use of the amorphous solid dispersion according to any one of items 1-12 and 19, or the oral dosage formulation according to any one of items 20-47, for preventing, treating and/or lessening the severity of a disease or condition associated with inflammation in a subject.

80. Use of the amorphous solid dispersion according to any one of items 1-12 and 19, or the oral dosage formulation according to any one of items 20-47, for the manufacture of a medicament for preventing, treating and/or lessening the severity of a disease or condition associated with inflammation in a subject.

81. The use of item 79 or 80, wherein said inflammation is lung inflammation, and the disease or condition associated with lung inflammation is Cystic Fibrosis.

82. The use of item 78 or 80, wherein said disease or condition associated with inflammation is a respiratory disease, a neural injury, or a neurodegenerative disease.

83. The use of item 82, wherein said respiratory disease is allergic asthma.

84. The use of item 82, wherein said neural injury is Spinal Cord Injury (SCI).

85. The use of item 82, wherein said neurodegenerative disease is Amyotrophic Lateral Sclerosis (ALS).

86. Use of the amorphous solid dispersion according to any one of items 1-12 and 19, or the oral dosage formulation according to any one of items 20-47, for preventing, treating, and/or lessening the severity of a disease or condition associated with opportunistic infection in a subject.

87. Use of the amorphous solid dispersion according to any one of items 1-12 and 19, or the oral dosage formulation according to any one of items 20-47, for the manufacture of a medicament for preventing, treating, and/or lessening the severity of a disease or condition associated with opportunistic infection in a subject.

88. The use of item 86 or 87, wherein said disease or condition associated with an opportunistic infection is a respiratory disease.

89. The method of item 88, wherein said respiratory disease is Cystic Fibrosis.

90. Use of the amorphous solid dispersion according to any one of items 1-12 and 19, or the oral dosage formulation according to any one of items 20-47, for preventing, treating, and/or lessening the severity of a disease in a subject, wherein the disease is allergic asthma, Spinal Cord Injury, Amyotrophic Lateral Sclerosis, diabetes, obesity, macular degeneration, AIDS, allergic encephalomyelitis, ichthyosis, or a viral infection caused by a flavivirus.

91. Use of the amorphous solid dispersion according to any one of items 1-12 and 19, or the oral dosage formulation according to any one of items 20-47, for the manufacture of a medicament for preventing, treating, and/or lessening the severity of a disease in a subject, wherein the disease is allergic asthma, Spinal Cord Injury, Amyotrophic Lateral Sclerosis, diabetes, obesity, macular degeneration, AIDS, allergic encephalomyelitis, ichthyosis or a viral infection caused by a flavivirus.

92. The amorphous solid dispersion according to any one of items 1-12 and 19, or the oral dosage formulation according to any one of items 20-47, for use in the prevention and/or treatment of cancer in a subject.

93. The amorphous solid dispersion according to any one of items 1-12 and 19, or the oral dosage formulation according to any one of items 20-47, for use in the manufacture of a medicament for the prevention and/or treatment of cancer in a subject.

94. The amorphous solid dispersion or oral dosage formulation for use according to item 92 or 93, wherein said cancer is breast cancer, ovarian cancer, prostate cancer, cervical cancer, lung cancer, renal cancer, bladder cancer, glioma, skin cancer, head and neck carcinoma, non-Hodgkin's lymphoma, neuroblastoma, Ewing's sarcoma or Kaposi's sarcoma.

95. The amorphous solid dispersion according to any one of items 1-12 and 19, or the oral dosage formulation according to any one of items 20-47, for use in preventing, treating, and/or lessening the severity of a disease or condition associated with a lipid imbalance in a subject.

96. The amorphous solid dispersion according to any one of items 1-12 and 19, or the oral dosage formulation according to any one of items 20-47, for use in the manufacture of a medicament for preventing, treating, and/or lessening the severity of a disease or condition associated with a lipid imbalance in a subject.

97. The amorphous solid dispersion or oral dosage formulation for use according to item 95 or 96, wherein said disease or condition associated with lipid imbalance is Cystic Fibrosis.

98. The amorphous solid dispersion or oral dosage formulation for use according to item 95 or 96, wherein said disease or condition associated with lipid imbalance is a respiratory disease, a neural injury, or a neurodegenerative disease.

99. The amorphous solid dispersion according to any one of items 1-12 and 19, or the oral dosage formulation according to any one of items 20-47, for use in the prevention, treatment, and/or lessening the severity of Cystic Fibrosis or a condition associated with Cystic Fibrosis in a subject.

100. The amorphous solid dispersion according to any one of items 1-12 and 19, or the oral dosage formulation according to any one of items 20-47, for use in the manufacture of a medicament for preventing, treating, and/or lessening the severity of Cystic Fibrosis or a condition associated with Cystic Fibrosis in a subject.

101. The amorphous solid dispersion according to any one of items 1-12 and 19, or the oral dosage formulation according to any one of items 20-47, for use in preventing, treating, and/or lessening the severity of a bone disease or condition associated with a bone disease in a subject.

102. The amorphous solid dispersion according to any one of items 1-12 and 19, or the oral dosage formulation according to any one of items 20-47, for use in the manufacture of a medicament for preventing, treating, and/or lessening the severity of a bone disease or condition associated with a bone disease in a subject.

103. The amorphous solid dispersion or oral dosage formulation for use according to item 102 or 103, wherein said disease or condition associated with bone disease is Cystic Fibrosis.

104. The amorphous solid dispersion according to any one of items 1-12 and 19, or the oral dosage formulation according to any one of items 20-47, for use in preventing, treating and/or lessening the severity of a disease or condition associated with inflammation in a subject.

105. The amorphous solid dispersion according to any one of items 1-12 and 19, or the oral dosage formulation according to any one of items 20-47, for use in the manufacture of a medicament for preventing, treating, and/or lessening the severity of a disease or condition associated with inflammation in a subject.

106. The amorphous solid dispersion or oral dosage formulation for use according to item 104 or 105, wherein said inflammation is lung inflammation, and the disease or condition associated with lung inflammation is Cystic Fibrosis.

107. The amorphous solid dispersion or oral dosage formulation for use according to item 104 or 105, wherein said disease or condition associated with inflammation is a respiratory disease, a neural injury, or a neurodegenerative disease.

108. The amorphous solid dispersion or oral dosage formulation for use according to item 107, wherein said respiratory disease is allergic asthma.

109. The amorphous solid dispersion or oral dosage formulation for use according to item 107, wherein said neural injury is Spinal Cord Injury (SCI).

110. The amorphous solid dispersion or oral dosage formulation for use according to item 107, wherein said neurodegenerative disease is Amyotrophic Lateral Sclerosis (ALS).

111. The amorphous solid dispersion according to any one of items 1-12 and 19, or the oral dosage formulation according to any one of items 20-47, for use in preventing, treating, and/or lessening the severity of a disease or condition associated with opportunistic infection in a subject.

112. The amorphous solid dispersion according to any one of items 1-12 and 19, or the oral dosage formulation according to any one of items 20-47, for use in the manufacture of a medicament for preventing, treating, and/or lessening the severity of a disease or condition associated with opportunistic infection in a subject.

113. The amorphous solid dispersion or oral dosage formulation for use according to item 111 or 112, wherein said disease or condition is associated with an opportunistic infection is a respiratory disease.

114. The amorphous solid dispersion or oral dosage formulation for use according to item 113, wherein said respiratory disease is Cystic Fibrosis.

115. The amorphous solid dispersion according to any one of items 1-12 and 19, or the oral dosage formulation according to any one of items 20-47, for use in preventing, treating, and/or lessening the severity of a disease in a subject, wherein the disease is allergic asthma, Spinal Cord Injury, Amyotrophic Lateral Sclerosis, diabetes, obesity, macular degeneration, AIDS, allergic encephalomyelitis, ichthyosis or a viral infection caused by a flavivirus.

116. The amorphous solid dispersion according to any one of items 1-12 and 19, or the oral dosage formulation according to any one of items 20-47, for use in the manufacture of a medicament for preventing, treating, and/or lessening the severity of a disease in a subject, wherein the disease is allergic asthma, Spinal Cord Injury, Amyotrophic Lateral Sclerosis, diabetes, obesity, dry-form age-related macular degeneration, Stargardt Disease, AIDS, allergic encephalomyelitis, ichthyosis or a viral infection caused by a flavivirus.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIG. 17 shows antioxidants/PVP based Fenretinide SDI Formulations (20 g of solids/lot)

FIG. 18 shows 100 mg Fenretinide Capsule (L215-01028) and Tablets (L215-01029 and 030)

FIG. 19 shows 100 mg Fenretinide Capsule (L215-01031) and Tablets (L215-01032 and 033)

FIG. 20 shows Summary Results for Assay and Related Substances for SDI lots L215-01016 to 20, T=0, 1 and 3 months.

FIG. 21 shows Description, KF, Assay and Related Substances and Yield for SDI lots L215-01023 to 27 at T=0

FIG. 22 shows Summary Results for Assay and Related Substances for Drug Products lots L215-01023 to 27 at T=0, after 1 month, 3 months and 6 months

DISCLOSURE OF INVENTION

Figure 1:
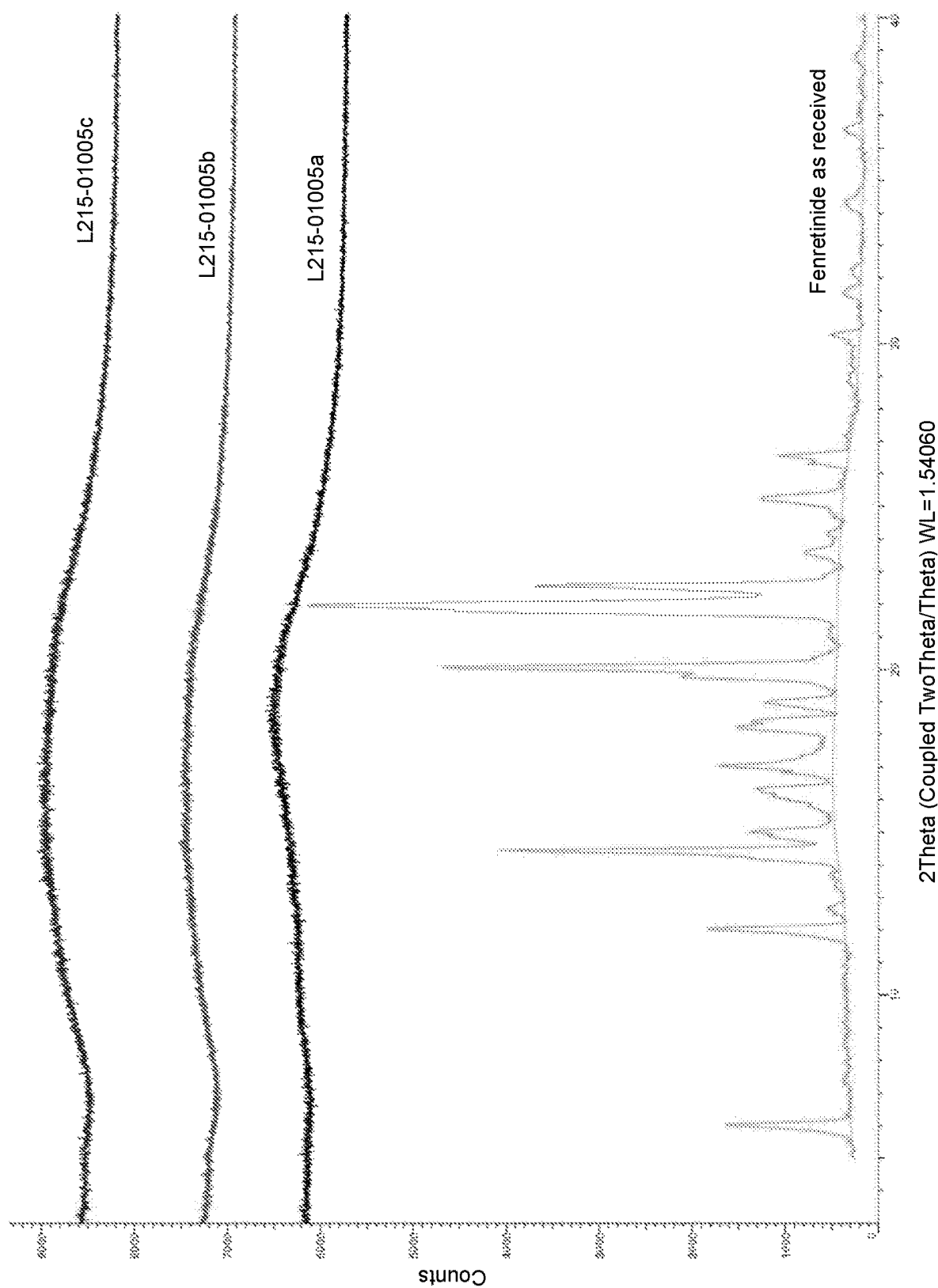
FIG. 1 shows XRPD Diffractograms of Fenretinide spray-dried intermediate (SDI) lots L215-01005a, b and c. Fenretinide lot C00324 (Fenretinide as received) was used as a reference.

In the studies described herein, the present inventors have developed a spray-dried amorphous solid dispersion of fenretinide that exhibits improved bioavailability, and more specifically higher fenretinide plasma $AUC_{(0-48)}$ and $C_{max}$ values in a rat model, relative to the current fenretinide corn-oil liquid suspension.

Accordingly, in an aspect, the present invention provides an amorphous solid dispersion comprising fenretinide or an analog thereof and at least one matrix polymer.

"Solid dispersion" as used herein refers to a solid material, in which a drug (fenretinide or an analog thereof) is dispersed in the solid matrix polymer. Such solid dispersions are also referred to in the art as "molecular dispersions" or "solid solutions" of the drug in the polymer.

Solid dispersions may be obtained by various techniques, for example fast evaporation, spray-drying, precipitation or melt extrusion (e.g., hot melt extrusion, HME). In an embodiment, the solid dispersion is obtained by spray-drying (spray-dried solid dispersion).

"Spray-dried solid dispersion" or "spray-dried dispersion" (SDD), as used herein means a solid dispersion produced using spray-drying technology. The term "spray-drying" is used conventionally and refers to processes involving breaking up liquid mixtures into small droplets (atomization) and rapidly removing solvent from the mixture in a container (spray-drying apparatus), in which there is a strong driving force for evaporation of solvent from the droplets. Spray-drying processes and spray-drying equipment or apparatus are described generally in for example Perry's Chemical Engineers' Handbook (Eighth Edition 2007). More details on spray-drying processes and equipment are reviewed by Marshall, "Atomization and Spray- Drying," 50 Chem. Eng. Prog. Monogr. Series 2 (1954), and Masters, Spray Drying Handbook (Fifth Edition 1991). The strong driving force for solvent evaporation is generally provided by maintaining the partial pressure of solvent in the spray-drying apparatus well below the vapor pressure of the solvent at the temperature of the drying droplets. This is accomplished by (1) maintaining the pressure in the spray-drying apparatus at a partial vacuum (e.g., 0.01 to 0.50 atm); or (2) mixing the liquid droplets with a warm drying gas; or (3) both (1) and (2). In addition, at least a portion of the heat required for evaporation of solvent may be provided by heating the spray solution. Spray-drying processes and apparatus suitable for use in the present invention include those disclosed in U.S. Pat. Nos. 7,780,988 and 7,887,840.

In an embodiment, at least a major portion of the fenretinide or analog thereof in the dispersion is amorphous. As used herein, the term "a major portion" of the fenretinide or analog thereof means that more than 50% of the fenretinide or analog thereof (by weight) in the dispersion is in the amorphous form, as opposed to the crystalline form. In embodiments, at least 55, 60, 65, 70, 75, 80, 85, 90% or 95% of the fenretinide or analog thereof (by weight) in the dispersion is in the amorphous form. By "amorphous" is meant that the fenretinide or analog thereof is in a non-crystalline state. Preferably, the fenretinide or analog thereof in the dispersion is "substantially amorphous", meaning that the amount of the fenretinide or analog thereof in crystalline form does not exceed about 25%, in further embodiments does not exceed about 20%, 15% or 10%. More preferably, the fenretinide or analog thereof in the dispersion is "almost completely amorphous," meaning that the amount of fenretinide or analog thereof in the crystalline form does not exceed about 10%. In a further embodiment, no recognizable characteristic crystalline fenretinide or fenretinide analog peaks are present in an X-ray powder diffraction pattern of the material. Amounts of crystalline drug may be measured by Powder X-Ray Diffraction (PXRD) analysis, Scanning Electron Microscope (SEM) analysis, Differential Scanning calorimetry (DSC) or any other standard quantitative measurement known in the art.

Examples of "matrix polymers", also referred to in the field as "concentration-enhancing polymers" or "dispersion polymers", which may be suitable for use in the present invention, are discussed in detail in for example U.S. Pat. Nos. 7,780,988 and 7,887,840. The matrix polymer can be any pharmaceutically acceptable polymer that once coprocessed with fenretinide or an analog thereof, functions to maintain the fenretinide/fenretinide analog in amorphous form.

Examples of polymers that may be suitable for use with the present invention comprise non-ionizable (neutral) non-cellulosic polymers. Exemplary polymers include: vinyl polymers and copolymers having at least one substituent selected from hydroxyl, alkylacyloxy, and cyclicamido; polyvinyl alcohols that have at least a portion of their repeat units in the unhydrolyzed (vinyl acetate) form; polyvinyl alcohol polyvinyl acetate copolymers; polyvinyl pyrrolidone; and polyethylene polyvinyl alcohol copolymers; and polyoxyethylene-polyoxypropylene copolymers.

Other examples of polymers that may be suitable for use with the present invention comprise ionizable non-cellulosic polymers. Exemplary polymers include: carboxylic acid-functionalized vinyl polymers, such as the carboxylic acid functionalized polymethacrylates and carboxylic acid functionalized polyacrylates such as the EUDRAGIT® series; amine-functionalized polyacrylates and polymethacrylates; proteins such as gelatin and albumin; and carboxylic acid functionalized starches such as starch glycolate.

Other examples polymers that may be suitable for use with the present invention comprise nonionizable cellulosic polymers that may be used as the polymer include: hydroxypropyl methyl cellulose acetate, hydroxypropyl methyl cellulose (HPMC), hydroxypropyl cellulose, methyl cellulose, hydroxyethyl methyl cellulose, hydroxyethyl cellulose acetate, hydroxyethyl ethyl cellulose, and the like.

While specific polymers have been discussed as being suitable for use in the dispersions formable by the present invention, blends of such polymers may also be suitable. Thus, the term "matrix polymer" is intended to include blends of polymers in addition to a single species of polymer.

In an embodiment, the matrix polymer comprises polyvinylpyrrolidone. In another embodiment, the matrix polymer is a polyvinylpyrrolidone, for example polymers sold under the trade-name Plasdone® (povidones), polyvinylpyrrolidone K12, polyvinylpyrrolidone K17, polyvinylpyrrolidone K25, polyvinylpyrrolidone K30 or polyvinylpyrrolidone K90.

In an embodiment, the ratio of fenretinide or analog thereof/matrix polymer is from about 1:5 to about 5:1, in further embodiments about 1:4 to about 4:1, about 1:3 to about 3:1, about 1:2 to about 2:1 or about 1.5:1 to about 1:1.5, by weight. In an embodiment, the solid dispersion comprises between about 30 to about 50% of fenretinide or analog thereof, and between about 50 to about 70% of matrix polymer. In another embodiment, the solid dispersion comprises between about 40% of fenretinide or analog thereof, and about 60% of matrix polymer, by weight.

In an embodiment, the solid dispersion comprises one or more additives. Additives that may be suitable for use with the present invention comprise antioxidant agents. Exemplary antioxidants include: L-ascorbic acid (vitamin C), propyl gallate, sodium sulfite, sodium metabisulfite, sodium bisulfite, thioglycerol, thioglycollic acid, tocopherols and tocotrienols, butylated hydroxyanisole (BHA), butylated hydroxytoluene (BHT) or any combination thereof. In an embodiment, the matrix polymer or solid dispersion comprises BHA and/or BHT as antioxidant agent(s). In an embodiment, the matrix polymer or solid dispersion comprises BHA and BHT as antioxidant agents. In an embodiment, the matrix polymer comprises L-ascorbic acid as antioxidant agent. In an embodiment, the antioxidant agent(s) is/are present in an amount of about 0.01% to about 5%, in further embodiments in an amount of about 0.1% to about 5%, about 0.2% to about 4%, 0.5% to about 3% or 0.5% to about 2%.

Fenretinide (all-trans-N-(4-hydroxyphenyl) retinamide; also referred to as 4-HPR, retinoic acid p-hydroxyanilide), which has CAS registry number 65646-68-6, is a synthetic retinoid of the following formula:

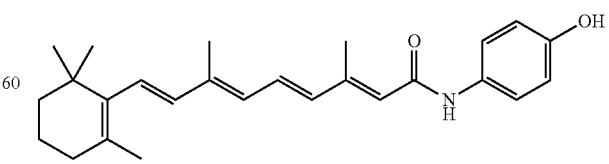

Functional analogs (and/or metabolites) of fenretinide (i.e. which exhibit the same biological activity as fenretinide) may also be used in the present invention. As used herein, a "fenretinide analog" or "fenretinide analog/metabolite" refers to a compound that shares certain chemical structural features with fenretinide but at the same time comprises one or more modifications thereto, and which exhibits similar biological activity as fenretinide (but may exhibit such activity to a different extent). Examples of analogs or analogs/metabolites of fenretinide that may be used include, but are not limited to, 4-oxo-N-(4-hydroxyphenyl)retinamide (4-oxo-4-HPR), N-(4-methoxyphenyl)retinamide (4-MPR), 4-Hydroxybenzylretinone, C-glycoside and arylamide analogues of N-(4-hydroxyphenyl)retinamide-O-glucuronide, including but not limited to 4-(retinamido)phenyl-C-glucuronide, 4-(retinamido)phenyl-C-glucoside, 4-(retinamido)benzyl-C-xyloside; and retinoyl β-glucuronide analogues such as, for example, 1-(β-D-glucopyranosyl) retinamide, 1-(D-glucopyranosyluronosyl) retinamide and bexarotene, described in WO 07/136636, U.S. Patent Application No. 2006/0264514, U.S. Pat. Nos. 5,516,792, 5,663,377, 5,599,953, 5,574,177, Anding et al. (2007) *Cancer Res.* 67: 6270-6277 and Bhatnagar et al. (1991) *Biochem. Pharmacol.* 41: 1471-7. In an embodiment, the fenretinide/fenretinide analog is represented by formula I

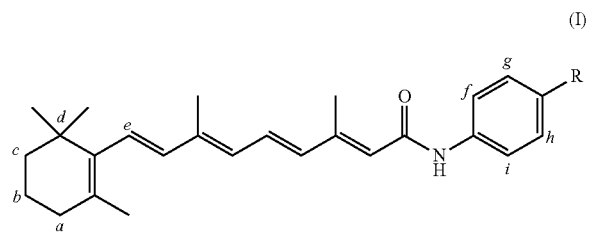

(I)

R is OH, COOH, CH$_2$OH, CH$_2$CH$_2$OH, or CH$_2$COOH;

carbons a-d and f-i are optionally substituted with one or more groups selected from CH$_3$, OH, COOH, (CH$_3$)$_2$ and CH$_2$OH, or any combination thereof, and carbon e is optionally substituted with a C$_1$-C$_3$ alkyl group that is optionally substituted with CH$_3$ and/or OH.

In an embodiment, the solid dispersion comprises fenretinide or a pharmaceutically acceptable salt thereof. In a further embodiment, the solid dispersion comprises fenretinide.

Preparation of Solid Dispersions

Dispersions of the fenretinide or an analog thereof and matrix polymer may be made via any process/technique that results in the fenretinide or analog thereof (preferably at least a major portion, i.e., more than 50%) being in the amorphous state of the fenretinide or analog thereof being in the amorphous state. Examples of such processes include fast evaporation, spray-drying, precipitation or melt extrusion (e.g., hot melt extrusion, HME). In an embodiment, the solid dispersion is made by spray-drying.

Spray-drying processes and spray-drying equipment are described generally in for example Perry's Chemical Engineers' Handbook (Eighth Edition 2007), Marshall, "Atomization and Spray-Drying," 50 Chem. Eng. Prog. Monogr. Series 2 (1954), and Masters, Spray Drying Handbook (Fifth Edition 1991).

The dispersions generally have their maximum bioavailability and stability when the drug (fenretinide or analog thereof) is dispersed in the matrix polymer such that it is substantially amorphous and substantially homogeneously distributed throughout the polymer. In general, as the degree of homogeneity of the dispersion increases, the enhancement in the aqueous concentration of the fenretinide or analog thereof and relative bioavailability increases as well. Thus, most preferred are dispersions having a single glass transition temperature, which indicates a high degree of homogeneity.

In the spray-drying process, the fenretinide or analog thereof and one or more matrix polymers are dissolved in a common solvent. "Common" here means that the solvent, which can be a mixture of compounds, will dissolve the fenretinide or analog thereof and the polymer(s). An antioxidant or a combination thereof, such as L-ascorbic acid, BHA and/or BHT, may be added to the mixture, for example to stabilize the chemical integrity of fenretinide against degradation by oxidation. After both the fenretinide or analog thereof and the polymer have been dissolved, the solvent is rapidly removed by evaporation in the spray-drying apparatus, resulting in the formation of a substantially homogeneous, amorphous solid dispersion. In such substantially homogeneous dispersions, the fenretinide or analog thereof is dispersed as homogeneously as possible throughout the polymer and can be thought of as a solid solution of fenretinide or analog thereof dispersed in the polymer.

The solvent is removed by the spray-drying process. The term spray-drying is used conventionally and broadly refers to processes involving breaking up liquid mixtures into small droplets (atomization) and rapidly removing solvent from the mixture in a spray-drying apparatus where there is a strong driving force for evaporation of solvent from the droplets. Such a strong driving force for solvent evaporation is generally provided by maintaining the partial pressure of solvent in the spray-drying apparatus well below the vapor pressure of the solvent at the temperature of the drying droplets. This is accomplished for example by either (1) maintaining the pressure in the spray-drying apparatus at a partial vacuum (e.g., 0.01 to 0.50 atm); (2) mixing the liquid droplets with a warm drying gas; or (3) both (1) and (2). In addition, at least a portion of the heat required for evaporation of solvent may be provided by heating the spray solution.

Solvents suitable for spray-drying can be any organic compound in which the fenretinide or analog thereof and matrix polymer are mutually soluble. Preferably, the solvent is also volatile with a boiling point of 150° C. or less. In addition, the solvent should preferably have relatively low toxicity and be removed from the dispersion to a level that is acceptable according to The International Committee on Harmonization (ICH) guidelines. Removal of solvent to this level may require a processing step such as tray-drying or secondary drying subsequent to the spray-drying process. Examples of solvents include alcohols such as methanol, ethanol, n-propanol, isopropanol, and butanol; ketones such as acetone, methyl ethyl ketone and methyl isobutyl ketone; esters such as ethyl acetate and propylacetate; and various other solvents such as dichloromethane, acetonitrile, methylene chloride, toluene, and 1,1,1-trichloroethane. Lower volatility solvents such as dimethylacetamide or dimethylsulfoxide can also be used. Mixtures of solvents can also be used, as can mixtures with water as long as the polymer and fenretinide or analog thereof are sufficiently soluble to make the spray-drying process practicable. In an embodiment, the solvent comprises dichloromethane, in a further embodiment the solvent is 100% dichloromethane.

The composition of the solvent-bearing feed will depend on the desired ratio of drug-to-polymer in the dispersion and the solubility of the fenretinide or analog thereof and polymer in the solvent. Generally, it is desirable to use as high a combined drug and polymer concentration in the solvent-bearing feed as possible, provided the drug and polymer are dissolved in the solvent, to reduce the total amount of solvent that must be removed to form the amorphous solid dispersion. Thus, the solvent-bearing feed will generally have a combined drug and polymer concentration of at least about 0.1 wt %, preferably at least about 1 wt %, and more preferably at least about 10 wt %. However, solvent-bearing feeds with lower combined drug and polymer concentrations can be used to form suitable amorphous solid dispersions.

The solvent-bearing feed comprising the drug and polymer is atomized through a pressure nozzle. By "pressure nozzle" is meant an atomizing means that produces droplets with an average droplet diameter of 50 μm or larger, with less than about 10 vol % of the droplets having a size less than about 10 μm. Generally, an appropriately sized and designed pressure nozzle is one that will produce droplets within this size range when the spray solution is pumped through the nozzle at the desired rate.

In the studies described herein, the solvent was evaporated using a Model GA32 Yamato® Lab Spray Dryer with the following operating parameters: 1.2 mm nozzle; about 9-15 g/min feed rate; 1.5 kg/cm$^2$ atomization air, and 0.35-0.55 m$^3$/min air flow. The inlet temperature was adjusted according to the solvent system to maintain an outlet temperature between 50-65° C. Hence, an inlet temperature of 100, 85 and 70° C. was used for the lots L215-01009A, 009B and 009C, respectively.

In many cases, the solvent-bearing feed is delivered to the atomizing means under pressure. The pressure required is determined by the design of the atomizer, the size of the nozzle orifice, the viscosity and other characteristics of the solvent-bearing feed, and the desired droplet size and size distribution. Generally, feed pressures may range from 1 to 200 atm (about 0.1 to about 20 MPa) or more.

The temperature and feed rate of the drying gas is chosen so that sufficient heat for drying the solvent-bearing feed is delivered to the drying chamber, while allowing sufficient residence time for the droplets to solidify before they impinge on the walls of the spray-drying apparatus. Generally, the higher the feed rate of the solvent-bearing feed, the higher the temperature and/or flow rate of the drying gas. Typically, the temperature of the drying gas at the inlet to the spray dryer will be at least about 60° C. and less than about 300° C., for example between about 60 to about 100° C. In an embodiment, the inlet temperature may be adjusted according to the solvent system to maintain an outlet temperature between about 30 to about 80° C., for example about 50-65° C. In an embodiment, the feed rate is typically at least about 0.1 ml/min, for example from about 1 ml/min to about 30 ml/min or from about 5 ml/min to about 20 ml/min.

Following solidification, the solid powder typically stays in the spray-drying chamber for about 5 to about 60 seconds, further evaporating solvent from the solid powder. The final solvent content of the solid dispersion as it exits the dryer should be low. Generally, the solvent content of the dispersion as it leaves the spray-drying chamber should be less than about 10 wt % and preferably less than about 3 wt % and most preferably less than about 1 wt %. As indicated above, a subsequent drying step, such as tray-drying, may be used to remove the solvent to this level.

In an embodiment, the spray-drying process is performed under the following operating parameters: 1.2 mm nozzle; about 9-15 g/min feed rate; about 1.5 kg/cm$^2$ atomization air, and about 0.35-0.55 m$^3$/min air flow, and the inlet temperature is adjusted to maintain an outlet temperature between about 50-65° C.

In another embodiment, the spray-drying process is performed under the following operating parameters: 1.2 mm nozzle; about 11-15 g/min feed rate; about 0.1-0.3 MPa atomization air, about 0.40 m$^3$/min air flow, inlet temperature of about 75° C.; outlet temperature of about 45 to about 48° C.

In another embodiment, the spray-drying process is performed under the following operating parameters: 1.2 mm nozzle; about 20 g/min feed rate; about 0.15 MPa atomization air, about 0.45-0.48 m$^3$/min air flow, inlet temperature of about 80° C.; outlet temperature of about 50 to about 54° C.

In certain embodiments, the material is processed though a secondary drying step. In some embodiments, a tray dryer is used for secondary drying. For example, in some embodiments, the dryer is a convention dryer. The secondary drying is performed for a sufficient period of time to meet product specifications. For example, in some embodiments, secondary drying occurs at about 30° C., 35° C., 40° C., 45° C., or 50° C. In certain embodiments, the drying time is at least about 1, 2, 3, 5, 6, 7, 8, 9, or 10 hours. In certain embodiments, the drying time is about 2 hours. In another embodiment, the secondary drying is performed under vacuum, for example at a pressure of about −40 to about −60 kPa, e.g., about −50 kPa.

Dosage Formulations

A "dosage form" or "dosage formulation" as used herein means a unit of administration of an active agent. Examples of dosage formulations include tablets, granules, capsules, injections, suspensions, liquids, emulsions, creams, ointments, suppositories, inhalable formulations, transdermal formulations, and the like. By "oral dosage formulation" is meant to include a unit dosage formulation for oral administration.

In some embodiments, the amorphous solid dispersion of the present invention is combined with one or more optional excipients to formulate the dispersion into suitable dosage formulations, such as tablets, capsules (e.g., hard gelatine capsules), strips, caplets, suspensions, powders for suspensions, cream, transdermal patches, depots, and the like.

The dispersion can also be added to other dosage form ingredients in a manner that advantageously does not substantially alter the activity of the fenretinide or analog thereof.

Generally, excipients such as surfactants, pH modifiers, fillers, matrix materials, complexing agents, solubilizers, lubricants, glidants, antioxidants, and so forth may be used for customary purposes and in typical amounts without adversely affecting the properties of the compositions. See for example, Remington's Pharmaceutical Sciences (18th ed. 1990).

The addition of pH modifiers such as acids, bases, or buffers may be beneficial, retarding the dissolution of the composition (e.g., acids such as citric acid or succinic acid when the matrix polymer is anionic) or, alternatively, enhancing the rate of dissolution of the composition (e.g., bases such as sodium acetate or amines when the matrix polymer is cationic).

Conventional matrix materials, complexing agents, solubilizers, fillers, diluents, disintegrating agents (disintegrants), preservatives, suspending agents or thickeners, anti-caking agents, or binders may also be added as part of the composition itself or added by granulation via wet or mechanical or other means. These materials may comprise up to 80 or 90 wt % of the composition.

Examples of matrix materials, fillers, or diluents include, without limitation, lactose, mannitol, xylitol, microcrystalline cellulose, dibasic calcium phosphate (anhydrous and dihydrate), starch, and any combination thereof.

Examples of disintegrants include, without limitation, sodium starch glycolate, sodium alginate, carboxy methyl cellulose sodium, methyl cellulose, and croscarmellose sodium, and crosslinked forms of polyvinyl pyrrolidone such as those sold under the trade name CROSPOVIDONE® (available from BASF Corporation), and any combination thereof.

Examples of binders include, without limitation, methyl cellulose, microcrystalline cellulose, starch, and gums such as guar gum, tragacanth, and any combination thereof.

Examples of lubricants include, without limitation, magnesium stearate, calcium stearate, stearic acid, and any combination thereof.

Examples of glidants include, without limitation, metal silicates, silicon dioxides, higher fatty acid metal salts, metal oxides, alkaline earth metal salts, and metal hydroxides. Examples of preservatives include, without limitation, sulfites (an antioxidant), benzalkonium chloride, methyl paraben, propyl paraben, benzyl alcohol, sodium benzoate, and any combination thereof.

Examples of suspending agents or thickeners, without limitation, include xanthan gum, starch, guar gum, sodium alginate, carboxymethyl cellulose, sodium carboxymethyl cellulose, methyl cellulose, hydroxypropyl methyl cellulose, polyacrylic acid, silica gel, aluminum silicate, magnesium silicate, titanium dioxide, and any combination thereof.

Examples of anti-caking agents or fillers, without limitation, include silicon oxide, lactose, and any combination thereof.

Examples of solubilizers include, without limitation, ethanol, propylene glycol, polyethylene glycol, and any combination thereof.

Examples of antioxidants include, without limitation, phenolic-based antioxidants such as butylated hydroxyanisole (BHA), butylated hydroxytoluene (BHT), tert-butylhydroquinone (TBHQ), 4-hydroxymethyl-2,6-di-tert-butylphenol (HMBP), 2,4,5-trihydroxy-butyrophenone (THBP), propyl gallate (PG), triamyl gallate, gallic acid (GA), α-Tocopherol (vitamin E), tocopherol acetate, reducing agents such as L-ascorbic acid (vitamin C), L-ascorbyl palmitate, L-ascorbyl stearate, thioglycolic acid (TGA), ascorbyl palmitate (ASP), sulphite-based antioxidants such as sodium sulphite, sodium metabisulphite, sodium bisulphite and thioglycerol and other agents such as disodium ethylenediamine tetraacetate (EDTA), sodium pyrophosphate, sodium metaphosphate, methionine, erythorbic acid and lecithin, and any combination thereof. In an embodiment, the formulation comprises a combination of antioxidants. In an embodiment, the formulation comprises a combination of BHA and BHT. In an embodiment, the formulation comprises ascorbic acid.

One other class of excipients is surfactants, optionally present from about 0 to about 10 wt %. Suitable surfactants include, without limitation, fatty acid and alkyl sulfonates; commercial surfactants such as benzalkonium chloride (HYAMINE® 1622, available from Lonza, Inc., Fairlawn, N.J.); dioctyl sodium sulfosuccinate (DOCUSATE SODIUM, available from Mallinckrodt Spec. Chem., St. Louis, Mo.); polyoxyethylene sorbitan fatty acid esters (TWEEN®, available from ICI Americas Inc., Wilmington, Del.; LIPOSORB® 0-20, available from Lipochem Inc., Patterson N.J.; CAPMUL.™. POE-0, available from Abitec Corp., Janesville, Wis.); and natural surfactants such as sodium taurocholic acid, 1-palmitoyl-2-oleoyl-sn-glycero-3-phosphocholine, lecithin, and other phospholipids and mono- and diglycerides, and any combination thereof. Such materials can be employed to increase the rate of dissolution by, for example, facilitating wetting, or otherwise increase the rate of drug release from the dosage form.

Other conventional excipients, including pigments, lubricants, flavorants, humectants, solution retarding agents, absorption accelerators, wetting agents, absorbents, and other ones well-known in the art, may be employed in the compositions of this invention. For example, excipients such as pigments, lubricants, flavorants, and so forth may be used for customary purposes and in typical amounts without adversely affecting the properties of the compositions.

Other components commonly added to pharmaceutical compositions include, e.g., inorganic salts such as sodium chloride, potassium chloride, calcium chloride, sodium phosphate, potassium phosphate, sodium bicarbonate; and organic salts such as sodium citrate, potassium citrate, sodium acetate, etc.

In an embodiment, the amorphous solid dispersion of the present invention is combined with a disintegrant, for example a cross-linked sodium carboxymethylcellulose e.g., croscarmellose (Solutab®). Other examples of disintegrants include corn starch, potato starch, sodium carboxymethylcellulose, sodium starch glycolate, sodium croscarmellose, crospovidone, and any combination thereof. In an embodiment, the disintegrant is present in an amount from about 2 to about 10% by weight, for example from about 3 to about 8% or about 4 to about 6% by weight.

In an embodiment, the amorphous solid dispersion of the present invention is combined with a lubricant, for example magnesium stearate. Other examples of lubricants include talc, silicon dioxide, stearic acid, and sodium stearyl fumarate. In an embodiment, the lubricant is present in an amount from about 0.5 to about 2% by weight, for example from about 0.8 to about 1.2% or about 1% by weight.

In an embodiment, the amorphous solid dispersion of the present invention is combined with a filler or diluent, for example microcrystalline cellulose (Avicel®, such as Avicel®PH-102) and/or calcium hydrogen phosphate dehydrate (Encompress®). Other examples of fillers or diluents include crystalline cellulose, cellulose derivatives, acacia, corn starch, lactose, mannitol, sugars, calcium phosphate, calcium carbonate, gelatins, and any combination thereof. In an embodiment, the filler or diluent is present in an amount from about 20 to about 45% by weight, for example from about 30% to about 40% by weight, e.g., about 35%.

The amorphous solid dispersion of the present invention may be used in a wide variety of dosage forms for administration by a wide variety of routes, including, but not limited to, oral, nasal, rectal, vaginal, transdermal, buccal, subcutaneous, intravenous, and pulmonary.

In certain embodiments, the amorphous solid dispersion as disclosed herein is formulated as an oral dosage formulation. Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an elixir or syrup, or as pastilles (using an inert matrix, such as gelatin and glycerin, or sucrose and acacia), and the like, each containing a predetermined amount of an active ingredient. A composition may also be administered as a bolus, electuary, or paste. In an embodiment, the oral dosage formulation of the present invention is a tablet. A tablet may be made by compression or molding, optionally with one or more accessory ingredients. Compressed tablets may be prepared using binder, lubricant, inert diluent, preservative, disintegrant, surface-active or dispersing agent. Molded tablets may be made by molding in a suitable machine a mixture of the powdered inhibitor(s) moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner.

In some embodiments of the oral dosage formulation as disclosed herein, the amorphous solid dispersion is present in an amount of from about 10 to about 90%, about 20 to about 80%, about 30 to about 60% or about 45 to about 55% by weight, or another range within the values provided herein.

In an embodiment, the amorphous solid dispersion or the dosage formulation of the present invention results in fenretinide (or an analog thereof) plasma $AUC_{(0-48)}$ and/or $C_{max}$ values that are at least 1.5-times (in further embodiments at least 2-, 2.5-, 3-, or 4-times) higher relative to the normalized fenretinide plasma $AUC_{(0-48)}$ and/or $C_{max}$ values exhibited by a corresponding fenretinide corn oil liquid suspension, e.g., $AUC_{(0-48)}$ and/or $C_{max}$ values measured in an animal model, such as rats.

Uses of the Amorphous Solid Dispersion and the Dosage Formulation

The amorphous solid dispersion and the dosage formulation as disclosed herein may be used for preventing or treating (e.g., alleviating) one or more symptoms and/or severity of any disease/condition that is subject to prevention or treatment by administering fenretinide or a fenretinide analog. For example, conditions that may be prevented or treated by the dispersion or dosage form of the present invention include hyperproliferative disorders, malignancies and neoplasms (e.g., solid tumors, cancers), such as those disclosed in WO 2002/058689. Such hyperproliferative disorders, malignancies, and neoplasms include, but are not limited to, malignant disorders such as breast cancers; osteosarcomas; angiosarcomas; fibrosarcomas and other sarcomas (e.g., Ewing's sarcoma, Kaposi's sarcoma); leukemias; lymphomas (e.g., non-Hodgkin's lymphoma); sinus tumors; ovarian, uretal, bladder, prostate and other genitourinary cancers; colon esophageal and stomach cancers and other gastrointestinal cancers; lung cancers (non-small cell lung cancers); myelomas; pancreatic cancers; liver cancers; kidney cancers; endocrine cancers; skin cancers (e.g., melanoma, basal cell carcinoma); head and neck carcinoma and brain or central and peripheral nervous (CNS) system tumors, malignant or benign, including gliomas and neuroblastomas.

Examples of diseases/conditions that are subject to prevention or treatment by administering fenretinide include also premalignant and non-neoplastic or non-malignant hyperproliferative disorders such as myelodysplastic disorders; cervical carcinoma-in-situ; familial intestinal polyposes such as Gardner syndrome; oral leukoplakias; histiocytoses; keloids; hemangiomas; hyperproliferative arterial stenosis, inflammatory arthritis; hyperkeratoses and papulosquamous eruptions including arthritis. Also included are viral-induced hyperproliferative diseases such as warts and Epstein-Barr virus (EBV)-induced disease (i.e., infectious mononucleosis), scar formation, and the like.

Other diseases/conditions may be prevented or treated by the amorphous solid dispersion or dosage form of the present invention include those discussed in PCT Patent Publication Nos. WO 2005/084657, WO 2007/068116 and WO 2009/103106, for example conditions associated with inflammation of the respiratory tract such as cystic fibrosis, allergic asthma, a disease or condition associated with a lipid or fatty acid imbalance (DHA/AA imbalance), including infections (e.g., opportunistic infections) of the respiratory tract (e.g., *Haemophilus influenzae, Pseudomonas aeruginosa, Streptococcus pneumoniae, Streptococcus pyogenes, Mycobacterium tuberculosis, Candida albicans* or *Aspergillus fumigatus*) and bone diseases (osteopenia or osteoporosis), as well as neural diseases or conditions associated with neuroinflammation and/or microglial activation, such as neural injury (e.g., spinal cord injury) and neurodegenerative diseases (e.g., Amyotrophic Lateral Sclerosis (ALS), Parkinson's disease, and Huntington's disease). Other diseases/conditions may be prevented or treated by the spray-dried amorphous solid dispersion or dosage form of the present invention include those discussed in PCT publication No. WO 2009/114136, for example conditions associated with HIV/AIDS, allergic encephalomyelitis, ichthyosis, and metabolic conditions such as diabetes and obesity, as well as ophthalmic conditions described in PCT publication No. WO2012078525, such as various macular degenerations and dystrophies, including but not limited to dry-form age-related macular degeneration (dry AMD) and Stargardt Disease.

Other diseases/conditions may be prevented or treated by the amorphous solid dispersion or dosage form of the present invention include those discussed in PCT publication No. WO 2014/169355, such as viral infections caused by flaviviruses, such as dengue virus, yellow fever virus, West Nile virus or Japanese encephalitis virus or infections caused by Chikungunya virus (CHIKV).

It is also contemplated that the solid dispersion and the dosage formulation of the instant invention (or combinations thereof) may be used alone or in combination with (i.e., administered before, after, or simultaneously with) other therapeutics and/or nutraceuticals and/or nutritional supplements, currently used to prevent and/or treat the above-noted diseases and/or conditions (e.g., cancers, cystic fibrosis, spinal cord injury or neurodegenerative diseases/disorders, metabolic diseases/conditions, ophthalmic conditions) or their associated effects (e.g., pain). An example for such combination could include fenretinide and docosahexaenoic acid (DHA) for the prevention and/or the treatment of disease or condition associated with AA/DHA lipid/fatty acid imbalance, such as cystic fibrosis, inflammation, opportunistic infection, neuroinflammatory and neurodegenerative diseases.

MODE(S) FOR CARRYING OUT THE INVENTION

The present invention is illustrated in further detail by the following non-limiting examples.

Example 1: Materials & Methods

Formulation Approaches
Reagents

Table 1 provides a description of the materials used in this study. All materials were stored at room temperature (RT).

TABLE 1

Materials

| Material (Commercial Name) | Lot # | Supplier |
|---|---|---|
| Fenretinide | C00324 | Cedarburg |
| Lactose monohydrate (FastFlo ® 316) | C00301 | Foremost |
| Lactose monohydrate (Granulac ® 200) | L1020A4172 | Maggie |
| Lactose monohydrate (Tabletose ®-80) | C00125 | Meggle |
| Miorocrystalline cellulose (Avicel ® PH-102) | C00098 | FMC |
| Microcrystalline cellulose (Tabulose ®-101) | C00044 | Blanver |
| Pregelatinized maize starch (Starch 1500) | IN518955 | Colorcon |
| Calcium hydrogen phosphate dihydrate (Emcompress ®) | C00084 | JRS |
| Sodium lauryl sulfate (SLS) | C00038 | Stepanol WA-100 |
| Poloxamer ® 188 | C00261 | BASF |
| Craspovidone CL | | BASF |
| Microencapsulated polisorbate 80 (Sepitrap ® 80) | 18682656PO | SEPPIC |
| Croscarmellose sodium (Solutab ® Type A) | 249081 | Blanver |
| Colloidal silicon dioxide (Aerosil ® 200) | C00020 | Evonik |
| Magnesium stearate (Ligamed ® MF-2-V) | C00122 | Peter Graven |
| Lauroyl polyoxyl-32 glycerides (Gelucire ® 44/14) | C00124 | Gattefosse |
| Macrogol 15 hydroxystearate (Kolliphor ® HS 15) | 125008 | BASF |
| Polyethylene glycol 400 | 50383647G0 | A&C |
| Hypromellose (Vivapharm ® HPMC E5) | 20738568 | JRS |
| Povidone (Plasdone ® K-29/32) | 10056/10X | ISP |
| Povidone (Kollidon ® 30) | C00033 | BASF |
| Copovidone (Kollidon ® VA64) | C00286 | BASF |
| Dichloromethane (DCM) | 17250416K0 | EMD |
| | 53102 | |
| | 53130 | |
| Methanol (MeOH) | 53088 | EMD |
| Ethanol, anhydrous (EtOH) | E00515 | Commercial Alcohol |
| Hard gelatin capsules # 00 white opaque | 70934661/70502051 | Capsugel |
| Hard gelatin capsules # 00 orange opaque | C00159 | Capsugel |
| Hard gelatin capsules # 1 white opaque | C00023 | Capsugel |
| Hard gelatin capsules # 9 white opaque | 2757 | Capsugel |

Formulation Approaches

Dry blending. L215-01001 and 002 (Table 2) is a dry-blend powder formulation of Fenretinide (40%). First, all ingredients were screened with a 30 mesh-sieve and mixed without the lubricant using a V-blender at 25 rpm for 3 min. The lubricant was added and mixed for 2 min. The final blend was encapsulated for an equivalent of 5 and 100 mg Fenretinide/capsule.

TABLE 2

Dry Blending Formulation for Lots L215-01001 and 2

| Ingredients | L215-01001 | L215-01002 |
|---|---|---|
| | % w/w | |
| Fenretinide | 40.0 | |
| FastFlo ® 316 | 33.8 | |
| Avicel ® PH-102 | 11.2 | |
| Starch 1500 | 5.0 | — |
| Sepitrap ® 80 | 5.0 | — |
| Solutab ® Type A | 4.0 | — |
| SLS | — | 5.0 |

TABLE 2-continued

Dry Blending Formulation for Lots L215-01001 and 2

| Ingredients | L215-01001 | L215-01002 |
|---|---|---|
| | % w/w | |
| Poloxamer ® 188 | — | 5.0 |
| Crospovidone CL | — | 4.0 |
| Magnesium stearate | 1.0 | |
| Total: | 100.0 | |

Melt Granulation: L215-01003 (Table 3) was prepared by melt granulation method. Powdered ingredients were screened through 30-mesh sieve, mixed during 2 min using mortar/pestle and dispersed into molten Gelucire® at approximately 50° C. The mixture was homogenized using mortar and pestle. The mass was screened through a 20-mesh sieve to obtain uniform-sized granules. The lubricant was added and mixed for 2 min. The final blend was encapsulated for an equivalent of 5 mg (for PK testing in rats) and 100 mg Fenretinide/capsule.

TABLE 3

Melt Granulation Formulation for Lot L215-01003

| Ingredients | % w/w |
|---|---|
| Fenretinide | 40.0 |
| Gelucire ® 44/14 | 20.0 |
| Granulac ® 200 | 26.2 |
| Tabulose ®-101 | 8.8 |
| Croscarmellose sodium | 4.0 |
| Magnesium stearate | 1.0 |
| Total: | 100.0 |

Lipid-Based Dispersions: Lipid-based dispersions formulations (lots L215-01004a to 004c) are presented in Table 4. Fenretinide (40%) was dispersed in the in the molten carrier at 60° C. The mixture was vigorously mixed and encapsulated for an equivalent of 5 mg and 100 mg Fenretinide/capsule.

TABLE 4

Lipid-Based Dispersion Formulations for Lots L215-01004a to c

| Ingredients | L215-01004a | L215-01004b | L215-01004c |
|---|---|---|---|
| | | % w/w | |
| Fenretinide | | 40.0 | |
| Gelucire ® 44/14 | 60 | 40.0 | 20.0 |
| Polyethylene glycol 400 | — | 20.0 | 20.0 |
| Kolliphor ® HS 15 | — | — | 20.0 |
| Total: | | 100.0 | |

Solid Dispersions: Solid dispersions of Fenretinide (active pharmaceutical ingredient, API) were obtained by spray drying. The spray-drying solution was prepared by dissolving API/Polymer (8 g/12 g) in 400 ml of methanol/dichloromethane (50/50% v/v) system solvent. The solvent was evaporated using a Model GA32 Yamato® Lab Spray Dryer with the following operating parameters: 1.2 mm nozzle; about 18 ml/min feed rate; 70° C. inlet temperature; 31-40° C. outlet temperature; 1.5 kg/cm$^2$ atomization air, and 0.40 m$^3$/min air flow. The spray dried material was secondary dried for 2 hours at 40° C. and −50 kPa in an Isotemp® vacuum oven model 281 A. The Spray-Dried Intermediate (SDI) (lots L215-01005a to 005c, Table 5) were encapsulated for an equivalent of 5 and 100 mg Fenretinide/capsule.

TABLE 5

Solid Dispersions Formulations for Lots L215-01005a to c

| Ingredients | L215-01005a | L215-01005b | L215-01005c |
|---|---|---|---|
| | | % w/w | |
| Fenretinide | | 40.0 | |
| HPMC E5 | 60.0 | — | — |
| Plasdone ® K-29/32 | — | 60.0 | — |
| Kollidon ® VA64 | — | — | 60.0 |
| Total: | | 100.0 | |

Dry Granulation (DG) by Slugging: Before the preparation of prototype, a new batch of SDI was manufactured (lot L215-01006b, Table 6) according to the same process used for lot L005b. L215-01006b (Table 6): Spray drying process was conducted as described for lot L215-01005b.

TABLE 6

SDI Formulation for Lot L215-01006b

| Ingredients | % (w/w) | qty/batch |
|---|---|---|
| Fenretinide | 40.0 | 48.0 g |
| Plasdone ® K-29/32 | 60.0 | 72.0 g |
| Methanol/Dichloromethane (50:50 v/v) | NA | 1.50 L |
| Total: | 100.0 | 120.0 g |

NA: Evaporated during the process

Fenretinide prototype formulations were prepared by slugging using the spray-dried intermediate (SDI) material from lot L215-01006b.

L215-01007 (Table 7): The slugs (350-450 mg/12 mm/4-6 kp) were compressed using a Carver® (Model C) hydraulic hand press with 12 mm round standard concave tooling. The granules were obtained by screening through a 20-mesh sieve. The extragranular ingredients and granulated material were mixed for 2 minutes at 25 rpm. The lubricant was added and mixed for 2 additional minutes. The powders were encapsulated for an equivalent of 2.5 and 100 mg Fenretinide/capsule.

TABLE 7

Dry Granulation Prototype Formulations for Lots L215-01007a to c

| | Formulation | | | | | |
|---|---|---|---|---|---|---|
| | L215-01007a | | L215-01007b | | L215-01007c | |
| Ingredient name | % w/w | mg/unit | % w/w | mg/unit | % w/w | mg/unit |
| Intragranular ingredients | | | | | | |
| Fenretinide/Plasdone ® SDI (L215-01006b) | 50.0 | 6.3 | 50.0 | 6.3 | 50.0 | 6.3 |
| Croscarmellose | 2.5 | 0.3 | 2.5 | 0.3 | — | — |
| Magnesium stearate | 0.5 | 0.1 | 0.5 | 0.1 | 0.5 | 0.06 |
| Aerosil ®-200 | — | — | — | — | 0.1 | 0.01 |
| Extragranular ingredients | | | | | | |
| Avicel ®-102 | 22.0 | 2.8 | 28.0 | 3.5 | 22.0 | 2.8 |
| Tablettose-80 | 22.0 | 2.8 | — | — | 22.0 | 2.8 |
| Emcompress ® | — | — | 16.0 | 2.0 | — | — |
| Croscarmellose | 2.5 | 0.3 | 2.5 | 0.3 | 2.5 | 0.3 |
| Magnesium stearate | 0.5 | 0.1 | 0.5 | 0.1 | 0.5 | 0.1 |
| Total: | 100.0 | 12.5 | 100.0 | 12.5 | 100.0 | 12.5 |

L215-01008 (Table 8): The slugs (about 500 mg/9.0×21.5 mm/2-6 kp) were compressed using a Rotary tableting machine SVIAC PR6 with 9.00×21.50 mm capsule shape tooling. The granules were obtained by screening through a 20-mesh sieve. The extragranular ingredients and granulated material were mixed for 2 minutes at 25 rpm. The lubricant was added and mixed for 2 additional minutes. The final blend was encapsulated for an equivalent of 100 mg Fenretinide/capsule. These capsules were packaged in plastic bottles and stored at 5° C. pending further use. A placebo was prepared (L215-01008P) by dry blending and stored in powder form.

TABLE 8

Fenretinide 100 mg Capsule Formulation
Lot L215-01008 by Dry Granulation

| Ingredients | % w/w | mg/unit |
|---|---|---|
| Intragranular ingredients | | |
| Fenretinide/Plasdone ® SDI (L215-01006b) | 50.0 | 250.0 |
| Croscarmellose | 2.5 | 12.5 |
| Magnesium stearate | 0.5 | 2.5 |
| Extragranular ingredients | | |
| Avicel ®-102 | 28.0 | 140.0 |
| Emcompress ® | 16.0 | 80.0 |
| Croscarmellose | 2.5 | 12.5 |
| Magnesium stearate | 0.5 | 2.5 |
| Total: | 100.0 | 500.0 |

Solid Dispersion Improvement/Optimization
Solvent System Optimization

The solubility of Fenretinide/PVP K30 40/60% w/w mixtures was first visually assessed in various ratios of ethanol/dichloromethane. Thereafter, Spray Dryed Intermediates (SDIs) were produced from Fenretinide/PVP K30 40/60% w/w mixture solubilized at 7.5% w/v in ethanol/dichloromethane 90/10 v/v (L215-01009A), 50/50 v/v (L215-01009B) and 10/90 v/v (L215-01009C) systems for a total batch size of 15 g. The solvent was evaporated using Model GA32 Yamato® Lab Spray Dryer with the following operating parameters: 1.2 mm nozzle; about 9-15 g/min feed rate; 1.5 kg/cm$^2$ atomization air, and 0.35-0.55 m$^3$/min air flow. The inlet temperature was adjusted according to the solvent system to maintain an outlet temperature between 50-65° C. Hence, an inlet temperature of 100, 85 and 70° C. was used for the lots L215-01009A, 009B and 009C, respectively.

Solvent System Optimization

Successive amounts of Fenretinide and PVP K30 40/60% w/w were added in 200 ml of dichloromethane until saturation of the solution. At a total solid loading of 20% w/v (40 g), the addition of Fenretinide and PVP K30 was stopped due to the increase of the solution viscosity. The solution was spray dried (lot L215-01010) with the following process parameters: 11-15 g/min feed rate; 75° C. inlet temperature; 45-48° C. outlet temperature; 0.1-0.3 MPa atomization air, and 0.40 m$^3$/min air flow.

Scale-Up

Lot L215-01011 was prepared by dissolving 100 g Fenretinide and 150 g PVP K30 in 2000 ml of dichloromethane. The solution was spray dried with the following process parameters: about 20 g/min feed rate; 80° C. inlet temperature; 50-54° C. outlet temperature; 0.15 MPa atomization air, and 0.45-0.48 m$^3$/min air flow. At about each 1000 g of solution sprayed, the spray drying process was stopped and the SDI in the product vessel was collected. The spray dried material was secondary dried for 16 hours at RT and −15 inHg in an Isotemp® vacuum oven model 281A.

SDI/Excipient Direct Encapsulation

SDI/excipient blend lots L215-01012A and B (batch size of 125 and 150 capsules, Table 9) was encapsulated directly into 00 HGC using a semi-automatic Schaefer® STI-10 capsule filling machine. The SDI, Avicel®-102 and Emcompress® were mixed for 5 min at 25 rpm in a 1.0 qt V-blender. The blend was screened over a 600 µm sieve and returned into the V-blender. The croscarmellose, previously screened over 600 µm sieve, was added into the V-blender and mixed for 5 min at 25 rpm. Finally, magnesium stearate, previously screened over 600 µm sieve, was added into the V-blender and mixed for 2 min at 25 rpm. The capsule bodies were filled manually. For analysis purposes, a placebo formulation lot L215-01013P (Table 10) was prepared as described above for the lot L215-01012.

TABLE 9

Fenretinide 100 mg HGC Direct Encapsulation Formulation (Lots L215-01012A and 012B)

| Ingredients | L215-01012A | | L215-01012B | |
|---|---|---|---|---|
| | % w/w | mg/unit | % w/w | mg/unit |
| Fenretinide/PVP K30 SDI (L215-010011) | 50.0 | 250.0 | 55.55 | 250.0 |
| Avicel ®-102 | 17.65 | 75.0 | 17.78 | 80.0 |
| Emcompress ® | 17.65 | 75.0 | 20.0 | 90.0 |
| Croscarmellose | 4.9 | 20.75 | 5.67 | 25.5 |
| Magnesium stearate | 1.0 | 4.25 | 1.0 | 4.5 |
| Total: | 100.0 | 425.0 | 1.00 | 450.0 |

TABLE 10

Fenretinide Placebo HGC Direct Encapsulation Formulation (Lot L215-01013P)

| Ingredients | L215-01013P | |
|---|---|---|
| | % w/w | mg/unit |
| PVP K30 | 42.86 | 192.86 |
| Avicel ®-102 | 22.86 | 102.86 |
| Emcompress ® | 25.71 | 115.71 |
| Croscarmellose | 7.29 | 32.79 |
| Magnesium stearate | 1.29 | 5.79 |
| Total: | 100.0 | 450.0 |

Short Term Stability Study

The short term stability of formulation lot L215-01012B was initiated by putting samples into sealed HDPE bottle at 5° C., 25° C./60% RH and 40° C./75% RH. At each time point (0.5 and 1 month), the samples were evaluated in term of assay and related substance, moisture (Karl Fisher), crystal state (XRPD) and dissolution profile.

API, SDI and Prototypes Characterization

The API, SDI and prototypes produced during this study were characterized by evaluation the applicable following properties:

Assay and related substance;
Crystal state (X-ray powder diffraction, XRPD);
Differential scanning calorimetry (DSC);
Dissolution;
Residual solvent;
Scanning electron microscopy (SEM);
Thermogravimetric analysis (TGA); and
Viscosity Assay and Related Substance Fenretinide assay and related substance was quantified by HPLC using the following system:

HPLC System:
Equilibrate the HPLC column for at least 30 min before the run
Column: Inertsil® ODS-2, 250×4.6 mm, 5 µm
Column Temperature: 25° C.
Tray Temperature: 20° C.
Injection volume: 5 µL
Mobile Phase: A: TFA/H20 buffer pH 3.0: ACN 20:80; B:CAN (see gradient)
Flow: 2.0 mL/min
Detector wavelength: 360 nm
Run Time: 35 minutes
Retention Time: ~8 minutes (Fenretinide)
Sample Diluent: 80% Acetonitrile in water Gradient:

| Time (min.) | Mobile Phase A (%) | Mobile Phase B (%) |
|---|---|---|
| 0 | 100 | 0 |
| 12 | 100 | 0 |
| 20 | 0 | 100 |
| 25 | 0 | 100 |
| 25.1 | 100 | 0 |
| 35 | 100 | 0 |

Crystal State (X-Ray Powder Diffraction, XRPD) (USP <941>, US Pharmacopeia XXXIV, US Pharmacopeia Convention, Rockville, Md., 2011)

The crystal state was studied by X-Ray Diffraction (XRD) using a Bruker® D2 Phaser X-ray diffractometer with Lynxeye® detector, Cu Kα radiation (λ=1.5406 Å) at an increment of 0.04° 2θ with a 0.1 s step time (scanning rate of 24 2θ/min) over a range of 5-40° 2θ, a 1.0 mm opening slit and a 8 mm detector window. The samples (about 0.2 g) were analysed using a low volume sample holder kept under a constant rotation of 15 rpm during the analysis.

Differential Scanning Calorimetry (DSC) (USP <891>, US Pharmacopeia XXXIV, US Pharmacopeia Convention, Rockville, Md., 2011)

Differential Scanning calorimetry (DSC) analysis was completed with a TA Instrument Q20 DSC. The sample was first equilibrated at 20° C. for 5 min and heated at 10° C./min up to 250° C. under a nitrogen purge of 50 ml/min. The sample was analysed using a TA Instrument Tzero® hermetic aluminium pan.

Dissolution

Fenretinide dissolution profile form the prototype was characterised using USP apparatus II (paddle, 100 rpm, 37° C.) and HPLC using the systems below. At 60 min a 200 rpm ramp was applied for 15 min. The dissolution medium (900 mL) was 0.1N HCl with 2% SDS, pH 6.8 phosphate buffer with 2% SLS or pH 8.0 phosphate buffer with 2% SDS.

Dissolution System:
Use a calibrated bath set to these conditions with 6 vessels:
Medium: 900 ml
Bath Temperature: 37.0±0.5° C.
Apparatus: USP apparatus II (Paddles)
Speed: 100 rpm
Sampling times: 10, 20, 30, 60 minutes+ramp at 200 rpm for 15 minutes
Sampling volume: 1 ml
Filter: 45 μm Polyethylene
HPLC System:
Column: Inertsil® ODS-2, 250×4.6 mm, 5 μm
Column Temperature: 25° C.
Tray Temperature: 20° C.
Injection volume: 5 μL
Mobile Phase: Isocratic 30% Mobile phase A/70% mobile phase B
Flow: 2.0 mL/min
Detector wavelength: 360 nm
Run Time: 6 minutes
Retention Time: ~4 minutes (Fenretinide)

Residual Solvent

The amount of residual solvent in Fenretinide SDI or prototype was quantified by gas chromatography using the system below (based on USP <467> Residual Solvents).

Equipment:
Column: DB-624, 30 m×0.32 mm, 1.8 μm film thickness.
Mode: Constant flow. Column flow: 3.0 mL/min (linear velocity of 44 cm/s).
Oven program: Initial temperature: 35° C. Initial Hold time: 5.0 minutes. Ramp Program #1: 30° C./min. up to 260° C., hold time 15 min.
Detector (FID): Temperature: 260° C. Hydrogen flow: 30 mL/min. Air flow: 300 mL/min. Makeup: Nitrogen at 30 mL/min.
Inlet (Split/Splitless): Mode: Splitless; Vent flow of 224 mL/min @ 0.10 min. Temperature: 260° C. Carrier Gas: Helium. Gas saver parameters: 15.0 mL/min after 2.00 min.
Injector Parameters: Rinse Solvents: A=DMSO; B=Methylpyrrolidone. Pre-injection wash: 3× Solvent Band 2× Sample. Sample Injection: 3× Syringe pumps then 1 μL Injection volume. Post-injection wash: 10× Solvent A and 10× Solvent B.

Scanning Electron Microscopy (SEM)

The morphology and surface characteristics of particles were examined at various magnifications with a JEOL JSM-6010LV InTouchScope® scanning electron microscope using a backscattered electron (BSE) or a secondary electron (SEI) detector. The images were obtained with accelerating voltages between 1.5 and 20.0 kV under a pressure of 60 to 70 Pa. Samples were placed on metallic stubs using double-sided carbon conductive tape.

Thermogravimetric Analysis (TGA) (USP <891>, US Pharmacopeia)(XXIV, US Pharmacopeia Convention, Rockville, Md., 2011)

Thermogravimetric analysis was performed using a TA Instrument Q50 thermogravimetric analyzer at scanning speed of 10° C./min over a temperature range of 20 to 500° C. The samples were heated in a platinum open crucible in nitrogen atmosphere (60 ml/min) and the mass loss as a function of temperature was recorded.

Viscosity

The viscosity of the solution was determined at RT using a Brookfield® DV-II+viscometer at 100 rpm.

Example 2: Encapsulation

Fenretinide 2.5 and 5.0 mg prototype formulations were intended for an animal pharmacokinetics (PK) study. The capsules were filled manually using filling funnel/stand and tamper into capsules size #9. Capsules with 100 mg Fenretinide were filled manually in capsules size #1 except lots 005a to 005c and 007a to 007c which were encapsulated in 00 capsules. Weight variations below 3% RSD were observed, so adequate drug content uniformity is expected.

Example 3: Analytical Testing

Fenretinide 100 mg prototype formulations were tested by assay, related substances and dissolution rates. The results obtained as well as sample preparations are shown below.

According the results obtained for neat API, the total amount of impurities seems to be related to the preparations of the samples during manufacturing and analytical testing (Table 11). Different levels of impurities were observed for samples from a same lot of API depending on the extraction solvent and for two lots of API with the same solvent. The lowest related substances were observed for API lot 1 using methanol as solvent.

TABLE 11

| | Impurities Observed for the API | | | | | |
|---|---|---|---|---|---|---|
| Sample | API - Lot 1 | | API - Lot 1 replicate | | | |
| Sample preparation | Water to dissolve capsule, then complete to volume with methanol (MeOH) Final ratio 20% Water:80% MeOH | | Water to dissolve capsule, then complete to volume with acetonitrile (ACN) Final ratio 20% Water:80% ACN | | Water to dissolve capsule, then complete to volume with acetonitrite (ACN) Final ratio 20% Water:80% ACN | |
| | RRT | % Area | RRT | % Area | RRT | % Area |
| Related Substances (% area) | 0.22 | 0.01 | 0.25 | 0.01 | 0.25 | 0.01 |
| | 0.26 | 0.01 | 0.27 | 0.07 | 0.27 | 0.08 |
| | 0.28 | 0.07 | 0.72 | 0.18 | 0.49 | 0.02 |
| | 0.49 | 0.02 | 0.90 | 0.14 | 0.72 | 0.19 |
| | 0.72 | 0.18 | 0.93 | 0.29 | 0.90 | 0.20 |
| | 0.93 | 0.05 | Total | 0.70 | 0.93 | 0.40 |
| | Total | 0.35 | | | Total | 0.89 |

Formulation Lots L215-01001 to 005c

Assay and related substances results were obtained using two different sample preparation methods.

The results obtained for the formulations 001 to 004 showed remarkable difference depending on sample preparation. For all capsule formulations the better results were obtained using 20% Water: 80% ACN as solvent system (Table 12). Moreover, formulations and API (Table 11) showed similar impurities profiles.

Assay of NMT 50% were obtained for all Gelucire® 44/14 containing formulations (lots 003 and 004 a, b and c). Using 20% Water: 80% ACN as solvent system the total amount of related substances was between 0.68 and 0.85% (Tables 13 and 14).

For solid dispersion formulations (lots 005a, b and c (Table 17)) assay of about 98% and related substances of about 1% were obtained with 20% Water: 80% MeOH as extraction solvent. Preparations with 20% Water: 80% ACN were not tested.

TABLE 12

| | Analytical Testing Results for Formulations 001 and 002 | | | | | | | |
|---|---|---|---|---|---|---|---|---|
| Sample | L215-01001 | | | | L215-01002 | | | |
| Dose strength | 100 mg/capsule | | | | 100 mg/capsule | | | |
| Sample preparation | Water to dissolve capsule, then complete to volume with methanol Final ratio 20% Water:80% MeOH | | Water to dissolve capsule, then complete to volume with acetonitrile (ACN) Final ratio 20% Water:80% ACN | | Water to dissolve capsule, then complete to volume with methanol Final ratio 20% Water:80% MeOH | | Water to dissolve capsule, then complete to volume with acetonitrile (ACN) Final ratio 20% Water:80% ACN | |
| Assay | 87.9% (n = 2: 83.4, 92.5) | | 101.4% (n = 2: 101.3, 101.5) | | 44.1% (n = 2: 46.7, 41.6) | | 94.6% (n = 2: 94.3, 94.8) | |
| | RRT | % Area | RRT | % Area | RRT | % Area | RRT | % Area |
| Related substances (% area) | 0.22 | 0.01 | 0.25 | 0.01 | 0.26 | 0.02 | 0.25 | 0.01 |
| | 0.26 | 0.01 | 0.27 | 0.07 | 0.28 | 0.13 | 0.27 | 0.08 |
| | 0.28 | 0.08 | 0.72 | 0.18 | 0.49 | 0.03 | 0.71 | 0.18 |
| | 0.49 | 0.02 | 0.90 | 0.14 | 0.72 | 0.30 | 0.90 | 0.13 |
| | 0.72 | 0.19 | 0.93 | 0.29 | 0.90 | 0.32 | 0.93 | 0.27 |
| | 0.90 | 0.22 | Total | 0.70 | 0.93 | 1.02 | Total | 0.67 |
| | 0.93 | 0.68 | | | Total | 1.81 | | |
| | Total | 1.20 | | | | | | |

TABLE 13

Analytical Testing Results for Formulation 003

| Sample | L215-01003 | |
|---|---|---|
| Dose strength | 100 mg/capsule | |
| Sample preparation | Water to dissolve capsule, then complete to volume with methanol Final ratio 20% Water:80% MeOH | Water to dissolve capsule, then complete to volume with acetonitrile (ACN) Final ratio 20% Water:80% ACN |
| Assay | 15.5% (n = 2: 18.5, 12.5) | 50.2% (n = 2: 43.6, 56.8) |

| | RRT | % Area | RRT | % Area |
|---|---|---|---|---|
| Related Substances (% area) | 0.28 | 0.10 | 0.27 | 0.08 |
| | 0.72 | 0.25 | 0.72 | 0.16 |
| | 0.90 | 0.65 | 0.90 | 0.20 |
| | 0.93 | 2.18 | 0.93 | 0.41 |
| | Total | 3.18 | Total | 0.85 |

TABLE 14

Analytical Testing Results for Formulation 004a

| Sample | L215-01004a | |
|---|---|---|
| Dose strength | 100 mg/capsule | |
| Sample preparation | Water to dissolve capsule, then complete to volume with methanol Final ratio 20% Water:80% MeOH | Water to dissolve capsule, then complete to volume with acetonitrile (ACN) Final ratio 20% Water:80% ACN |
| Assay | 13.0% (n = 2: 12.7, 13.3) | 51.8% (n = 2: 59.9, 43.7) |

| | RRT | % Area | RRT | % Area |
|---|---|---|---|---|
| Related Substances (% area) | 0.28 | 0.09 | 0.28 | 0.07 |
| | 0.72 | 0.22 | 0.72 | 0.15 |
| | 0.90 | 0.56 | 0.90 | 0.15 |
| | 0.93 | 1.85 | 0.93 | 0.31 |
| | Total | 2.73 | Total | 0.68 |

TABLE 15

Analytical Testing Results for Formulation 004b

| Sample | L215-01004b | |
|---|---|---|
| Dose strength | 100 mg/capsule | |
| Sample preparation | Water to dissolve capsule, then complete to volume with methanol Final ratio 20% Water:80% MeOH | Water to dissolve capsule, then complete to volume with acetonitrile (ACN) Final ratio 20% Water:80% ACN |
| Assay | 11.0% (n = 2: 10.4, 11.7) | 37.8% (n = 2: 35.5, 40.1) |

| | RRT | % Area | RRT | % Area |
|---|---|---|---|---|
| Related Substances (% area) | 0.28 | 0.09 | 0.28 | 0.08 |
| | 0.72 | 0.23 | 0.72 | 0.15 |
| | 0.90 | 0.76 | 0.90 | 0.16 |
| | 0.93 | 2.41 | 0.93 | 0.36 |
| | Total | 3.49 | Total | 0.74 |

TABLE 16

Analytical Testing Results for Formulation 004c

| Sample | L215-01004c | |
|---|---|---|
| Dose strength | 100 mg/capsule | |
| Sample preparation | Water to dissolve capsule, then complete to volume with methanol Final ratio 20% Water:80% MeOH | Water to dissolve capsule, then complete to volume with acetonitrile (ACN) Final ratio 20% Water:80% ACN |
| Assay | 14.4% (n = 2: 14.8, 14.0) | 32.2% (n = 2: 32.0, 32.5) |

| | RRT | % Area | RRT | % Area |
|---|---|---|---|---|
| Related Substances (% area) | 0.28 | 0.09 | 0.28 | 0.08 |
| | 0.72 | 0.23 | 0.72 | 0.15 |
| | 0.90 | 0.50 | 0.90 | 0.16 |
| | 0.93 | 1.65 | 0.93 | 0.36 |
| | Total | 2.46 | Total | 0.75 |

TABLE 17

Analytical Testing Results for Formulation 005a to 005c

| Sample | L215-01005a | L215-01005b | L215-01005c |
|---|---|---|---|
| Dose strength | 100 mg/capsule | 100 mg/capsule | 100 mg/capsule |
| Assay | 97.9% (n = 2: 97.5, 98.2) | 97.9% (n = 2: 98.5, 97.4) | 98.3% (n = 2: 96.8, 99.8) |

| | RRT | % Area | RRT | % Area | RRT | % Area |
|---|---|---|---|---|---|---|
| Related Substances (% area) | 0.27 | 0.07 | 0.22 | 0.01 | 0.27 | 0.07 |
| | 0.28 | 0.12 | 0.27 | 0.05 | 0.28 | 0.13 |
| | 0.49 | 0.09 | 0.28 | 0.10 | 0.49 | 0.10 |
| | 0.72 | 0.18 | 0.33 | 0.01 | 0.72 | 0.18 |
| | 0.90 | 0.14 | 0.43 | 0.01 | 0.90 | 0.17 |
| | 0.93 | 0.41 | 0.49 | 0.05 | 0.93 | 0.50 |
| | Total | 1.00 | 0.72 | 0.18 | Total | 1.14 |
| | | | 0.90 | 0.14 | | |
| | | | 0.93 | 0.40 | | |
| | | | Total | 0.93 | | |

Sample preparation Water to dissolve capsule, then complete to volume with methanol Final ratio 20% Water:80% MeOH Formulation Lots L215-007a to 007c SDI-DG formulations lots 007a to 007c were obtained by dry granulation of Fenretinide (40%)/Plasdone® K-29/32 (60%) spray-dried intermediate (SDI) material.

These sample preparations were done using water to dissolve the capsules and then completing to volume with acetonitrile for a final ratio 20% Water:80% ACN. In some duplicate samples, the excipients formed a clump in the sample solution which may account for the variability in the replicate assay samples.

The results (Table 18) showed comparable assay values and total amount of related substances for all 3 formulations with increase in impurities of about 1% when compared to neat API (Table 11). Moreover, these formulations showed different related substances profile when compared with neat API and SDI formulations lots 005a, 005b and 005c.

The dissolution testing was achieved using different dissolution media. In acid medium, no release was noted in 1 hour. At pH 6.8 between 67 and 78% of the drug was released within 60 minutes. The dissolution rate depended mostly on aqueous solubility of the filler (lactose or calcium hydrogen phosphate dehydrate) and not on presence of croscarmellose as disintegrant.

TABLE 18

Analytical Testing Results for Formulation 007a to 007c

| Sample | L215-01007a<br>SDI (40% PVP) dry granulation (slugging method) tablet formulation<br>Croscarmellose + Tab-80 | | L215-01007b<br>SDI (40% PVP) dry granulation (slugging method) tablet formulation<br>Croscarmellose + Emcompress | | L215-01007c<br>SDI (40% PVP) dry granulation (slugging method) tablet formulation<br>Aerosil + Tab-80 | |
|---|---|---|---|---|---|---|
| Dose strength<br>Assay | 100 mg/capsule<br>95.8%<br>(n = 2: 98.9, 92.7) | | 100 mg/capsule<br>97.2%<br>(n = 2: 101.1, 93.2) | | 100 mg/capsule<br>94.1&<br>(n = 2: 95.6, 92.5) | |
| | RRT | % Area | RRT | % Area | RRT | % Area |
| Related Substances (% area) | 0.24 | 0.08 | 0.24 | 0.08 | 0.24 | 0.07 |
| | 0.26 | 0.63 | 0.26 | 0.62 | 0.26 | 0.57 |
| | 0.28 | 0.29 | 0.28 | 0.29 | 0.28 | 0.27 |
| | 0.49 | 0.54 | 0.49 | 0.59 | 0.49 | 0.52 |
| | 0.72 | 0.19 | 0.72 | 0.19 | 0.72 | 0.19 |
| | 0.90 | 0.06 | 0.90 | 0.06 | 0.90 | 0.06 |
| | 0.93 | 0.14 | 0.93 | 0.15 | 0.93 | 0.14 |
| | Total | 1.93 | Total | 1.97 | Total | 1.81 |
| | Time (minutes) | % Dissolved | Time (minutes) | % Dissolved | Time (minutes) | % Dissolved |
| Dissolution Paddles, 100 rpm ramp to 200 rpm at 60 minutes 900 ml 0.1N HCl + 2.0% SDS | 10 | 5 | 10 | 1 | 10 | 0 |
| | 20 | 5 | 20 | 1 | 20 | 0 |
| | 30 | 4 | 30 | 0 | 30 | 0 |
| | 60 | 2 | 60 | 0 | 60 | 0 |
| | 75 | 1 | 75 | 0 | 75 | 0 |
| Dissolution Paddles, 100 rpm ramp to 200 rpm at 60 minutes 900 ml pH 6.8 + 2.0% SDS | 10 | 65 | 10 | 57 | 10 | 67 |
| | 20 | 72 | 20 | 65 | 20 | 77 |
| | 30 | 75 | 30 | 65 | 30 | 78 |
| | 60 | 73 | 60 | 67 | 60 | 78 |
| | 75 | 75 | 75 | 65 | 75 | 81 |
| Dissolution Paddles, 100 rpm ramp to 200 rpm at 60 minutes 900 ml pH 8.0 + 2.0% SDS | 10 | 66 | 10 | 60 | 10 | 34 |
| | 20 | 71 | 20 | 67 | 20 | 72 |
| | 30 | 73 | 30 | 66 | 30 | 72 |
| | 60 | 73 | 60 | 66 | 60 | 76 |
| | 75 | 72 | 75 | 66 | 75 | 73 |

Note:
A stock standard diluted in the 80% acetonitrile was used to quantitate the dissolution samples. The stock standard was also diluted in each of the dissolution medium, good recoveries were obtained for these standard solutions.

Figure 13:
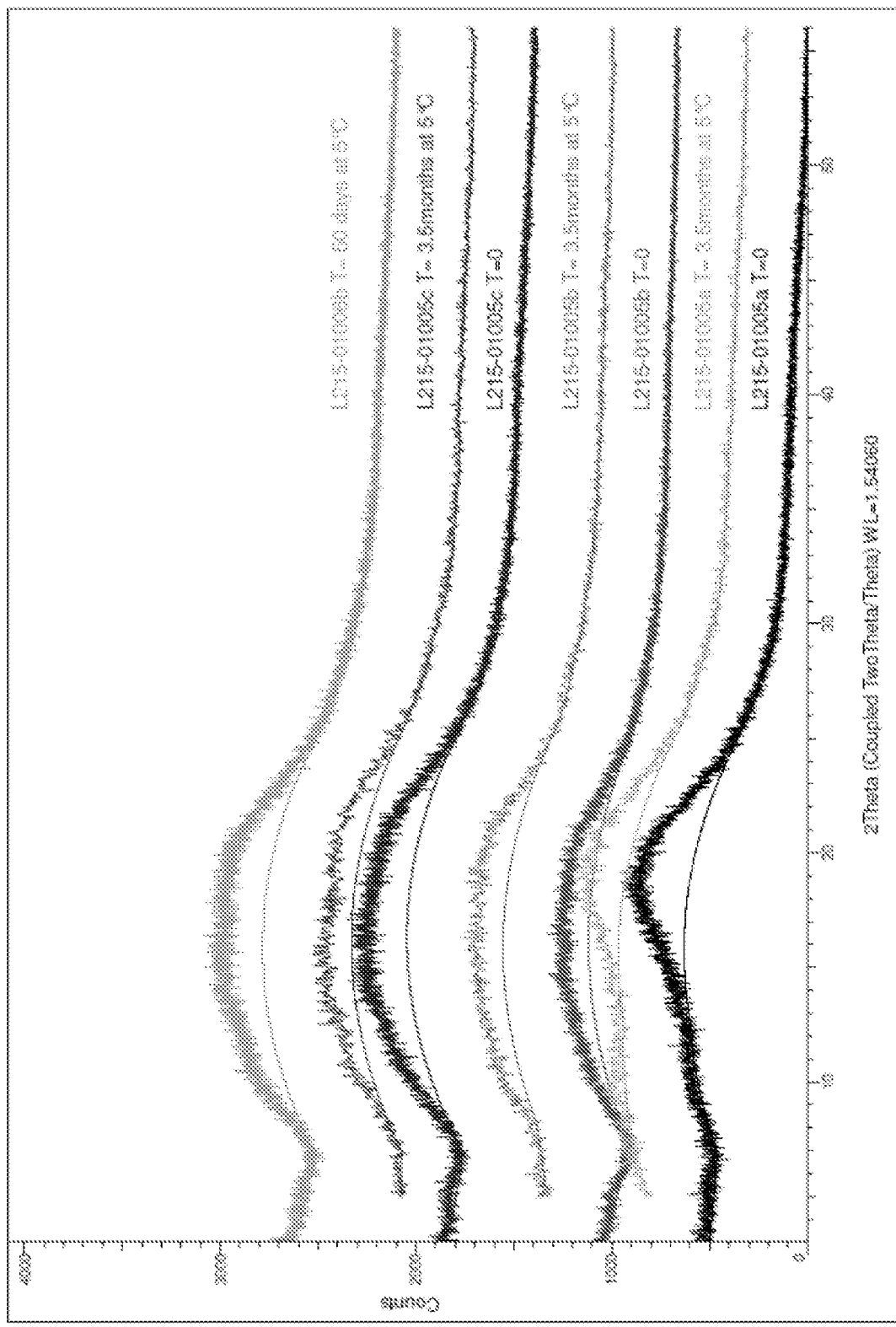
FIG. 13 shows XRPD diffractograms of Fenretinide SDIs after manufacturing (T=0) and after 3.5 months of storage at 5° C. (bulk powder in amber glass bottles).

Example 4: SDI—Crystal State of Formulation Lots L215-01005a, L215-01005b and L215-01005c FIG. 1 shows that irrespective of the polymer used as co-precipitate, amorphous SDI was produced. Physical stability of the spray-dried amorphous solid dispersion formulations (spray-dried intermediate) was evaluated by XRPD. Lots L215-01005a, 005b and 005c were tested after manufacturing (T=0) and after 3.5 months of storage at 5° C. (bulk powder in amber glass bottles). As shown in FIG. 13, the amorphous form remained stable during storage period. The lot L215-01006b was tested after 50 days under refrigerator conditions and as shown the drug remains in an amorphous state.

Example 5: Pharmacokinetics Study of Formulation Lots L215-01002, L215-01003, L215-01004b, L215-01004c, L215-01005b and L215-01005c in Rats The objective of this study was to determine pharmacokinetic profiles of 6 Prototype formulations of Fenretinide, after an oral dosage in rats with the aim to select the best prototype for further optimization.

Study Protocol

Animals: Sprague-Dawley, male rats, n=3 per each formulation

Dosage regimen: Oral capsule gavage, (2×5 mg)

PK Timepoints: 0, 0.5, 1, 2, 4, 7, 14 and 24 hours (0.5 ml/timepoint in $K_2$EDTA)

The studies were conducted at the Centre National de Biologie Experimentale (CNBE) of the Institut Nationale de Recherche Scientifique (INRS). Six different prototypes of fenretinide oral formulations were prepared in number 9 cellulose capsules (6 capsules/formulation). Three rats per each formulation type (weight 326-365.7 g) were administered 2 capsules each using special delivery syringe after overnight fasting.

| Animal ID | Product | Group |
|---|---|---|
| 1 | Fenretinide 5 MG | 1 |
| 2 | Lot #: L215-01002PK | |

-continued

| Animal ID | Product | Group |
|---|---|---|
| 3 | MFG: 2013JN19 | |
| 4 | Fenretinide 5 MG | 2 |
| 5 | Lot #: L215-01003PK | |
| 6 | MFG: 2013JN20 | |
| 7 | Fenretinide 5 MG | 3 |
| 8 | Lot #: L215-01004bPK | |
| 9 | MFG: 2013JN20 | |
| 10 | Fenretinide 5 MG | 4 |
| 11 | Lot #: L215-01004cPK | |
| 12 | MFG: 2013JN20 | |
| 13 | Fenretinide 5 MG | 5 |
| 14 | Lot #: L215-01005bPK | |
| 15 | MFG: 2013JN21 | |
| 16 | Fenretinide 5 MG | 6 |
| 17 | Lot #: L215-01005cPK | |
| 18 | MFG: 2013JN21 | |

Blood samples were taken by jugular vein (0.5 ml/sample) puncture samples and the obtained plasma was analyzed (HPLC) by MsPharma Inc., in Laval. Details of the analytical method are as follows.

Analysis of Fenretinide content in plasma sample by HPLC-UV.

Principle:

The principle is to retain the compound using a C18 reverse phase and an HPLC with UV detection at 360 nm.

Definitions

MP=Mobile Phase; MeOH=Methanol; HCl=Hydrochloric acid; RT=Room temperature; % RSD=% of relative standard deviation; % RD=% of relative deviation C or [ ]=concentration in pg/ml, ws=sample weight, V=Volume of sample preparation, Ae=response of the sample, As=response of the standard, D=dilution factor, S/N=Signal-to-Noise ratio, 4-HPR=Fenretinide; 4-MPR=N-(4-methoxyphenyl)retinamide.

Materials:

HPLC with a C18 Inertsil ODS-3, 250×4.6 mm, 5 μm

MeOH, Water, syringe filter PVDF 0.45 μm, 4-HPR and 4-MPR.

Procedure:

The HPLC Conditions for plasma samples analysis are:

| Column: | C18 Inertsil ODS-3, 5 μm, 4.6 × 250 mm or equivalent |
|---|---|
| Wavelength: | 360 nm |
| Flow rate*: | 1.0 mL/min. |
| Temperature: | 35° C. |
| Injection Volume: | 100 μL |

| MP (Gradient): | Time (min) | % Water | % MeOH |
|---|---|---|---|
| | 0 | 75 | 25 |
| | 2 | 75 | 25 |
| | 3 | 1 | 99 |
| | 14 | 1 | 99 |
| | 14.01 | 75 | 25 |
| | 18 | 75 | 25 |

The concentration of each sample was determined using the calibration curve forced through zero of the area ratio from the internal standard peak (N-(4-ethoxyphenyl)retinamide, 4-EPR) and the concentration (μg/mL).

$$\text{Calculation } \mu g/mL = \frac{Ae}{m} \text{ Where } m = \text{Slope}$$

Results

Figure 2:
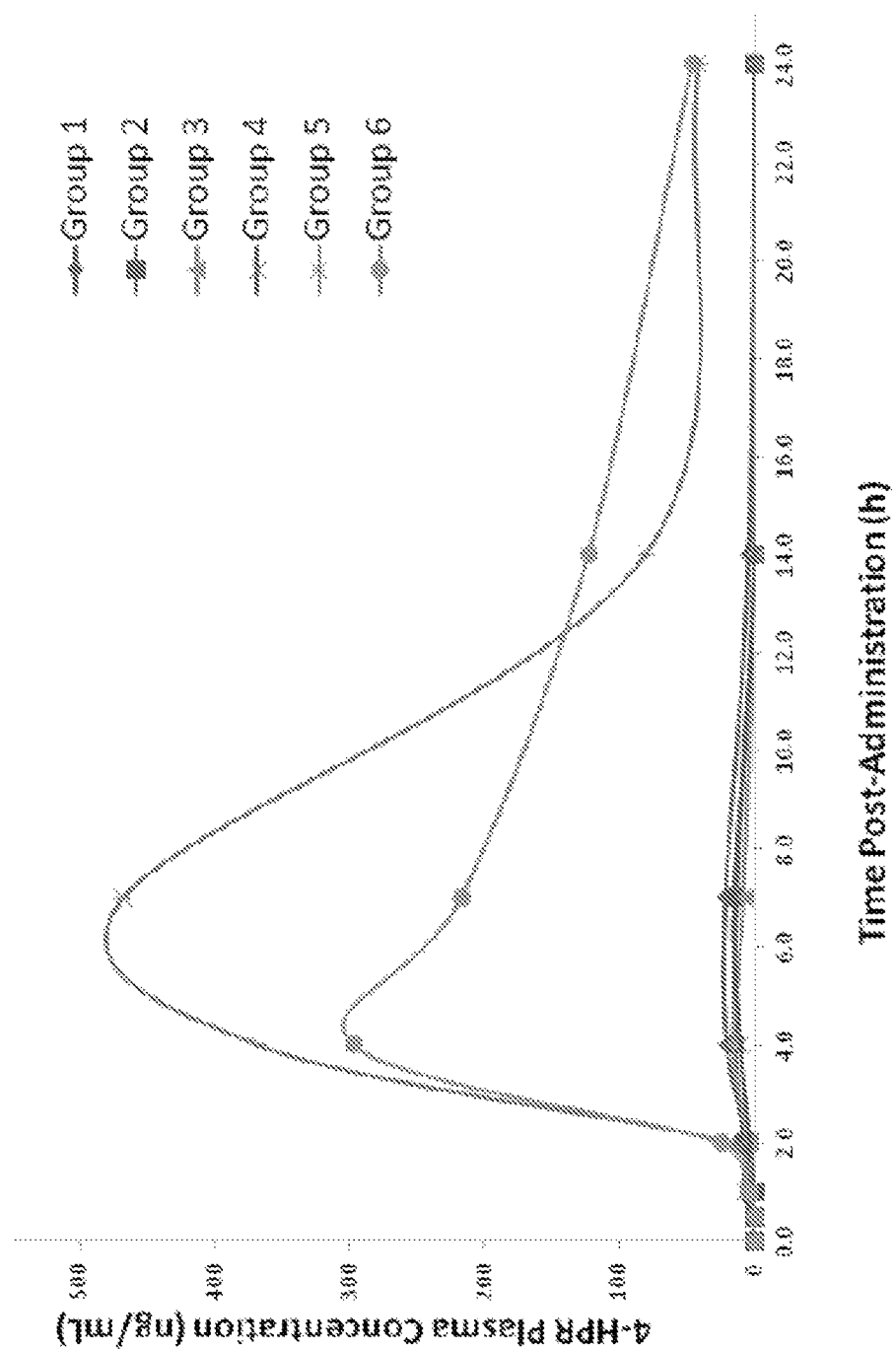
FIG. 2 shows the pharmacokinetics profiles of 6 prototype formulations in rats after oral dose of 10 mg.

The results are illustrated in FIG. 2 and in the Tables 19 and 20 below. The obtained plasma concentrations indicate relatively slow absorption of Fenretinide (appearing at 1-2 hrs post-dose). $T_{max}$ between 4 and 7 hours was observed for all types of formulations tested, indicating that the absorption occurs probably mainly in the lower small intestine. In Groups 1-4, the $C_{max}$ (14.4-21 ng/mL) and $AUC_{(0-24h)}$ (86-196 ng-h/mL) were lower compared to the groups 5 and 6. The elimination half-life was determined only for Groups 5 and 6 and was consistent with the literature data for fenretinide (7-10 hrs) in rats. The highest fenretinide plasma exposure was observed in Group 5 (4188.7 ng-h/mL), followed by group 6 (3146.2 ng-h/mL).

TABLE 19

Summary of mean Fenretinide plasma concentration

| Time (h) | Gr 1 | Gr 2 | Gr 3 | Gr 4 | Gr 5 | Gr 6 |
|---|---|---|---|---|---|---|
| 0 | 0.000 | 0.000 | 0.000 | 0.000 | 0.000 | 0.000 |
| 0.5 | 0.000 | 0.000 | 0.000 | 0.000 | 0.000 | 0.000 |
| 1 | 0.000 | 0.000 | 3.850 | 8.523 | 4.017 | 4.383 |
| 2 | 3.597 | 7.903 | 3.923 | 4.317 | 18.563 | 24.060 |
| 4 | 20.137 | 14.350 | 15.657 | 10.437 | 367.857 | 297.517 |
| 7 | 21.063 | 13.477 | 7.710 | 15.017 | 468.057 | 217.337 |
| 14 | 4.177 | 0.000 | 0.000 | 0.000 | 81.070 | 123.060 |
| 24 | 0.000 | 0.000 | 0.000 | 0.000 | 41.760 | 46.077 |

Clinical Observations:

Gr. 2—⅓ rats did not received complete dose (second capsule partially delivered)

All groups—increased water consumption observed in all rats after 2 hrs post-dose

TABLE 20

PK parameters after single oral dose of Fenretinide in rats

| Parameter (Units) | Group 1 | Group 2 | Group 3 | Group 4 | Group 5 | Group 6 |
|---|---|---|---|---|---|---|
| $C_{max}$ (ng/mL) | 21.1 | 14.4 | 15.7 | 15.0 | 468.1 | 297.5 |
| $T_{max}(h)^a$ | 7 | 4 | 4 | 7 | 7 | 4 |
| $t_{1/2e(h)}$ | nd | nd | nd | nd | 10.4447131 | 7.053131 |
| VD (L) | nd | nd | nd | nd | 89.7 | 81.1 |
| $AUC_{0-24}$ (ng·h/mL) | 196.6 | 115.1 | 86.5 | 114.0 | 4188.7 | 3146.2 |

Example 6: Pharmacokinetics Study of Formulation Lots L215-01005a, L215-01005c, L215-01007a, L215-01007b and L215-01007c in Rats The objectives of this study were to continue the optimization of the most promising prototypes studied in the previous pharmacokinetic study in rats. A new series of optimized prototypes was produced (L215-01007a, L215-01007b and L215-01007c) and compared with some of the previous prototypes (L215-01005a and L215-01005c) and with the original Fenretinide corn-oil formulation. The formulation with the most favourable pharmacokinetic profile for development of formulation suitable for treatment of human subjects was selected for future studies.

Study Protocol
  Animals: Sprague-Dawley, female rats, n=3 per each formulation
  Dosage regimen: Single dose by oral gavage
  PK Timepoints: 0, 1, 2, 4, 5, 7, 14, 24 and 48 hours (0.5 ml/timepoint)

The studies were conducted at the Centre National de Biologie Experimentale (CNBE) of the Institut Nationale de Recherche Scientifique (INRS). Six different fenretinide oral formulations were studied; 5 solid formulations presented in number 9 gelatine capsules (min 6 capsules/formulation, Table 21) and one liquid suspension formulation in corn oil.

TABLE 21

Overview of the study groups

| Animal ID | Formulation | Group | Dose/rat | Dose (mg/rat) | Mean Dose/Group (mg/kg) |
|---|---|---|---|---|---|
| 20 | Fenretinide | 7 | 300 µL | 11.4 | 32.0 |
| 21 | 38.02 mg/mL | | 300 µL | 11.4 | |
| 22 | Corn oil formulation | | 300 µL | 11.4 | |
| 23 | Fenretinide | 8 | 2 capsules | 5 | 13.3 |
| 24 | 2.5 mg/capsule | | 2 capsules | 5 | |
| 25 | Lot #: L215-01007a Mfg: 2013JL23 | | 2 capsules | 5 | |
| 26 | Fenretinide | 9 | 2 capsules | 5 | 13.5 |
| 27 | 2.5 mg/capsule | | 2 capsules | 5 | |
| 28 | Lot #: L215-01007b Mfg: 2013JL23 | | 2 capsules | 5 | |
| 29 | Fenretinide | 10 | 2 capsules | 5 | 13.8 |
| 30 | 2.5 mg/capsule | | 2 capsules | 5 | |
| 31 | Lot #: L215-01007c Mfg: 2013JL23 | | 2 capsules | 5 | |
| 32 | Fenretinide | 11 | 2 capsules | 10 | 27.4 |
| 33 | 5 mg/capsule | | 2 capsules | 10 | |
| 34 | Lot #: L215-01005a Mfg: 2013JL16 | | 2 capsules | 10 | |
| 35 | Fenretinide | 12 | 2 capsules | 10 | 26.8 |
| 36 | 5 mg/capsule | | 2 capsules | 10 | |
| 37 | Lot #: L215-01005c Mfg: 2013JL22 | | 2 capsules | 10 | |

The suspension formulation was prepared by extraction of the content of 3 McNeil soft capsules containing each 100 mg of 4-HPR (obtained from the National Cancer Institute, National Institutes of Health, Bethesda, Md., USA). The content of the three capsules was mixed, diluted to obtain a final concentration between 35-40 mg/ml by adding corn oil followed by vigorous mixing for 4 minutes. The concentration of 4-HPR in the final corn-oil formulation for animal dosing was confirmed by HPLC analysis (MsPharma Inc.) prior to gavaging animals, and contained 38.02 mg/mL of 4-HPR.

Three female Sprague-Dawley rats per group (weight 337.1-390.3 g) received 2 capsules each per os using special capsule delivery syringe. Groups 8, 9 and 10 received the optimized formulations (L215-01007a, L215-01007b and L215-01007c) and Groups 11 and 12 the prototype formulations (L215-01005a and L215-01005c). The corn oil based formulation was administered to 3 rats of Group 7 in a volume of 300 µL per rat using a stainless steel gavage needle. Following the dosing of the drug formulations there were no clinical observations in any of the groups up to 48 hours, the last time point studied, at which the animals were euthanized.

Blood samples were collected into K2EDTA tubes at predetermined timepoints by jugular vein puncture (~0.5 mL/sample) alternating the left and right jugular veins sites. The blood samples were kept on wet ice protected from direct light until centrifugation. The obtained plasma was immediately transferred to amber Eppendorf tubes and stored at −20° C. until analysis. The animals were fasted overnight before the dosing (water ad libitum) and were fed approximately 2 hours after the dosing.

Figure 3:
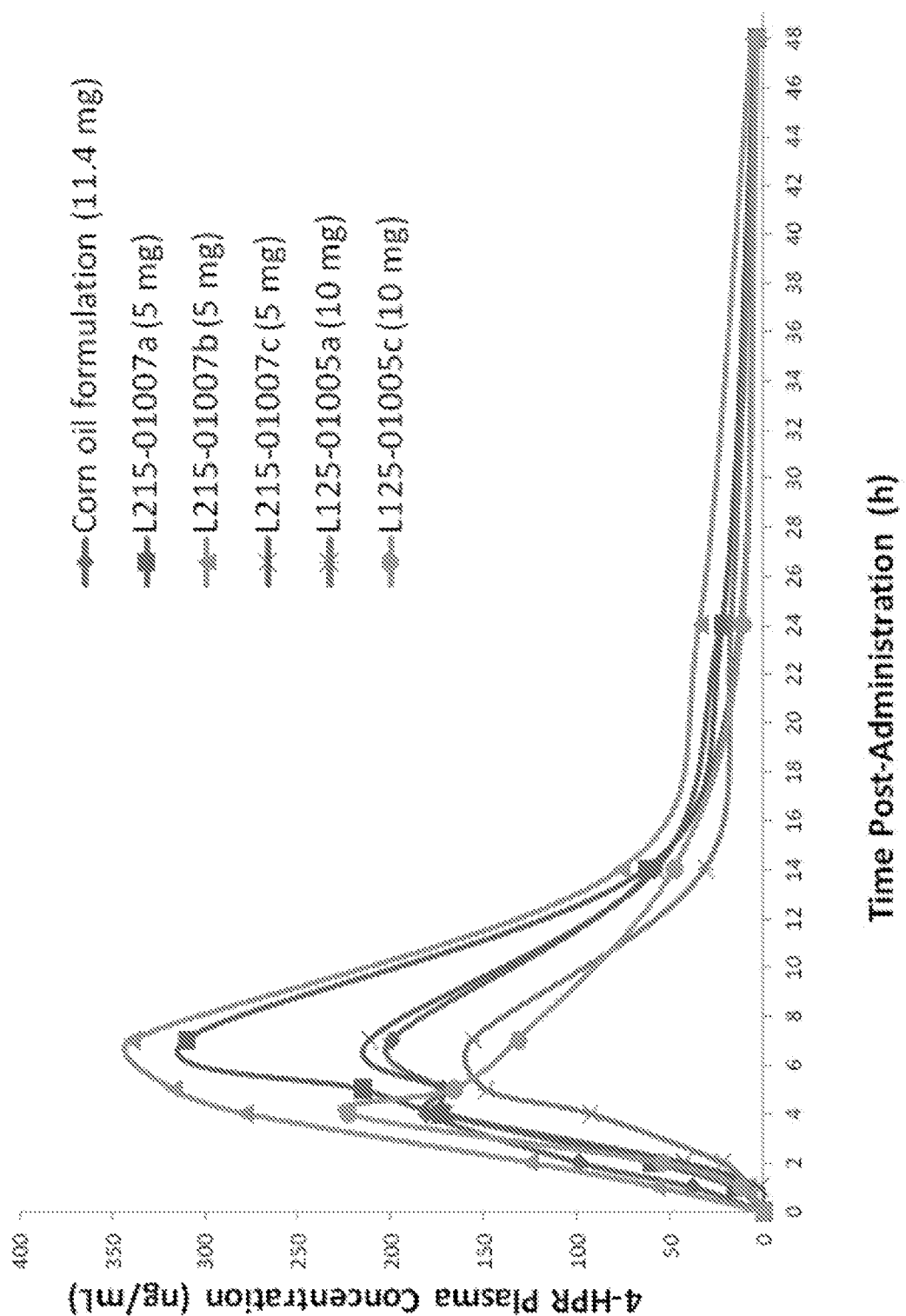
FIG. 3 shows 4-HPR (fenretinide) plasma profiles of 6 formulations after single oral dose in rats.
Figure 4:
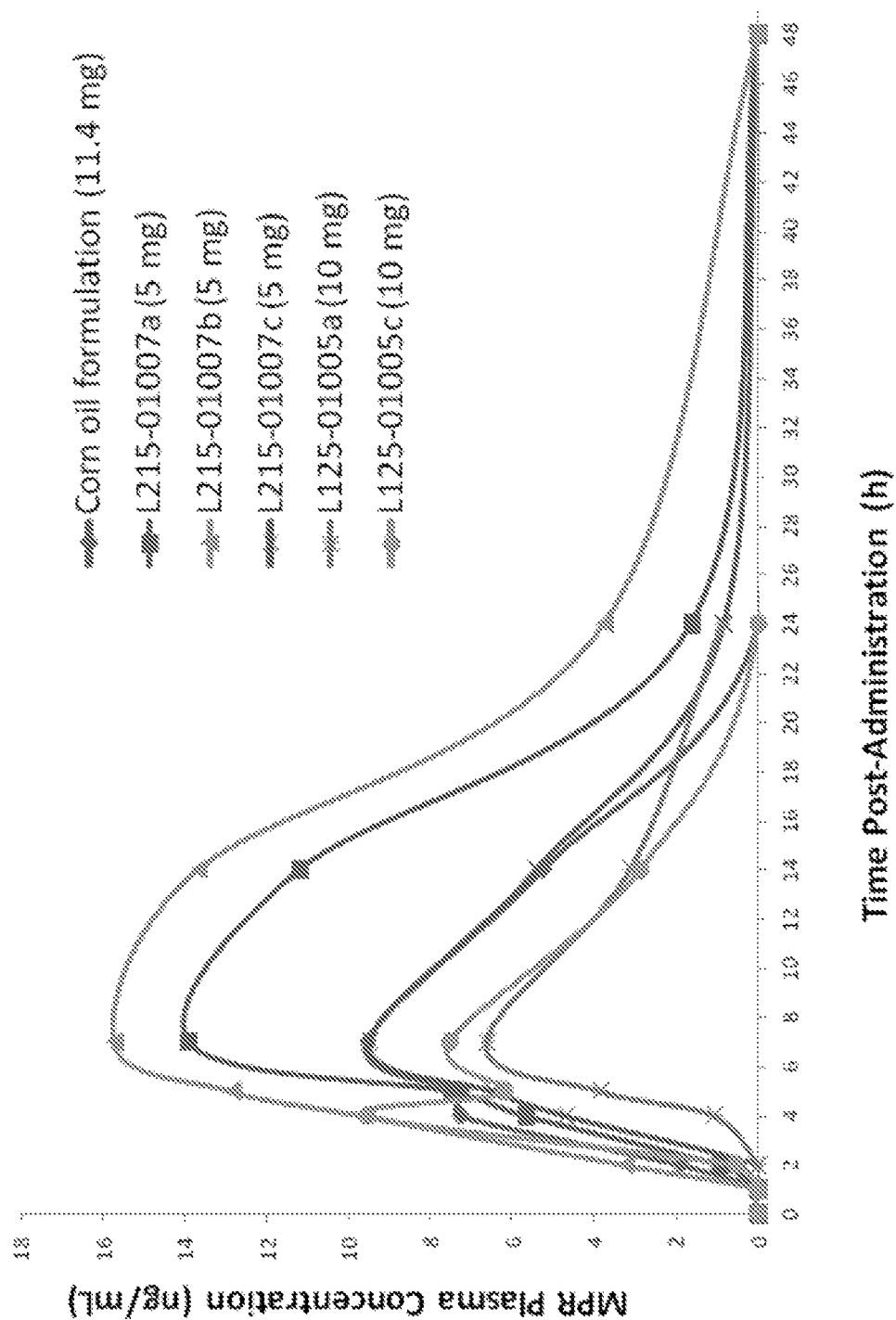
FIG. 4 shows 4-MPR (N-[4-methoxyphenyl]retinamide) plasma profiles of 6 formulations after single oral dose of 4-HPR in rats.
Figure 5:
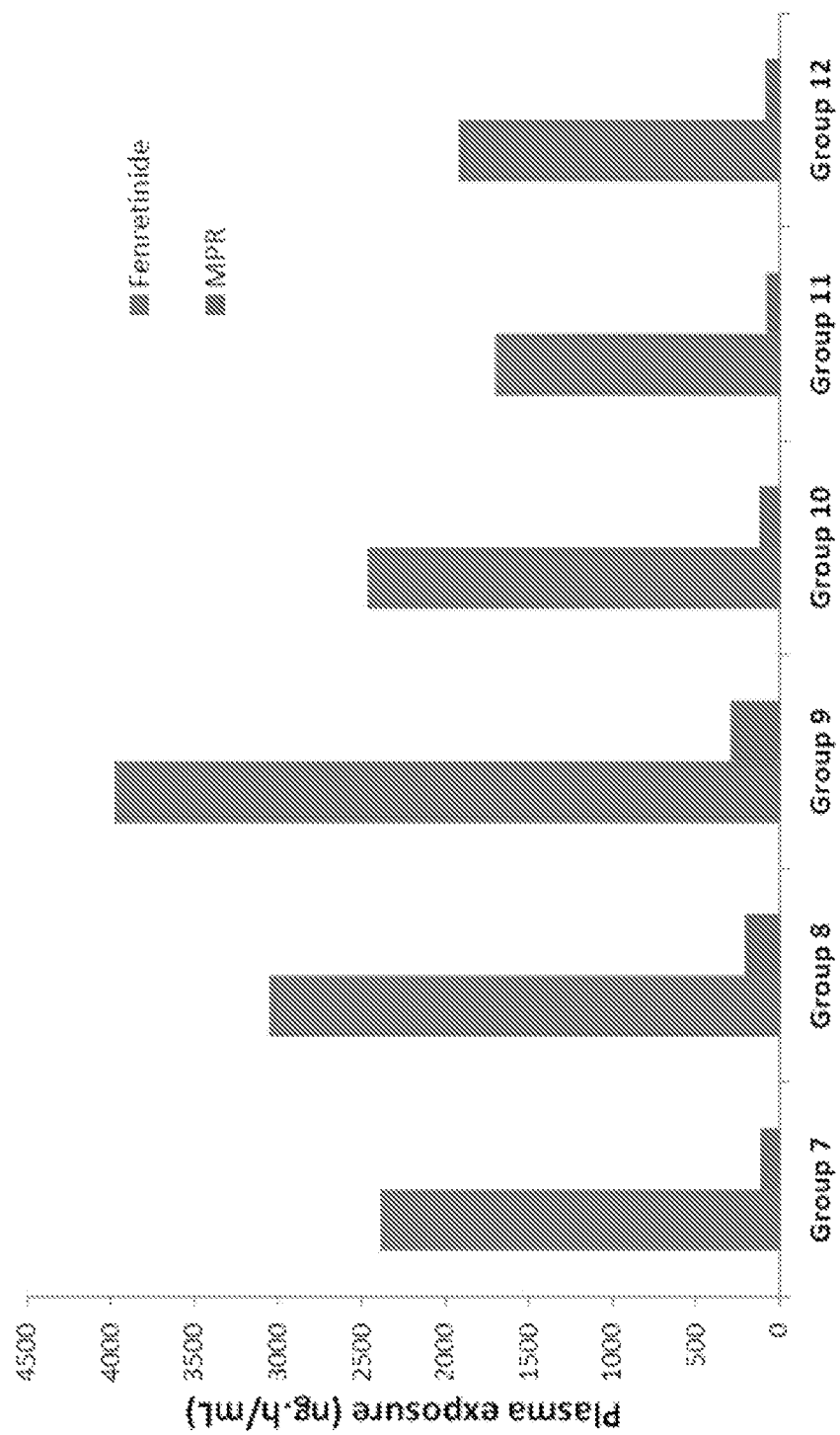
FIG. 5 shows plasma exposure ($AUC_{0-48}$) of 4-HPR and 4-MPR of 6 formulations (groups 7 to 12) after single oral dose in rats. Left bars=fenretinide (4-HPR); right bars=MPR.

The obtained plasma was analyzed by HPLC at MsPharma Inc. (Laval, QC) for content of 4-HPR and 4-MPR, the main metabolite of 4-HPR, using the bioanalytical method described above. After integration of the peak areas, data were exported to an Excel® (Microsoft®) spreadsheet. The Excel spreadsheet was used for calculation of 4-HPR and 4-MPR concentrations in rat plasma and for descriptive statistics. Mean concentration-time data for each timepoint were analyzed using PC Solution Software 2.0™ (Summit Research Services, Montrose, Colo., USA) with nominal sampling times. $C_{max}$ and $T_{max}$ were confirmed by inspection of observed data. Areas under the plasma mean concentration-time curves (AUC) were estimated using the linear trapezoidal rule and reported as $AUC_{(0-48)}$. Apparent terminal half-life ($t_{1/2}$) was determined, when possible, by linear regression analysis of three concentrations that appeared to be on the terminal elimination phase of the mean concentration time-curve. The bioanalytical data and results for 4-HPR and 4-MPR are presented in FIGS. 3-5 and in Tables 22-27.

TABLE 22

Summary of mean 4-HPR plasma concentration (ng/mL, n = 3)

| Time (h) | Group 7 Corn oil Formulation | | Group 8 Optimized L215-01007a | | Group 9 Optimized L215-01007b | | Group 10 Optimized L215-01007c | | Group 11 Prototype L215-01005a | | Group 12 Prototype L215-01005c | |
|---|---|---|---|---|---|---|---|---|---|---|---|---|
| | Mean | SEM | Mean | SEM | Mean | SEM | Mean | SEM | Mean | SEM | Mean | SEM |
| 0 | 0.0 | 0.0 | 0.0 | 0.0 | 0.0 | 0.0 | 0.0 | 0.0 | 0.0 | 0.0 | 0.0 | 0.0 |
| 1 | 38.6 | 0.6 | 15.3 | 14.4 | 57.7 | 44.9 | 2.0 | 1.2 | 7.9 | 4.0 | 12.3 | 12.3 |
| 2 | 99.5 | 12.9 | 60.3 | 40.8 | 126.1 | 63.8 | 43.1 | 19.1 | 21.9 | 9.7 | 54.8 | 31.1 |

TABLE 22-continued

Summary of mean 4-HPR plasma concentration (ng/mL, n = 3)

| | Group 7 Corn oil Formulation | | Group 8 Optimized L215-01007a | | Group 9 Optimized L215-01007b | | Group 10 Optimized L215-01007c | | Group 11 Prototype L215-01005a | | Group 12 Prototype L215-01005c | |
|---|---|---|---|---|---|---|---|---|---|---|---|---|
| Time (h) | Mean | SEM | Mean | SEM | Mean | SEM | Mean | SEM | Mean | SEM | Mean | SEM |
| 4 | 181.7 | 22.3 | 174.1 | 40.2 | 279.3 | 44.8 | 171.5 | 82.4 | 93.2 | 33.7 | 223.9 | 24.6 |
| 5 | 172.6 | 23.5 | 215.9 | 36.7 | 317.4 | 28.6 | 172.1 | 89.5 | 149.4 | 14.8 | 166.7 | 32.3 |
| 7 | 200.3 | 40.0 | 310.8 | 1.9 | 340.0 | 77.0 | 212.3 | 57.7 | 156.1 | 48.7 | 132.1 | 15.9 |
| 14 | 58.8 | 19.4 | 63.3 | 11.6 | 76.6 | 9.3 | 57.9 | 12.8 | 31.4 | 9.4 | 48.0 | 12.9 |
| 24 | 12.3 | 6.3 | 22.0 | 4.0 | 34.3 | 1.5 | 22.6 | 3.8 | 17.0 | 4.1 | 11.3 | 0.8 |
| 48 | 4.6 | 1.3 | 3.9 | 0.6 | 5.9 | 1.0 | 4.1 | 1.1 | 2.8 | 1.4 | 3.3 | 0.9 |

TABLE 23

Calculated PK parameters after single oral dose of 4-HPR in rats

| Parameter (Units) | Group 7 Corn oil Formulation | Group 8 Optimized L215-01007a | Group 9 Optimized L215-01007b | Group 10 Optimized L215-01007c | Group 11 Prototype L215-01005a | Group 12 Prototype L215-01005c |
|---|---|---|---|---|---|---|
| Mean Dose (mg/kg) | 32.0 | 13.3 | 13.5 | 13.8 | 27.4 | 26.8 |
| $C_{max}$ (ng/mL) | 200.3 | 310.8 | 340.0 | 212.3 | 156.1 | 223.9 |
| $T_{max}$(h)$^a$ | 7 | 7 | 7 | 7 | 7 | 4 |
| $AUC_{0-48}$ (ng·h/mL) | 2385.1 | 3047.4 | 3977.4 | 2464.1 | 1696.3 | 1915.2 |
| $t_{1/2e(h)}$ | 10.1 | 8.6 | 9.3 | 9.1 | 9.7 | 9.5 |
| VD (L) | 69.8 | 20.4 | 16.8 | 26.5 | 82.4 | 71.2 |
| Clearance (mL/h) | 4243.0 | 1640.8 | 1257.1 | 2029.2 | 5895.3 | 5221.3 |

TABLE 24

4-HPR plasma exposure normalized to 20 mg/kg oral dose

| Parameter (Units) | Group 7 Corn oil Formulation | Group 8 Optimized L215-01007a | Group 9 Optimized L215-01007b | Group 10 Optimized L215-01007c | Group 11 Prototype L215-01005a | Group 12 Prototype L215-01005c |
|---|---|---|---|---|---|---|
| $AUC_{0-48}$ (ng·h/mL) | 1490.68 | 4584.87 | 5911.44 | 3579.49 | 1238.96 | 1429.15 |
| $C_{max}$ (ng/mL) | 125.18 | 467.54 | 505.30 | 308.36 | 114.04 | 167.07 |
| % of Corn oil AUC | 100 | 307.6 | 396.6 | 240.1 | 83.1 | 95.9 |

TABLE 25

Summary of mean 4-MPR concentration after 4-HPR oral dose (ng/mL, n = 3)

| | Group 7 Corn oil Formulation | | Group 8 Optimized L215-01007a | | Group 9 Optimized L215-01007b | | Group 10 Optimized L215-01007c | | Group 11 Prototype L215-01005a | | Group 12 Prototype L215-01005c | |
|---|---|---|---|---|---|---|---|---|---|---|---|---|
| Time (h) | Mean | SEM | Mean | SEM | Mean | SEM | Mean | SEM | Mean | SEM | Mean | SEM |
| 0 | 0.0 | 0.0 | 0.0 | 0.0 | 0.0 | 0.0 | 0.0 | 0.0 | 0.0 | 0.0 | 0.0 | 0.0 |
| 1 | 0.0 | 0.0 | 0.0 | 0.0 | 0.0 | 0.0 | 0.0 | 0.0 | 0.0 | 0.0 | 0.0 | 0.0 |
| 2 | 1.9 | 1.0 | 0.9 | 0.9 | 3.2 | 2.3 | 0.0 | 0.0 | 0.0 | 0.0 | 0.5 | 0.5 |
| 4 | 7.3 | 0.9 | 5.7 | 2.8 | 9.7 | 2.9 | 4.7 | 3.0 | 1.1 | 1.1 | 9.6 | 2.0 |
| 5 | 7.3 | 1.2 | 7.5 | 1.1 | 12.9 | 2.2 | 6.5 | 4.3 | 3.9 | 0.2 | 6.2 | 1.5 |
| 7 | 9.6 | 1.7 | 13.9 | 0.7 | 15.7 | 3.5 | 9.5 | 4.0 | 6.6 | 2.3 | 7.6 | 1.4 |
| 14 | 5.3 | 1.5 | 11.2 | 2.0 | 13.7 | 4.2 | 5.4 | 1.0 | 3.1 | 1.6 | 2.9 | 1.7 |
| 24 | 0.0 | 0.0 | 1.6 | 0.8 | 3.8 | 0.3 | 0.8 | 0.8 | 0.9 | 0.9 | 0.0 | 0.0 |
| 48 | 0.0 | 0.0 | 0.0 | 0.0 | 0.0 | 0.0 | 0.0 | 0.0 | 0.0 | 0.0 | 0.0 | 0.0 |

TABLE 26

Calculated PK parameters of 4-MPR after single oral dose of 4-HPR in rats

| Parameter (Units) | Group 7 Corn oil Formulation | Group 8 Optimized L215-01007a | Group 9 Optimized L215-01007b | Group 10 Optimized L215-01007c | Group 11 Prototype L215-01005a | Group 12 Prototype L215-01005c |
|---|---|---|---|---|---|---|
| $C_{max}$ (ng/mL) | 9.6 | 13.9 | 15.7 | 9.5 | 6.6 | 9.6 |
| $T_{max}$(h)$^a$ | 7 | 7 | 7 | 7 | 7 | 4 |
| $AUC_{0-24}$ (ng·h/mL) | 112.5 | 207.2 | 289.9 | 119.9 | 78.5 | 83.1 |
| % of fenretinide AUC | 4.7 | 6.8 | 7.3 | 4.9 | 4.6 | 4.3 |

TABLE 27

4-MPR plasma exposure normalized to 20 mg/kg oral dose of 4-HPR

| Parameter (Units) | Group 7 Corn oil Formulation | Group 8 Optimized L215-01007a | Group 9 Optimized L215-01007b | Group 10 Optimized L215-01007c | Group 11 Prototype L215-01005a | Group 12 Prototype L215-01005c |
|---|---|---|---|---|---|---|
| $C_{max}$ (ng/mL) | 5.98 | 20.96 | 23.40 | 13.82 | 4.85 | 7.14 |
| $AUC_{0-48}$ (ng·h/mL) | 70.41 | 311.69 | 430.81 | 174.20 | 57.33 | 62.02 |
| % of Corn oil AUC | 100 | 442.7 | 611.9 | 247.4 | 81.4 | 88.1 |

The 4-HPR plasma concentration profile of all the formulations showed a similar pattern (FIG. 3); very low plasma levels present at 1 hour after dose and maximum concentrations of 156.1-340 ng/mL ($C_{max}$) reaching at 7 hours ($T_{max}$), (Tables 22 and 23) indicated a relatively slow absorption occurring probably in the lower small intestine. 4-HPR appeared to be highly distributed in bodily tissues. The elimination followed a first order kinetic; the half-life ($t_{1/2}$) was between 8.6 h and 10.1 h. Plasma exposure $AUC_{(0-48h)}$ varied significantly among the different formulation types (1696.3-3977.4 ng·h/mL). 4-HPR exposure data normalized to 20 mg/kg dose (Table 24) indicate relatively high exposure achieved with all 3 optimized formulations (Groups 8, 9 and 10) 2.4-4 times higher when compared to the 4-HPR corn oil formulation (1490.7 ng·h/mL) while the prototype formulations (Groups 11 and 12) led to an exposure similar to the corn oil formula. The highest fenretinide plasma exposure was observed in Group 9 (5911.4 ng·h/mL).

Statistical analysis of raw plasma concentrations of the three optimized formulations using Two-way ANOVA analysis followed by All Pairwise Multiple Comparison Procedures (Student-Newman-Keuls Method) demonstrated that the difference in the mean values among the different levels of group and time points were greater than would be expected by chance (P=0.004). There was no statistical difference in plasma concentrations among the 3 groups of animals receiving optimized formulation at all but one time points tested. Only at the 5 hr time point there was statistically significant (p=0.036) difference between Groups 9 and 10.

The plasma profile of 4-MPR (main metabolite of 4-HPR) generally followed the profile of 4-HPR (FIG. 4). 4-MPR appeared in plasma at 2-4 hours after the dosing, reached relatively low $C_{max}$ (9.5-15.7 ng/mL) at $T_{max}$ of 4-7 hours (Tables 25 and 26). Plasma exposure of 4-MPR relative to the parent 4-HPR (FIG. 5) varied between 4.3% (Gr. 12) and 7.3% (Gr. 10). 4-MPR exposure data normalized to 20 mg/kg of 4-HPR dose (Table 27) indicated 2.5-6.1 times higher 4-MPR levels in the optimized formulations when compared to the corn oil formulation, following an approximately equivalent increase in 4-HPR plasma exposure.

The above data shows that compared to the corn oil formulation, all three optimized formulations lead to higher plasma exposure of 4-HPR (2.4-4 times) after a single oral dose in the rat model. Highest apparent exposure was achieved with the formulation dosed in Group 9 (Lot #: L215-01007b).

Example 7: Solid Dispersion Optimization

Solvent System Optimization, Solid Loading Maximization and Scale-Up

Based on the results of the pharmacokinetics studies in animals described above, the solid dispersion approach (lots L215-01005 to L215-01008) was selected for Fenretinide clinical trial material (CTM) manufacturing.

The first step of the optimization was to replace the methanol by ethanol to avoid using multiple solvents with higher toxic potential. Indeed, methanol is a class 2 solvent (solvent to be limited) in pharmaceutical products with a concentration limit of 3000 ppm while ethanol is a class 3 solvent (solvent with low toxic potential) with a concentration limit of 5000 ppm (U.S. Department of Health and Human Services, Food and Drug Administration, Center for Drug Evaluation and Research (CDER), Guidance for Industry Q3C Impurities: Residual Solvents, December 1997). For information, Dichloromethane (DCM) is also a class 2 solvent with a concentration limit of 600 ppm.

When solubilised with PVP K30 in a ratio of 40/60 w/w, it was determined that the solubility of Fenretinide in ethanol 100% was about 34 mg/ml and over 50 mg/ml in DCM 100% or a mixture of ethanol/DCM 50/50 v/v. The systems with ethanol had similar viscosity value and higher than the system composed of DCM only (Table 28) suggesting a higher solid loading limit with increasing amount of DCM.

TABLE 28

Viscosity at RT of Fenretinide/PVP K30 40/60%
w/w Solution in Various Solvent Systems

| Solvent System (Fenretinide concentration) | Viscosity (mPas) |
|---|---|
| EtOH 100% (34 mg/ml) | 6.45 |
| EtOH/DCM 50/50 v/v (40 mg/ml) | 6.00 |
| DCM 100% (40 mg/ml) | 2.95 |

Figure 6:
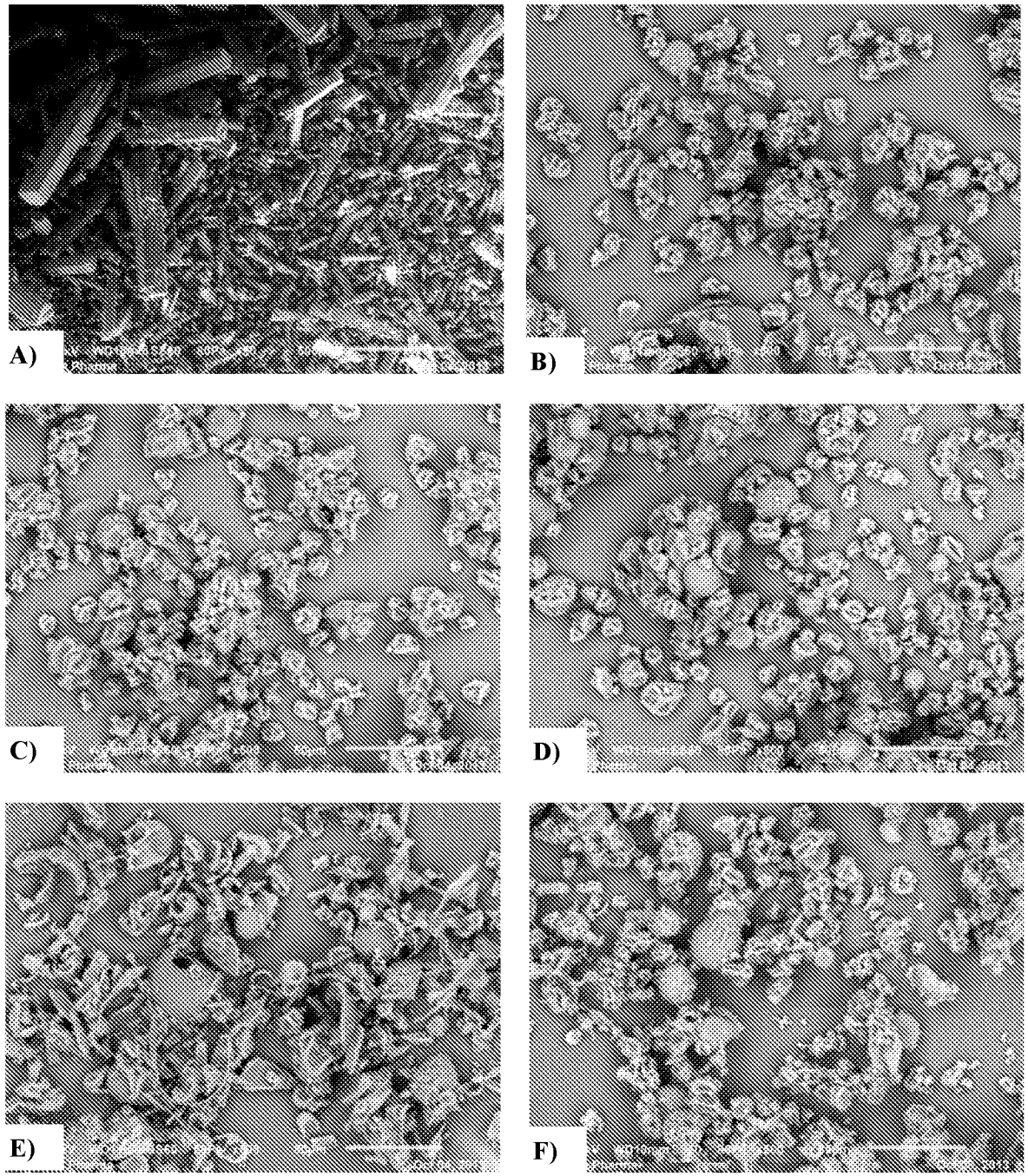
FIG. 6 shows SEM micrographs of A) Fenretinide lot C00324 (as received, reference), Fenretinide/PKV K30 40/60% w/w lots: B) L215-01009A, C) L215-01009B, D) L215-01009C, E) L215-01010 and F) L215-01011 at 500×.
Figure 7:
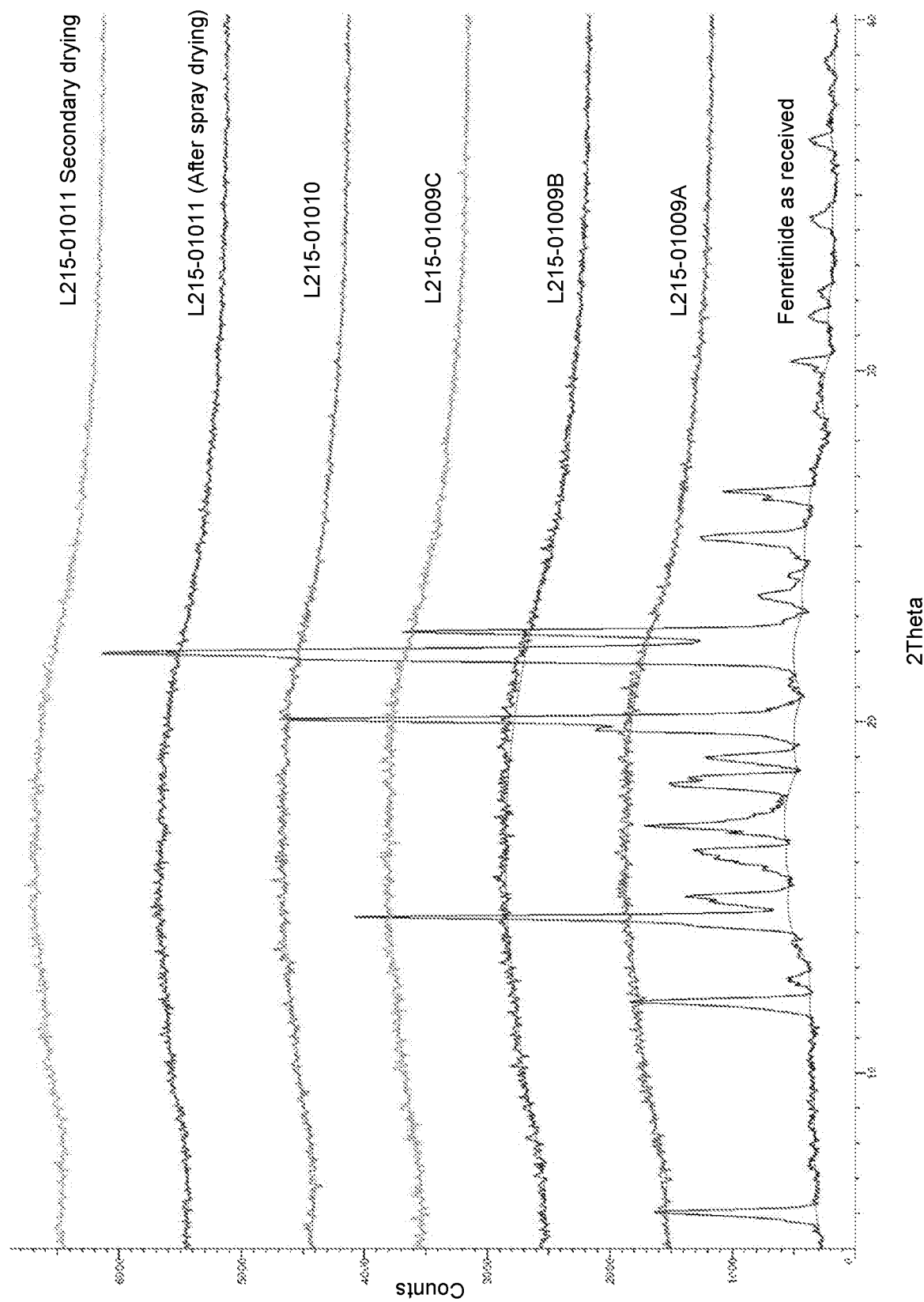
FIG. 7 shows XRPD diffractograms of Fenretinide/PVP K30 40/60% w/w SDI lots L215-01009 to L215-01011. Fenretinide lot C00324 (as received) as reference.
Figure 8:
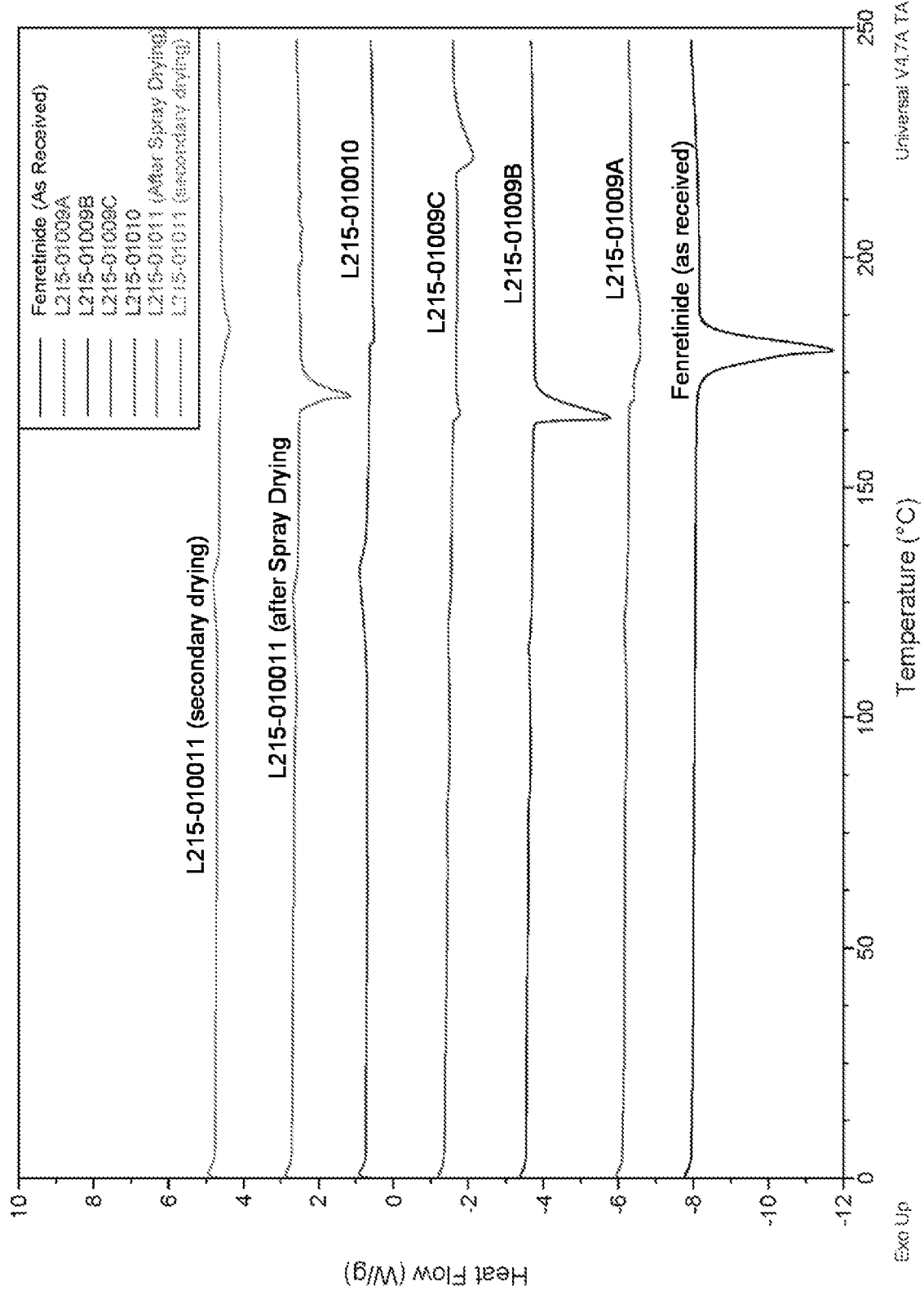
FIG. 8 shows a DSC thermogram of Fenretinide/PVP K30 40/60% w/w SDI lots L215-01009 to L215-01011. Fenretinide lot C00324 (as received) as reference.
Figure 9:
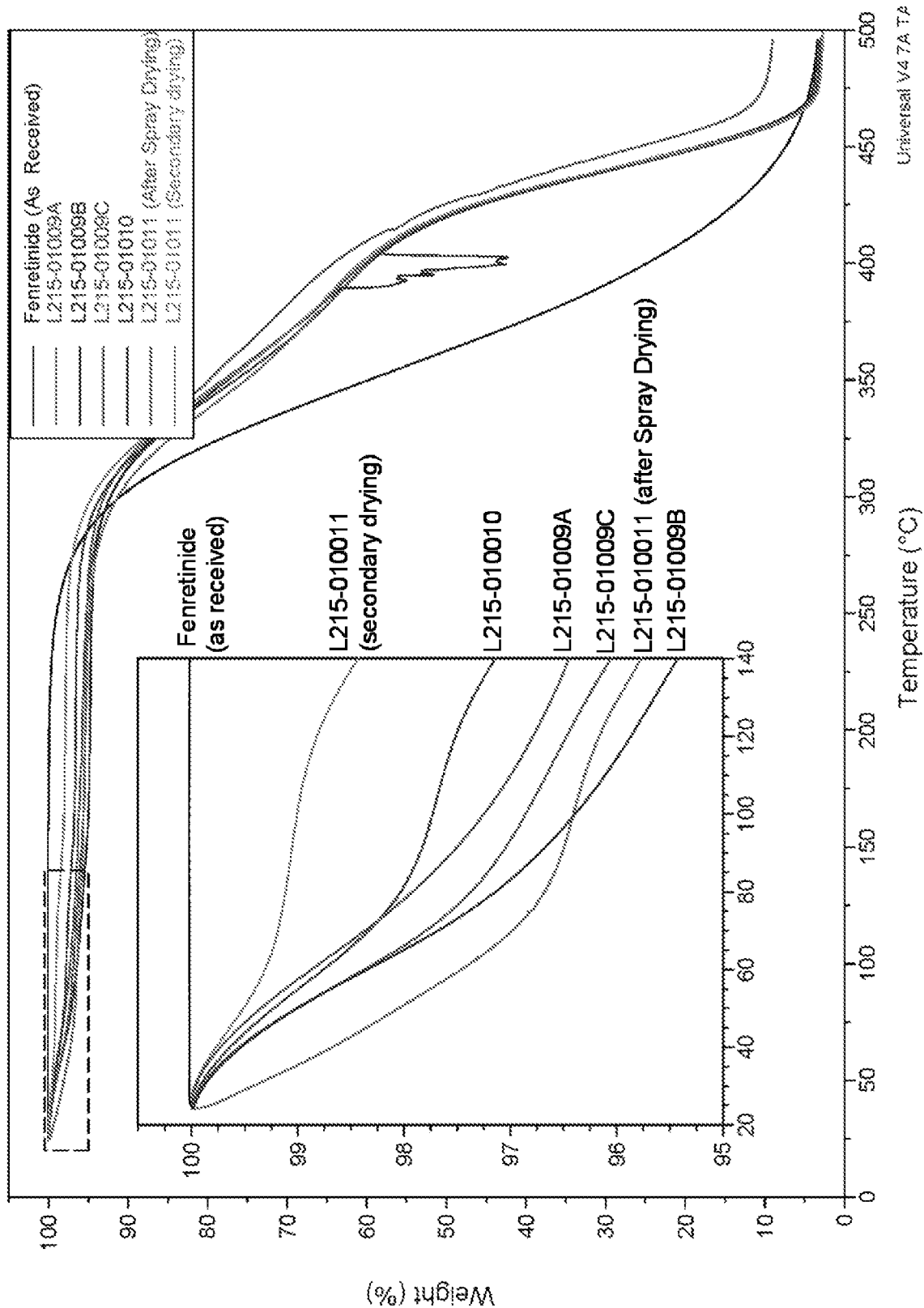
FIG. 9 shows a TGA thermogram of Fenretinide/PVP K30 40/60% w/w SDI lots L215-01009 to L215-01011. Fenretinide lot C00324 (as received) as reference.

At lower solid loading (7.5% w/w), the influence of DCM on the viscosity of the solution was lower as shown by lots L215-01009A, B and C (Table 29). For these lots, it was found that the yield of the spray-drying process increases with increasing ratio of DCM in solution. A significant amount of volatile compounds (between 3.13 and 4.24%) was present in the SDI (FIG. 9). GC analysis showed that in all samples, ethanol and DCM was among the volatile compounds (Table 29). The remaining volatile compound was probably water. The residual amount of DCM in the SDI varied also with the ethanol/DCM ratio, a higher ratio of DCM in the solution resulted in higher amounts of DCM in the SDI. High level of ethanol was found in all SDI of lot L215-01009 (Table 29). The higher amount of ethanol found in the lots L215-01009B and C compared to the lot L215-01009A probably resulted from the lower inlet temperature used to produce the SDI lots L215-01009B and C. FIGS. 6B-D show that the DCM/ethanol ratio had a limited influence on the SDI particle morphology. Most of the particles were irregular shapes and appeared as collapsed sphere, but slightly more spherical particles with smooth surface was observed within the SDI of lot L215-01009C. The DCM/ethanol ratio did not influenced the crystal state of the SDI, where for the lots L215-01009A, B and C amorphous material was produced (FIG. 7). No thermal event, particularly no glass transition, before 150° C. was identified on the DSC thermogram of the SDI lots L215-01009A, B and C suggesting a stability of the amorphous state at under normal temperature condition used for dry granulation and encapsulation process (FIG. 8). According to these results, it was selected to use DCM only for the spray dry solution for further development.

With DCM only as solvent, it was possible to increase the solid loading up to 20%. At this solid loading, the viscosity of the solution of lot L215-01010 was high (Table 29) and more difficult to spray. The atomization of the solution was incomplete causing sticking of material on the inside wall of the drying chamber and filament like particle (FIG. 6E). Despite these facts, the spray drying yield of the lot L215-01010 was comparable to the lot L215-01009C. The SDI of lot L215-01010 was also in an amorphous state (FIG. 7), no thermal event before 150° C. was observed on its DSC thermogram (FIG. 8) and about 2.5% of volatile compounds was release from the SDI when heated up to 125° C. (FIG. 9).

To improve the SDI particle morphology, the solid loading in the solution was decreased to 12.5% for the lot L215-01011. FIG. 6F shows that at this solid loading, particle with morphology similar to that of lot L215-01009 was obtained. As previously, the SDI of the lot L215-01011 was in an amorphous state (FIG. 7), and had similar thermal properties to the lots L215-01009 and L215-01010 (FIGS. 8 and 9). With increase batch size, 250 g, the maximum spray drying yield among the spray drying trials was achieved with the lot L215-01011 (Table 29). The increase batch size was also associated with an increase of the residual amount of dichloromethane in the SDI (Table 29), which was easily removed by the secondary drying at RT and under −15 inHg vacuum where after 16 hours, the totality of the DCM was almost removed (Table 29). The secondary drying did not modify the amorphous sate of the SDI (FIG. 7). The SDI lot L215-01011 was characterized by an assay value of 96.3% and with a low level of related substance (0.43%) (Table 31). The composition of the lot L215-01011 and the process parameters used to produce it are thus recommended for CTM manufacturing of Fenretinide.

TABLE 29

Fenretinide/PVP K30 40/60% w/w SDI Process Related Data

| Lot | Viscosity (mPas) | Spray Drying Yield (%) | Residual Solvent (ppm) |
|---|---|---|---|
| L215-01009A | 3.72 | 72.3 | EtOH: 3 687 DCM: 63 |
| L215-01009B | 3.43 | 79.0 | EtOH: 5 805 DCM: 500 |
| L215-01009C | 2.88 | 86.0 | EtOH: 4 586 DCM: 2 539 |
| L215-01010 | 10.2 | 89.6 | DCM: 8 619 |
| L215-01011 | 3.42 | 95.3 | DCM: 13 616 DCM: 19* |

*After secondary drying.

SDI Direct Encapsulation

Figure 10:
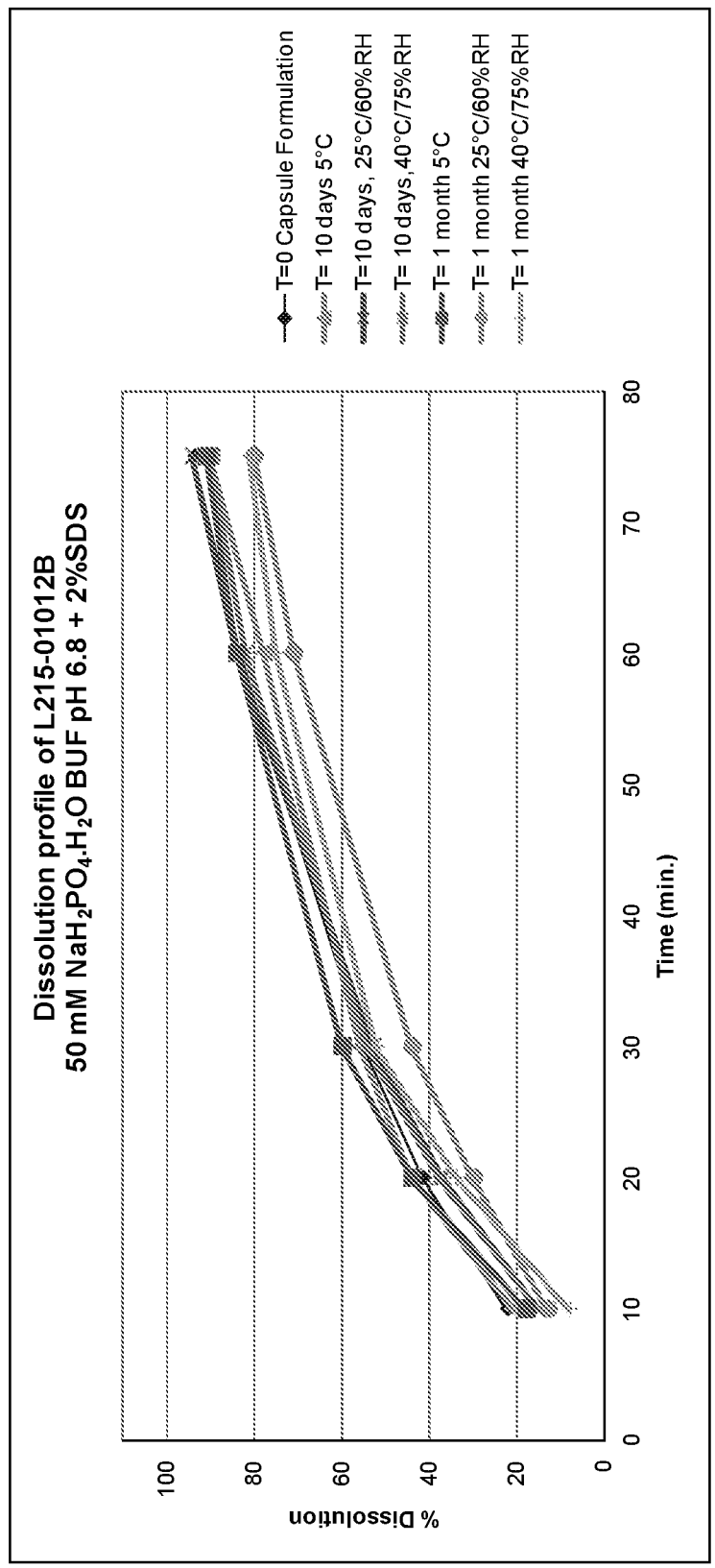
FIG. 10 shows the dissolution profile of L215-01012B capsule formulation incubated at 5° C., 25° C./60% RH and 40° C./75% RH closed cap for up to 1 month.

Uniform final blend was obtained for lots L215-01012A and L215-01012B. The encapsulation of both lots involved to force with a moderate pressure the final blend inside the capsule bodies with stainless steel tamping pin to reach the desired capsule weight. The capsule fill weight of lot L215-01012B was slightly over the target weight (Table 30) resulting in assay value of 101% (Table 32). Compared to lot L215-01007 (Table 19), the Fenretinide dissolution from the capsule of lot L215-01012B in pH 6.8+2% SDS (Table 33 and FIG. 10) was slower but higher plateau value was reached. These results indicated that a dry granulation step is not necessary to produce Fenretinide 100 mg capsule based on Fenretinide/PVP K30 40/60% w/w SDI. To reduce stress on the SDI, simplify process and maximize process throughput, direct encapsulation is thus preferred for CTM manufacturing.

TABLE 30

Fenretinide 100 mg HGC Direct Encapsulation Formulation
lot L215-01012B (n = 100) and Fenretinide Placebo
Formulation lot L215-01013P (n = 16) Fill Weight Statistics

| Lot | Fill weight Ave. (mg) | Stdev (mg) | RSD (%) | Min. (mg) | Max. (mg) |
|---|---|---|---|---|---|
| L215-01012B | 463.5 | 6.0 | 1.3 | 445.9 | 475.8 |
| L215-01013P | 449.2 | 4.5 | 1.0 | 436.9 | 455.9 |

Short Term Stability Study

Tables 34 and 35 present the appearance, moisture, assay and total related substance in SDI lot L215-01011 and Fenretinide 100 mg HCG lot L215-01012B incubated with closed cap at 5° C., 25° C./60% RH and 40° C./75% RH after 1 month and 9 months. The dissolution profile of lot L215-01012B is presented in Table 33 and in FIG. 10.

Figure 14:
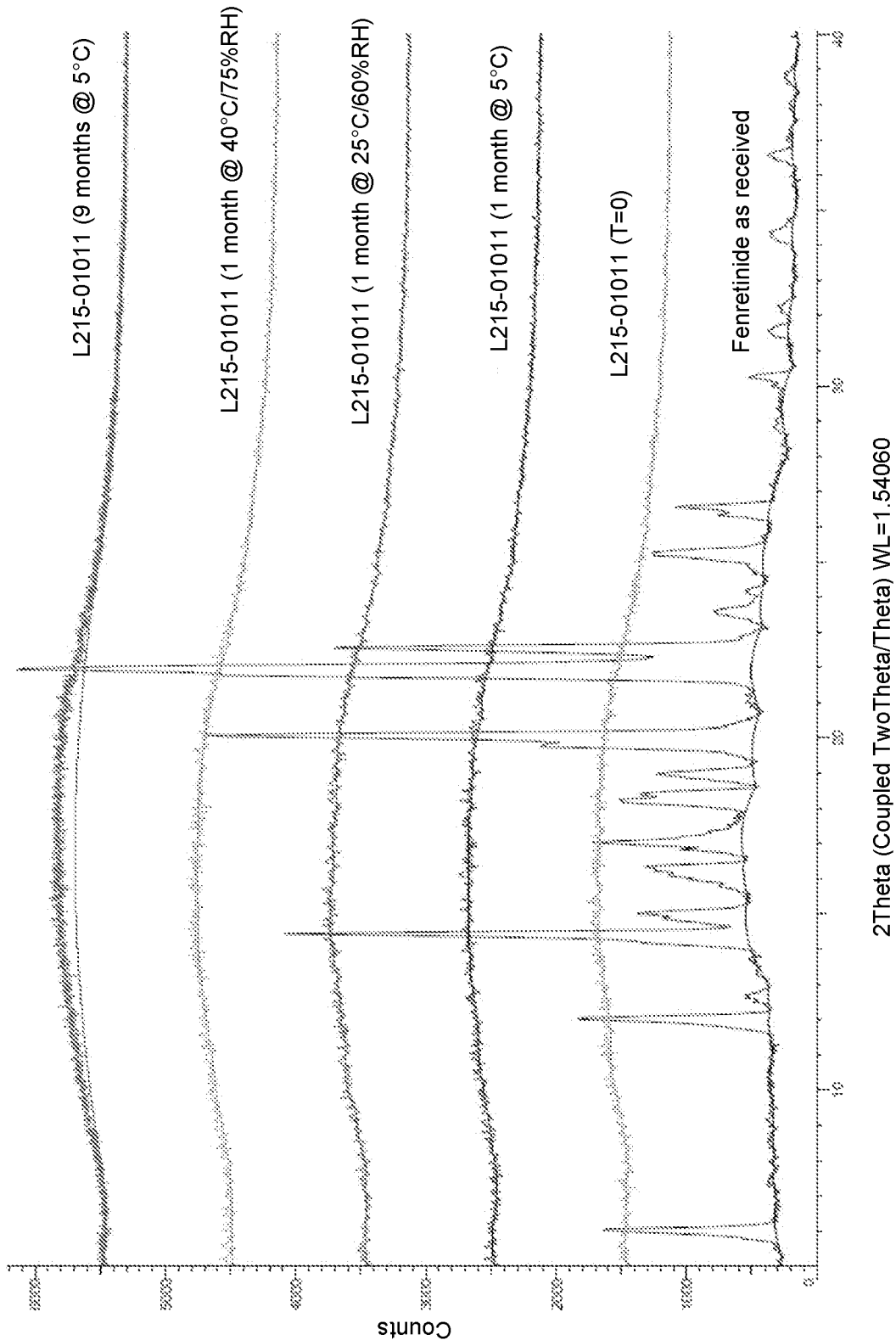
FIG. 14 shows XRPD diffractograms of Fenretinide/PVP K30 40/60% w/w SDI lot L215-01011 incubated at 5° C., 25° C./60% RH and 40° C./75% RH. Fenretinide lot C00324 (As Received) as Reference.

After an incubation of 1 month no modification of the sample's appearance was noticed. At each time point, the moisture content was similar in all samples irrespectively of the incubation condition and remained under 5%, suggesting that the addition of moisture protection with the product may not be necessary when stored in a sealed HDPE bottle. Stability of amorphous forms was maintained for 1 month under all 3 conditions of temperature and humidity and remained stable even after 9 months of incubation at 5° C. (FIG. 14).

Non-refrigerated samples (25° C./60% RH and 40° C./75% RH) showed a decrease of the assay value associated with the increase of the amount of related substance over time. For samples stored at 5° C., assay was of 96%, remaining as previous time-point and the total amount of related substances increased by 0.24%. However, further degradation during subsequent storage (9 months) occurred with a total amount of related substances of 8.36% area and largest impurity 2.85% area.

Figure 11:
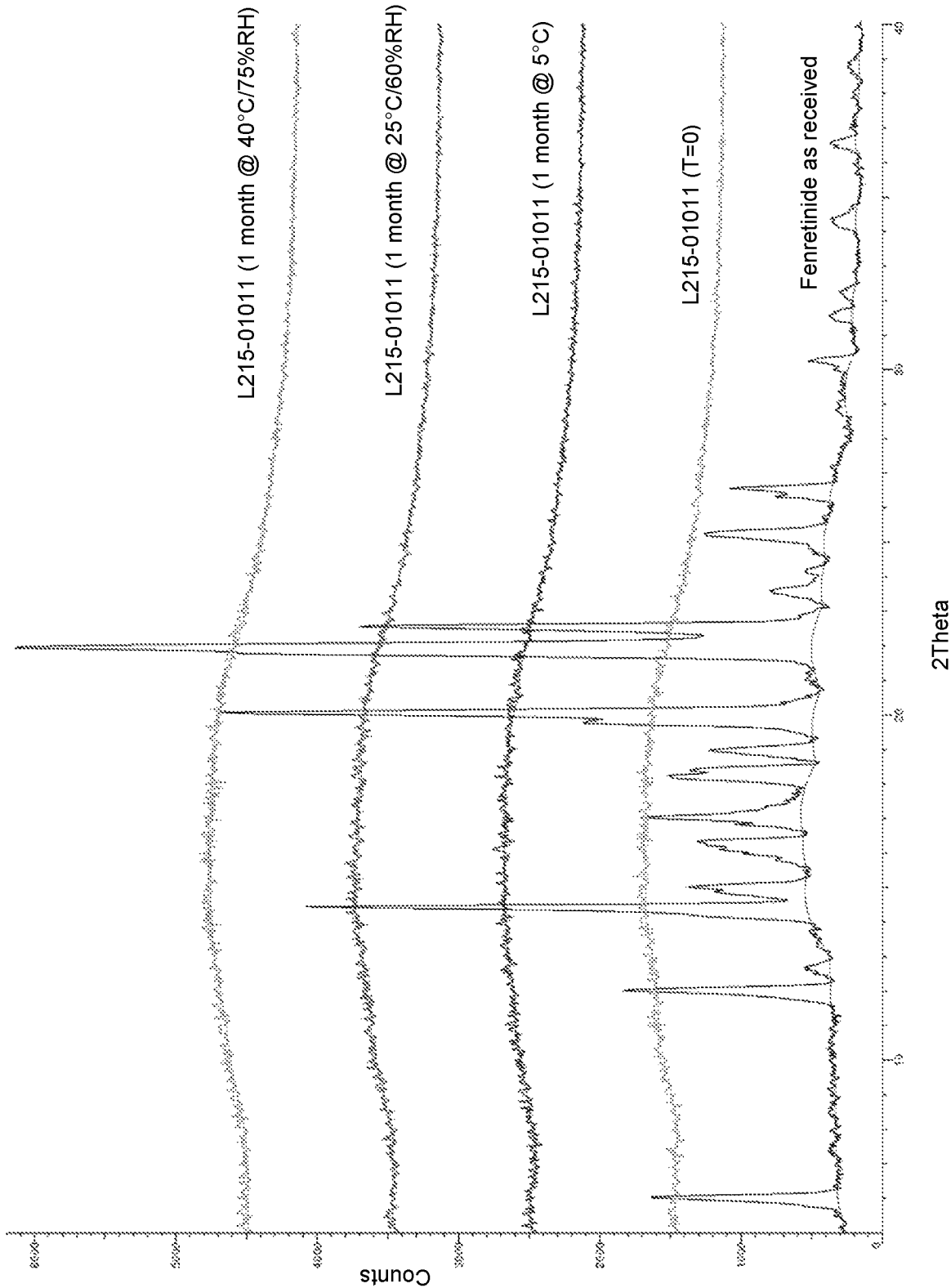
FIG. 11 shows XRPD diffractograms of Fenretinide/PVP K30 40/60% w/w SDI lot L215-01011 incubated at 5° C., 25° C./60% RH and 40° C./75% RH closed cap for 1 month. Fenretinide lot C00324 (as received) as reference.
Figure 12:
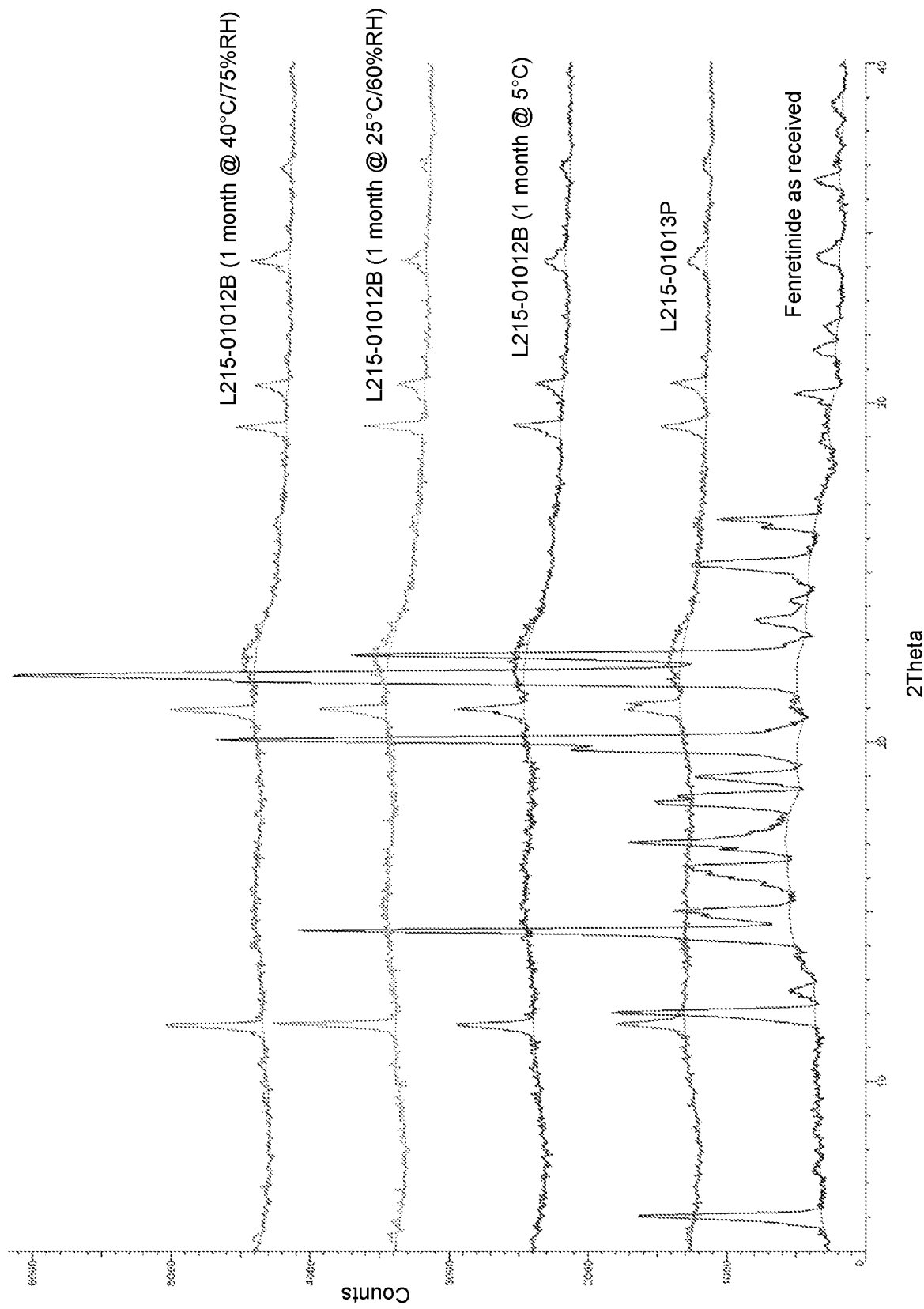
FIG. 12 shows XRPD diffractograms of Fenretinide 100 mg HGC lot L215-01012B incubated at 5° C., 25° C./60% RH and 40° C./75% RH closed cap for 1 month. Fenretinide lot C00324 (as received) and Placebo Capsule lot L215-01013P as reference.

FIGS. 11 and 12 show that the amorphous form of Fenretinide remained stable even after a 1-month incubation at 40° C./75% RH. As shown by the slope of the dissolution profiles of the L215-01012B samples (FIG. 10), the dissolution rate of Fenretinide did not appear to be influenced by the decreased of the assay value suggesting a certain level of robustness for the direct encapsulation approach.

TABLE 31

Assay and Related Substances for SDI lot L215-01011 Incubated at 5° C., 25° C./60% RH and 40° C./75% RH

| Sample | | L215-01011 SDI Fenretinide/PVP K30 | | |
|---|---|---|---|---|
| Dose strength | | 40% Drug load | | |
| | | 5° C. | 25° C./60% RH | 40° C./75% RH |
| Appearance | T = 10 days | Yellow fine powder | Yellow fine powder | Yellow fine powder |
| | T = 1 month | Yellow powder | Yellow powder | Yellow powder |
| | T = 9 months | Yellow powder | N/A | N/A |
| | | 5° C. | 25° C./60% RH | 40° C./75% RH |
| Moisture (KF) | T = 10 days | 2.7% | 2.7% | 2.9% |
| | T = 1 month | 3.2% | 3.0% | 3.5% |
| | T = 9 months | 2.9% | ND | ND |
| Assay | T = 0 | 96.3% (n = 2: 94.0, 98.7) | | |
| | | 5° C. | 25° C./60% RH | 40° C./75% RH |
| | T = 10 days | 96.2% (n = 2: 97.2, 95.3) | 93.1% (n = 2: 93.2, 93.1) | 73.2% (n = 2: 72.9, 73.4) |
| | T = 1 month | 96.0% (n = 2: 96.4, 95.7) | 77.4% (n = 2: 77.3, 77.6) | 54.1% (n = 2: 54.2, 53.9) |
| | T = 9 months | 72.7% (n = 2: 72.4, 73.0) | N/A | N/A |
| Related Substances (% area) | T = 0 | Total: 0.43% area Largest impurity: 0.15% area @ RRT 0.72 | | |
| | | 5° C. | 25° C./60% RH | 40° C./75% RH |
| | T = 10 days | Total: 0.95% area Largest impurity: 0.37% area @ RRT 0.22 | Total: 1.52% area Largest impurity: 0.55% area @ RRT 0.27 | Total: 7.68% area Largest impurity: 2.39% area @ RRT 0.27 |
| | T = 1 month | Total: 1.19% area Largest impurity: 0.38% area @ RRT 0.27 | Total: 7.35% area Largest impurity: 2.40% area @ RRT 0.27 | Total: 17.92% area Largest impurity: 4.69% area @ RRT 0.27 |
| | T = 9 months | Total: 8.36% area Largest impurity: 2.85% area @ RRT 0.27 | N/A | N/A |

RRT = relative response time

TABLE 32

Assay and Related Substances for Fenretinide 100 mg HGC lot L215-01012B Incubated at 5° C., 25° C./60% RH and 40° C./75% RH Closed Cap for 1 Month

| | | Sample L215-01012B SDI (40% PVP dry granulation Croscarmellose + Emcompress ® dehydrate (size 00 Capsule)) | | |
|---|---|---|---|---|
| Dose strength | | 100 mg/capsule | | |
| | | 5° C. | 25° C./60% RH | 40° C./75% RH |
| Appearance | T = 10 days | Two piece orange capsules | Two piece orange capsules | Two piece orange capsules |
| | T = 1 month | Yellow powder inside orange capsule | Yellow powder inside orange capsule | Yellow powder inside orange capsule |
| | | 5° C. | 25° C./60% RH | 40° C./75% RH |
| Moisture (KF) | T = 10 days | 3.1% | 3.3% | 3.5% |
| | T = 1 month | 3.75 | 4.1% | 4.7% |
| Assay | T = 0 | 101.0% (n = 2: 101.5, 100.6) | | |
| | | 5° C. | 25° C./60% RH | 40° C./75% RH |
| | T = 10 days | 98.5% (n = 2: 98.1, 98.9) | 94.5% (n = 2: 93.3, 95.8) | 92.1% (n = 2: 92.0, 92.2) |
| | T = 1 month | 96.6% (n = 2: 96.7, 96.5) | 87.5% (n = 2: 87.5, 87.5) | 83.7% (n = 2: 83.7, 83.6) |
| Related Substances (% area) | T = 0 | Total: 0.40% area Largest impurity: 0.18% area @ RRT 0.72 | | |
| | | 5° C. | 25° C./60% RH | 40° C./75% RH |
| | T = 10 days | Total: 0.84% area Largest impurity: 0.19% area @ RRT 0.72 | Total: 1.90% area Largest impurity: 0.54% area @ RRT 0.50 | Total: 2.30% area Largest impurity: 0.68% area @ RRT 0.49 |
| | T = 1 month | Total: 1.79% area Largest impurity: 0.41% area @ RRT 0.27 | Total: 5.63% area Largest impurity: 1.43% area @ RRT 0.27 | Total: 6.91% area Largest impurity: 1.81% area @ RRT 0.49 |

RRT = relative response time

TABLE 33

Dissolution for lot L215-01012B Incuvated at 5° C., 25° C./60% RH and 40° C./75% RH Close Cap for up to 1 Month

| Sample | | L215-01012B SDI (40% PVP) dry granulation Croscarmellose + Emcompress dehydrate (size 00 Capsule) | | | | | |
|---|---|---|---|---|---|---|---|
| Dose strength | | 100 mg/capsule | | | | | |
| | | Time (minutes) | % Dissolved | | | | |
| Dissolution Paddles, 100 rpm ramp to 200 rpm at 60 minutes 900 ml pH 6.8 + 2% SDS | T = 0 (n = 3) | 10 | 22 | | | | |
| | | 20 | 42 | | | | |
| | | 30 | 55 | | | | |
| | | 60 | 83 | | | | |
| | | 75 | 94 | | | | |
| | | 5° C. | | 25° C./60% RH | | 40° C./75% RH | |
| | | Time (minutes) | % Dissolved | Time (minutes) | % Dissolved | Time (minutes) | % Dissolved |
| | T = 10 days | 10 | 21 | 10 | 15 | 10 | 15 |
| | | 20 | 44 | 20 | 37 | 20 | 38 |

TABLE 33-continued

Dissolution for lot L215-01012B Incuvated at 5° C., 25° C./60% RH and 40° C./75% RH Close Cap for up to 1 Month

| | | | | | | |
|---|---|---|---|---|---|---|
| (n = 3) | 30 | 56 | 30 | 53 | 30 | 54 |
| | 60 | 78 | 60 | 84 | 60 | 82 |
| | 75 | 90 | 75 | 94 | 75 | 90 |
| T = 1 | 10 | 18 | 10 | 13 | 10 | 8 |
| month | 20 | 44 | 20 | 30 | 20 | 34 |
| (n = 2) | 30 | 60 | 30 | 44 | 30 | 52 |
| | 60 | 84 | 60 | 71 | 60 | 75 |
| | 75 | 91 | 75 | 80 | 75 | 81 |

Example 8: Further Optimization of the Solid Fenretinide Dispersion

Table 34 provides a description of the materials used in this study.

TABLE 34

| Material (Commercial Name) | Lot # | Supplier |
|---|---|---|
| Fenretinide | C00324 | Cedarburg |
| Povidone (Plasdone K-29/32) PVPK30 | C00450 | ISP |
| Povidone (Plasdone K-12) PVPK12 | 0001596798 | Ashland |
| Hydroxypropyl methylcellulose acetate succinate (HPMCAS) | 2103280 | Shin-Etsu |
| Butylated hydroxyanisole (BHA) | C00473 | A&C |
| Butylated hydroxytoluene (BHT) | C00474 | A&C |
| Dichloromethane HPLC grade | 53130 | EMD |
| Methanol HPLC grade | 54702 | EMD |
| Microcrystalline cellulose (Avicel PH-102) | C00537 | FMC |
| Dibasic Calcium Phosphate Dihydrate (Emcompress) | C00084 | JRS |
| Croscarmellose Sodium (Solutab Type A) | C00020 | Blanver |
| Acid ascorbic | 20747096 | A&C |
| Magnesium Stearate Vegetal grade MF-2-V | C00124 | Peter Greven |
| Opadry AMB II 88A180040 white | WP740303 | Colorcon |
| Empty Hard Gelatin Capsules, Size 00, CS, Orange Opaque | C00159 | Capsugel |

Solid dispersions or Spray-Dried Intermediates of Fenretinide were obtained by spray drying technique (Tables 35 and 36).

Preparation of Solution:

The solutions were prepared by dissolving the powders in 400 ml of a solvent system (50:50% v/v of methanol/dichloromethane) at 5% of solids. The mixtures were stirred until all particles were dissolved.

Spray-Drying:

The solutions were processed using a Model GA32 Yamato™ Lab Spray Dryer with the following operating parameters: internal nozzle diameter 711 μm; between 15-20 ml/min feed rate; 65° C. inlet temperature; 35-40° C. outlet temperature; 1.5 kg/cm² atomization air, and 0.45 m³/min air flow. After spraying, the heating was stopped and the drying was continued for an additional 3 minutes at an outlet temperature less than 45° C. The SDIs were collected in the receiving flask (after cyclone) for yields of 62-71%. Also, the samples were protected from light during all steps of the formulation development and stored at −20° C. until use.

TABLE 35

With/Without Antioxidants PVP and HPMCAS based Fenretinide SDI Formulations (20 g of solids/lot)

| | Lot No. | | | | |
|---|---|---|---|---|---|
| Ingredients | L215-01016 | L215-01017 | L215-01018 | L215-01019 | L215-01020 |
| Fenretinide | 100.0% | 40.0% | 40.0% | 40.0% | 40.0% |
| Povidone, type K-29/32 | — | 60.0% | 59.8% | — | — |
| HPMCAS | — | — | — | 60.0% | 59.8% |
| BHA | — | — | 0.1% | — | 0.1% |
| BHT | — | — | 0.1% | — | 0.1% |
| MeOH-DCM (1:1 v/v) | 400 ml | 400 ml | 400 ml | 400 ml | 400 ml |
| Total solid phase: | 100% | 100% | 100% | 100% | 100% |

Lots L215-01021 and 022 are the placebos for the lots L215-01018 and 020, respectively.

A new series of Fenretinide SDIs (Table 36) was prepared using increased amount of antioxidants and two different grades of Povidone (PVPK30 and K12) as polymer. The modifications were based on improved stability results obtained for lot L215-01018.

Preparation of Solution:

The solutions were prepared by dissolving the powders in 400 ml of a single solvent (dichloromethane) at 5% of solids. The mixtures were stirred until all particles were dissolved.

Spray-Drying:

The solutions were processed using a Model GA32 Yamato™ Lab Spray Dryer with the following operating parameters: internal nozzle diameter 711 μm, about 10 ml/min feed rate; 60° C. inlet temperature; 31-40° C. outlet temperature; 1.5 kg/cm² atomization air, and 0.5 m³/min air flow. The SDI yield on receiving flask (after cyclone) were improved between 76-83%.

Drug Products (DP)

Based on improved purity results, SDI lots L215-01023 and 027 were chosen to prepare Fenretinide 100 mg capsules and tablets (Tables 37 and 38). Tablets were also coated with polyvinyl alcohol (PVA) based moisture barrier film coating at 10% weight gains (Opadry™ AMB II 88A180040 white).

Final blends were obtained by dry granulation—slugging method. First powders were sieved with a 30-mesh screen and mixed using a PK V-blender for 5 minutes at 25 RPM and 2 additional minutes after addition of the lubricant (magnesium stearate). The compacts (slugs) were produced using a Carver single punch laboratory press with 12 mm die and punches combination at 2-3 kP hardness. The granules were formed by crushing and passing compacts through an 850 μm (20-mesh) screen.

475 mg dose was obtained by filling the granules into size 00 capsules using a Cooper filling capsule device. The tablets were compressed with Globe Pharma™ Rotary Press using caplet shaped tooling 6.05×17.75 mm. Half quantity of the core tablets were coated with 10% weight gain of Opadry™ AMB aqueous moisture barrier film coating system (20% solids) using an Aeromatic Strea™ fluid bed equipped with Wurster column and bottom spray nozzle system. The coating was carried out at inlet temperature 50-60° C., outlet temperature 45-50° C., spray rate 3-5 g/min, atomization pressure 1.4-1.6 bars, Airflow 110-130 m³/h.

Characterization (XRPD, TGA, stability) was performed as described above.

Stability—crystalline API (lot C00324) and amorphous SDI. The crystalline API (lot C00324) and amorphous SDI powders, lots L215-01016 to 020 were stored at 5° C., 25° C./60% RH and 40° C./75% RH in amber closed and open bottles. The closed bottles were placed in double PE bags tightly closed and containing oxygen scavenger (StabilOx®) (1 unit) and desiccant (MiniPax® Sorbent Packets, 2 units), followed by aluminum seal.

Stability—amorphous SDI vs. Drug products. SDI powders (about 0.6 gram), lots L215-01023 to 027 and 100 mg Fenretinide drug product formulations lots L215-01028 to 033 were stored at 5° C. and 25° C./60% RH in Uline Poly bags closed and containing desiccant (MiniPax® Sorbent Packets, 2 units), followed by aluminum seal (2× Statshield® moisture barrier bags with Nitrogen purge).

Figure 15:
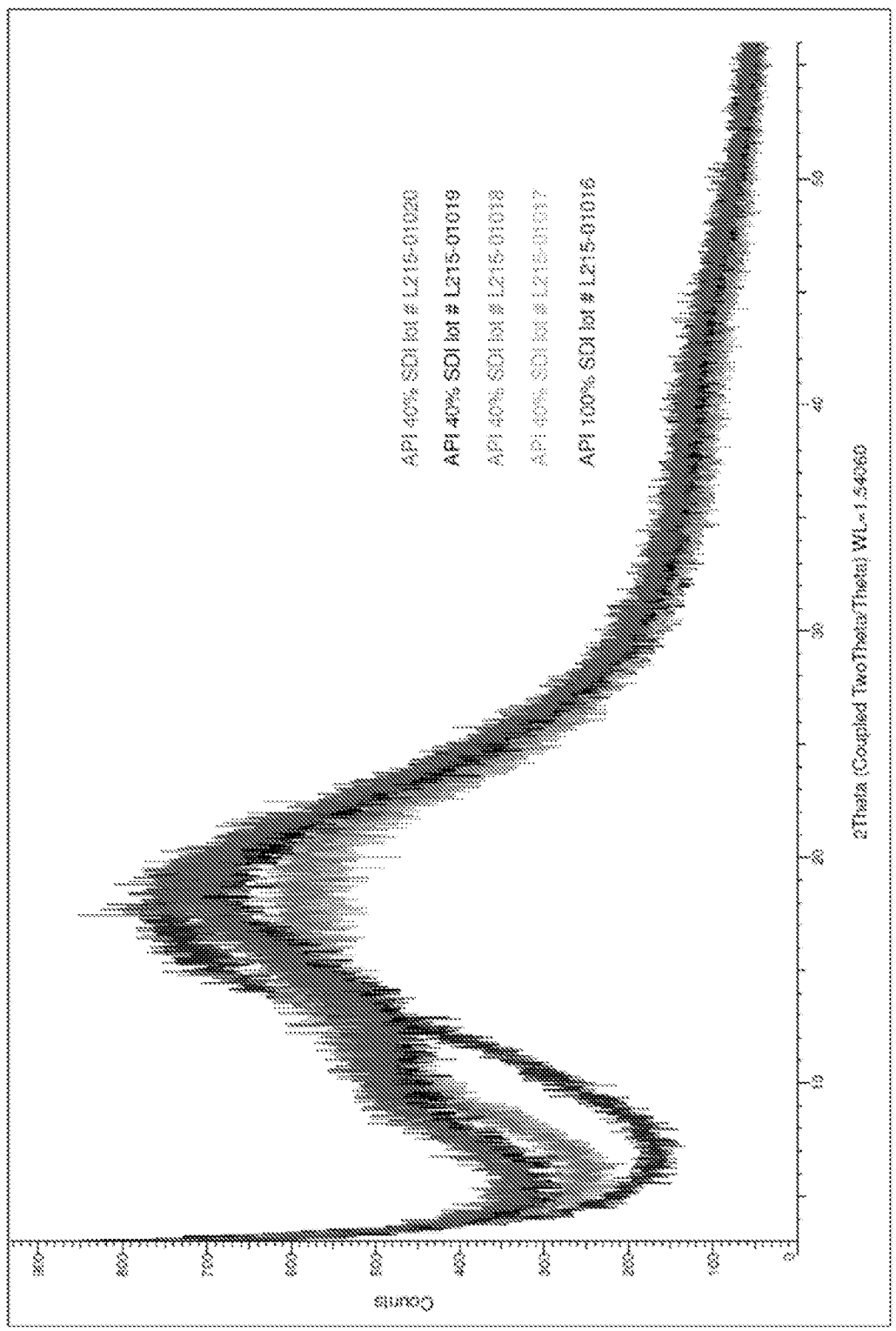
FIG. 15 shows XRPD diffractograms of Fenretinide SDI lots L215-01016 to L215-01020.
Figure 16:
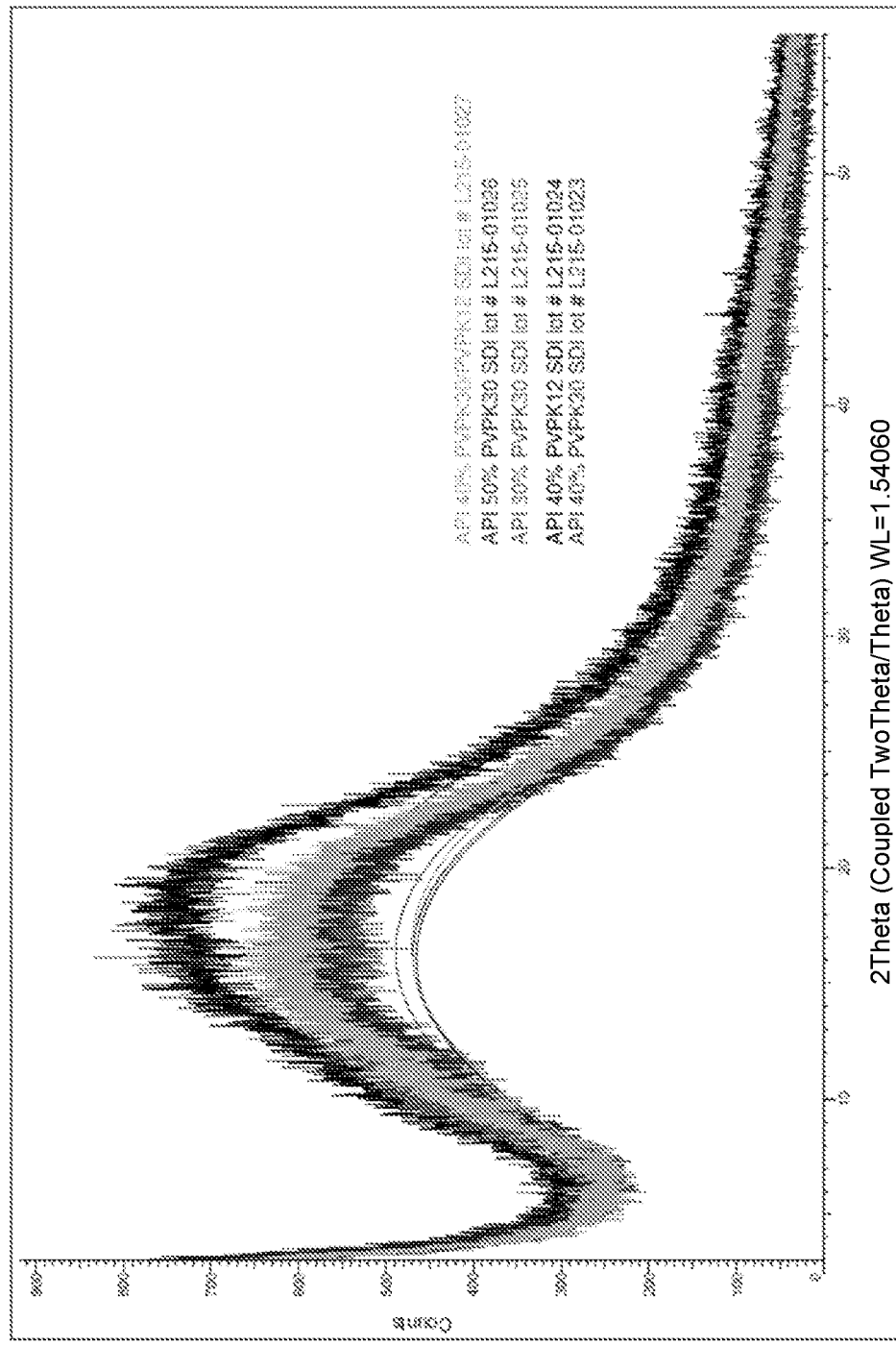
FIG. 16 shows XRPD diffractograms of Fenretinide SDI lots L215-01023 to L215-01027.

Fenretinide, PVP, BHA and BHT are all very soluble in a mixture of methanol/dichloromethane (1:1) as well as in pure dichloromethane. As results, clear solutions of API (lot L215-01016) as well as API/PVP samples (lot L215-01017) and API/PVP/BHA/BHT (L215-01018 and 023 to 027) were obtained rapidly. Formulations containing HPMCAS resulted in a turbid slightly viscous liquid. Irrespective of the formulation, amorphous form of Fenretinide was produced by spray drying for all lots with a typical amorphous halo XRPD diffraction pattern (FIGS. 15 and 16).

The amount of volatile components (residual dichloromethane and methanol from spray-drying process) was determined by TGA. Amorphous API (lot L215-01016) and API/HPMCAS SDIs (lots L215-01019 and 020) showed less than 1% of volatile components content. PVP containing SDIs (lots L215-01017 and 018) showed an increase at 4.2% of volatile content that could be a result of the water content or residual solvent affinity with PVP. Identification and quantification of volatile compounds could be obtained by gas chromatography. For spray drying of lots L215-01023 to 027, pure dichloromethane was used as a solvent, the drying temperature of 60-65° C., spray rate of about 10 ml/min and drying time after spraying was between 5-7 minutes. Under these conditions TGA showed a mass loss of 1.77-3.65% between RT and 100° C. lower than previous PVP containing SDIs (lots L215-01017 and 018) prepared with dichloromethane/methanol solvents.

Stability #1 (API vs SDI)—Lots L215-01016 to 020

SDIs were tested for assay and related substances and compared with amorphous and crystalline API. Initial results obtained are shown in Table 39. The amorphous API (lot L215-01016) showed lower assay and increased amount of related substances when compared with un-processed crystalline form (99.2% and 0.25%, respectively). However, when using a stabilizing polymer, the amount of related substances for SDIs lots L215-01017 and L215-01019 were lower when compared to the pure API amorphous form. The addition of antioxidants within the SDIs further increased stability (L215-01018 and L215-01020). Stability was investigated after 1 and 3 months under 5° C., 25° C./60% RH and 40° C./75% RH (open and closed cap glass amber bottles). The results are also shown in Table 39. Antioxidants appear to prevent or retard degradation for samples stored under 5° C. and 25° C./60% RH open cap. SDI lots L215-01017 and L215-01018 based on Plasdone™ showed less degradation than the SDI lots using HPMCAS.

Stability #2 (SDI vs DP)—Lots L215-01023 to 033

Five new Fenretinide SDI formulations were produced based on most stable lot L215-01018 (API, PVP as polymer and BHA+BHT as antioxidants) but using dichloromethane as single solvent. Drug loading ranging from 30 to 50% and the use of 2 grades of Plasdone™ K12 and K30 were evaluated. Initial testing results (Table 40) did not show major differences between SDIs and also compared with the raw crystalline API. However, lots L215-01023 and 026 showed the highest assay values and yields and lowest water content and total related substances. These results confirmed the suitability of the 40% drug loading using both PVP K30 and PVP K12 along with BHA and BHT as antioxidants.

Stability of lots L215-01023 to 27 was investigated after 1 and 3 months under 5° C. and 25° C./60% RH, and at 6 months under 5° C., in closed containers. The results are shown in Table 41. Stability of formulations lots L215-01028 to 33 was also assessed under the same conditions. The results are shown in Table 42.

TABLE 42

Summary Results for Assay and Related Substances for Drug Products lots L215-01028 to 33 at T = 0, after 1 month, 3 months and 6 months

| | L215-01028 L215-01023 SDI Fenretinide 40%- PVPK30/BHA/BHT SDI | L215-01029 L215-01023 SDI Fenretinide 40%- PVPK30/BHA/BHT SDI | L215-01030 (L215-01029 core) | L215-01031 L215-01027 SDI Fenretinide 40%- PVPK30/PVPK12/ BHA/BHT SDI | L215-01032 L215-01027 SDI Fenretinide 40%- PVPK30/PVPK12/ BHA/BHT SDI | L215-01033 (L215-01032 core) |
|---|---|---|---|---|---|---|
| | | | Description | | | |
| | Orange capsule filled with yellow powder | Yellow uncoated tablet | White coated tablet | Orange capsule filled with yellow powder | Yellow uncoated tablet | White coated tablet |
| Storage | | | T = 0 | | | |
| Total deg (% area) | 0.47 | 0.44 | 0.49 | 0.47 | 0.50 | 0.55 |
| Total Deg in SDI (% area) | | | 0.33 | | | 0.43 |
| Assay (% LC) | 97.7 | 95.9 | 90.2 | 98.9 | 96.5 | 84.0 |

TABLE 42-continued

Summary Results for Assay and Related Substances for Drug Products lots
L215-01028 to 33 at T = 0, after 1 month, 3 months and 6 months

| | L215-01028 L215-01023 SDI Fenretinide 40%- PVPK30/BHA/BHT SDI | L215-01029 L215-01023 SDI Fenretinide 40%- PVPK30/BHA/BHT SDI | L215-01030 (L215-01029 core) | L215-01031 L215-01027 SDI Fenretinide 40%- PVPK30/PVPK12/ BHA/BHT SDI | L215-01032 L215-01027 SDI Fenretinide 40%- PVPK30/PVPK12/ BHA/BHT SDI | L215-01033 (L215-01032 core) |
|---|---|---|---|---|---|---|
| | | | Description | | | |
| | Orange capsule filled with yellow powder | Yellow uncoated tablet | White coated tablet | Orange capsule filled with yellow powder | Yellow uncoated tablet | White coated tablet |
| Storage | | | T = month 5° C. | | | |
| Total deg (% area) | 0.71 | 0.72 | 0.78 | 0.75 | 0.76 | 0.74 |
| Total Deg in SDI (% area) | | | 0.48 | | | 0.50 |
| Assay (% LC) | 95.3 | 95.6 | 96.4 | 95.4 | 94.1 | 93.0 |
| Storage | | | T = 1 month 25° C./60% RH | | | |
| Total deg (% area) | 1.40 | 1.78 | 2.02 | 2.71 | 2.31 | 1.24 |
| Total Deg in SDI (% area) | | | 0.88 | | | 0.81 |
| Assay (% LC) | 92.8 | 91.4 | 90.6 | 87.8 | 86.5 | 91.9 |
| Storage | | | T = 3 months 5° C. | | | |
| Total deg (% area) | 0.71 | 0.82 | 0.86 | 0.73 | 0.83 | 1.02 |
| Total Deg in SDI (% area) | | | 1.06 | | | 0.74 |
| Assay (% LC) | 96.9 | 94.4 | 92.0 | 94.4 | 94.9 | 93.7 |
| Storage | | | T = 3 months 25° C./60% RH | | | |
| Total deg (% area) | 6.50 | 7.11 | 7.67 | 8.12 | 8.51 | 6.77 |
| Total Deg in SDI (% area) | | | 5.68 | | | 6.34 |
| Assay (% LC) | 74.2 | 70.0 | 65.1 | 66.8 | 66.4 | 72.1 |
| Storage | | | T = 6 months 5° C. | | | |
| Total deg (% area) | 1.12 | 1.36 | 1.92 | 1.10 | 1.77 | 1.93 |
| Total Deg in SDI (% area) | | | 2.17 | | | 1.65 |
| Assay (% LC) | 91.4 | 91.4 | 88.7 | 91.6 | 86.7 | 87.5 |

Although the present invention has been described hereinabove by way of specific embodiments thereof, it can be modified, without departing from the character and nature of the subject invention as defined in the appended claims. The scope of the claims should not be limited by the preferred embodiments set forth in the examples, but should be given the broadest interpretation consistent with the description as a whole. In the claims, the word "comprising" is used as an open-ended term, substantially equivalent to the phrase "including, but not limited to". The singular forms "a", "an" and "the" include corresponding plural references unless the context clearly dictates otherwise.

What is claimed is:

1. A method for treating or lessening the severity of a disease or condition selected from an inflammatory disease or condition, a metabolic disease or condition, and cancer, said method comprising administering to a subject in need thereof an effective amount of an oral dosage formulation comprising an amorphous solid dispersion comprising fenretinide or an analog thereof and at least one matrix polymer selected from a polyvinylpyrrolidone, a hydroxypropyl cellulose, a hydroxypropyl methylcellulose hypromellose phthalate, a polyvinylpyrrolidone-vinyl acetate, a hypromellose-acetate-succinate, and any mixture thereof, wherein:
   (a) at least 55% of said fenretinide or analog thereof in said amorphous solid dispersion is in amorphous form;
   (b) said fenretinide or analog thereof is present in an amount in the range of about 20% to about 60% by weight in said amorphous solid dispersion; and
   (c) said fenretinide analog is 4-oxo-N-(4-hydroxyphenyl) retinamide, N-(4-methoxyphenyl)retinamide (4-MPR), 4-hydroxybenzylretinone, 4-(retinamido)phenyl-C-glucuronide, 4-(retinamido)phenyl-C-glucoside, 4-(retinamido)benzyl-C-xyloside, 1-W-D-glucopyranosyl) retinamide, 1-(D-glucopyranosyluronosyl) retinamide, bexarotene, or a compound of formula I:

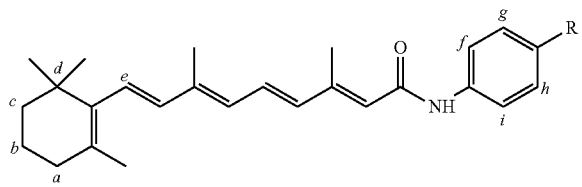

(I)

wherein
R is OH, COOH, $CH_2OH$, $CH_2CH_2OH$, or $CH_2COOH$;
carbons a-d and f-i are optionally substituted with one or more groups selected from $CH_3$, OH, COOH, $(CH_3)_2$ and $CH_2OH$, or any combination thereof, and carbon e is optionally substituted with a $C_1$-$C_3$ alkyl group that is optionally substituted with $CH_3$ and/or OH.

2. The method of claim 1, wherein the matrix polymer comprises a polyvinylpyrrolidone polymer.

3. The method of claim 2, wherein the polyvinylpyrrolidone polymer comprises polyvinylpyrrolidone K30.

4. The method of claim 1, wherein the fenretinide or analog thereof is present in an amount in the range of about 20% to about 30% by weight in said amorphous solid dispersion.

5. The method of claim 1, wherein the [fenretinide or analog thereof/matrix polymer] ratio in said amorphous solid dispersion is about 1/2 to 2/1.

6. The method of claim 1, wherein the amorphous solid dispersion comprises fenretinide.

7. The method of claim 1, wherein the formulation comprises about 50 to about 150 mg of the fenretinide or analog thereof.

8. The method of claim 1, wherein the formulation further comprises at least one pharmaceutical excipient.

9. The method of claim 8, wherein the at least one pharmaceutical excipient comprises an antioxidant.

10. The method of claim 9, wherein the antioxidant comprises butylated hydroxyanisole (BHA), butylated hydroxytoluene (BHT), L-ascorbic acid, or any combination thereof.

11. The method of claim 8, wherein the at least one pharmaceutical excipient comprises a disintegrant.

12. The method of claim 11, wherein the disintegrant comprises croscarmellose sodium.

13. The method of claim 8, wherein the at least one pharmaceutical excipient comprises a filler.

14. The method of claim 13, wherein the filler comprises microcrystalline cellulose, dibasic calcium phosphate, or a combination thereof.

15. The method of claim 8, wherein the at least one pharmaceutical excipient comprises a lubricant.

16. The method of claim 15, wherein the lubricant comprises magnesium stearate.

17. The method of claim 1, wherein the oral dosage formulation is in the form of a capsule.

18. The method of claim 1, wherein the inflammatory disease or condition comprises inflammation of the respiratory tract.

19. The method of claim 1, wherein the inflammatory disease or condition is cystic fibrosis.

20. The method of claim 1, wherein the inflammatory disease or condition comprises neuroinflammation.

21. The method of claim 20, wherein the inflammatory disease or condition is a neural injury or a neurodegenerative disease.

22. The method of claim 21, wherein the inflammatory disease or condition is spinal cord injury, Amyotrophic Lateral Sclerosis, Parkinson's disease, and Huntington's disease.

23. The method of claim 1, wherein the inflammatory disease or condition is macular degeneration.

24. The method of claim 1, wherein the metabolic disease or condition is diabetes or obesity.

25. The method of claim 19, wherein the oral dosage formulation comprises:
fenretinide; polyvinylpyrrolidone K30; BHA; BHT; L-ascorbic acid; croscarmellose sodium;
microcrystalline cellulose; dibasic calcium phosphate; and magnesium stearate.

* * * * *